(12) United States Patent
Whitfield et al.

(10) Patent No.: US 7,819,886 B2
(45) Date of Patent: Oct. 26, 2010

(54) ENDOSCOPIC SURGICAL CLIP APPLIER

(75) Inventors: Kenneth H. Whitfield, New Haven, CT (US); Gregory Sorrentino, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1059 days.

(21) Appl. No.: 11/541,617

(22) Filed: Oct. 2, 2006

(65) Prior Publication Data
US 2007/0093856 A1    Apr. 26, 2007

Related U.S. Application Data

(63) Continuation-in-part of application No. 11/245,523, filed on Oct. 7, 2005, now Pat. No. 7,637,917.

(60) Provisional application No. 60/617,104, filed on Oct. 8, 2004, provisional application No. 60/617,016, filed on Oct. 8, 2004.

(51) Int. Cl.
*A61B 17/10* (2006.01)
(52) U.S. Cl. ...................................... 606/143
(58) Field of Classification Search .................. 606/143, 606/151, 157, 158, 216, 142
See application file for complete search history.

(56) References Cited

U.S. PATENT DOCUMENTS

| | | |
|---|---|---|
| 3,120,230 A | 2/1964 | Skold |
| 3,638,847 A | 2/1972 | Noiles et al. |
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |

(Continued)

FOREIGN PATENT DOCUMENTS

| | | |
|---|---|---|
| EP | 0 732 078 A2 | 9/1996 |
| EP | 0 755 655 A | 1/1997 |
| EP | 0 769 275 | 4/1997 |
| EP | 0834286 A | 4/1998 |
| EP | 13317906 A | 4/2003 |

(Continued)

OTHER PUBLICATIONS

European Search Report for corresponding EP07253807—date of mailing is Nov. 26, 2008 (3 pages).

(Continued)

*Primary Examiner*—Anhtuan T Nguyen
*Assistant Examiner*—Tuan V Nguyen

(57) ABSTRACT

An apparatus for application of surgical clips to body tissue includes an actuator at least partially disposed within a body and longitudinally movable in response to actuation of a handle portion. The apparatus includes a jaw closure member positioned adjacent the first and second jaw portions to move the jaw portions to the approximated position and a rack having ratchet teeth connected to the actuator. The apparatus includes a pawl engaging a series of ratchet teeth and capable of preventing an inadvertent return of the actuator before full actuation of the apparatus. A clip pusher incrementally moves distally each time a clip is released from the apparatus. When the clip pusher reaches a predetermined distal point in a clip carrying channel, a feed bar is deflected to a second position to prevent retraction but not advancement of the actuator and thereby manipulates the pawl to engage the ratchet teeth.

29 Claims, 71 Drawing Sheets

U.S. PATENT DOCUMENTS

| | | |
|---|---|---|
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,336,458 A | 8/1994 | Hutchison et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |

| Patent Number | Date | Inventor(s) | Patent Number | Date | Inventor(s) |
|---|---|---|---|---|---|
| 5,439,468 A | 8/1995 | Schulze et al. | 5,779,720 A | 7/1998 | Walder-Utz et al. |
| 5,441,509 A | 8/1995 | Vidal et al. | 5,782,844 A | 7/1998 | Yoon et al. |
| 5,447,513 A | 9/1995 | Davison et al. | 5,788,698 A | 8/1998 | Savornin |
| 5,449,365 A | 9/1995 | Green et al. | 5,792,149 A | 8/1998 | Sherts et al. |
| 5,462,555 A | 10/1995 | Bolanos et al. | 5,792,150 A | 8/1998 | Pratt et al. |
| 5,462,558 A | 10/1995 | Kolesa et al. | 5,797,922 A | 8/1998 | Hessel et al. |
| 5,464,416 A | 11/1995 | Steckel | 5,810,853 A | 9/1998 | Yoon |
| 5,474,566 A | 12/1995 | Alesi et al. | 5,817,116 A | 10/1998 | Takahashi et al. |
| 5,474,567 A | 12/1995 | Stefanchik et al. | 5,824,547 A | 10/1998 | Hashino et al. |
| 5,474,572 A | 12/1995 | Hayhurst | 5,824,548 A | 10/1998 | Hearn |
| 5,487,746 A | 1/1996 | Yu et al. | 5,827,306 A | 10/1998 | Yoon |
| 5,501,693 A | 3/1996 | Gravener | 5,833,695 A | 11/1998 | Yoon |
| 5,509,920 A | 4/1996 | Phillips et al. | 5,833,696 A | 11/1998 | Whitfield et al. |
| 5,514,149 A | 5/1996 | Green et al. | 5,833,700 A | 11/1998 | Fogelberg et al. |
| 5,520,701 A | 5/1996 | Lerch | 5,835,199 A | 11/1998 | Phillips et al. |
| 5,522,823 A | 6/1996 | Kuntz et al. | 5,843,097 A | 12/1998 | Mayenberger et al. |
| 5,527,318 A | 6/1996 | McGarry | 5,843,101 A | 12/1998 | Fry |
| 5,527,319 A | 6/1996 | Green et al. | 5,846,255 A | 12/1998 | Casey |
| 5,527,320 A | 6/1996 | Carruthers et al. | 5,849,019 A | 12/1998 | Yoon |
| 5,542,949 A | 8/1996 | Yoon | 5,858,018 A | 1/1999 | Shipp et al. |
| 5,547,474 A | 8/1996 | Kloeckl et al. | 5,861,005 A | 1/1999 | Kontos |
| 5,569,274 A | 10/1996 | Rapacki et al. | 5,868,759 A | 2/1999 | Peyser et al. |
| 5,571,121 A | 11/1996 | Heifetz | 5,868,761 A | 2/1999 | Nicholas et al. |
| 5,575,802 A | 11/1996 | McQuildin et al. | 5,876,410 A | 3/1999 | Petillo |
| 5,582,615 A | 12/1996 | Foshee et al. | 5,895,394 A | 4/1999 | Kienzle et al. |
| 5,584,840 A | 12/1996 | Ramsey et al. | 5,897,565 A | 4/1999 | Foster |
| 5,591,178 A | 1/1997 | Green et al. | 5,904,693 A | 5/1999 | Dicesare et al. |
| 5,593,414 A | 1/1997 | Shipp et al. | 5,913,862 A | 6/1999 | Ramsey et al. |
| 5,593,421 A | 1/1997 | Bauer | 5,918,791 A | 7/1999 | Sorrentino et al. |
| 5,601,573 A | 2/1997 | Fogelberg et al. | 5,921,996 A | 7/1999 | Sherman |
| 5,601,574 A | 2/1997 | Stefanchik et al. | 5,921,997 A | 7/1999 | Fogelberg et al. |
| 5,607,436 A | 3/1997 | Pratt et al. | 5,928,251 A | 7/1999 | Aranyi et al. |
| 5,618,291 A | 4/1997 | Thompson et al. | 5,938,667 A | 8/1999 | Peyser et al. |
| 5,618,306 A | 4/1997 | Roth et al. | 5,951,574 A | 9/1999 | Stefanchik et al. |
| 5,620,452 A | 4/1997 | Yoon | 5,972,003 A | 10/1999 | Rousseau et al. |
| 5,626,585 A | 5/1997 | Mittelstadt et al. | 5,976,159 A | 11/1999 | Bolduc et al. |
| 5,626,586 A | 5/1997 | Pistl et al. | 5,993,465 A | 11/1999 | Shipp et al. |
| 5,626,592 A | 5/1997 | Phillips et al. | 6,004,335 A | 12/1999 | Vaitekunas et al. |
| RE35,525 E | 6/1997 | Stefanchik et al. | 6,017,358 A | 1/2000 | Yoon et al. |
| 5,634,930 A | 6/1997 | Thornton et al. | RE36,720 E | 5/2000 | Green et al. |
| 5,643,291 A | 7/1997 | Pier et al. | 6,059,799 A | 5/2000 | Aranyi et al. |
| 5,645,551 A | 7/1997 | Green et al. | 6,099,536 A | 8/2000 | Petillo |
| 5,645,553 A | 7/1997 | Kolesa et al. | 6,099,537 A | 8/2000 | Sugai et al. |
| 5,649,937 A | 7/1997 | Bito et al. | 6,139,555 A | 10/2000 | Hart et al. |
| 5,653,720 A | 8/1997 | Johnson et al. | 6,210,418 B1 | 4/2001 | Storz et al. |
| 5,662,676 A | 9/1997 | Koninckx | 6,217,590 B1 | 4/2001 | Levinson |
| 5,662,679 A | 9/1997 | Voss et al. | 6,228,097 B1 | 5/2001 | Levinson et al. |
| 5,665,097 A | 9/1997 | Baker et al. | 6,241,740 B1 | 6/2001 | Davis et al. |
| 5,676,676 A | 10/1997 | Porter | 6,258,105 B1 | 7/2001 | Hart et al. |
| 5,681,330 A | 10/1997 | Hughett et al. | 6,261,302 B1 | 7/2001 | Voegele et al. |
| 5,683,405 A | 11/1997 | Yacoubian et al. | 6,273,898 B1 | 8/2001 | Kienzle et al. |
| 5,695,502 A | 12/1997 | Pier et al. | 6,277,131 B1 | 8/2001 | Kalikow |
| 5,695,505 A | 12/1997 | Yoon | 6,306,149 B1 | 10/2001 | Meade |
| 5,697,938 A | 12/1997 | Jensen et al. | 6,318,619 B1 | 11/2001 | Lee |
| 5,700,270 A | 12/1997 | Peyser et al. | 6,322,571 B1 | 11/2001 | Adams |
| 5,700,271 A | 12/1997 | Whitfield et al. | 6,350,269 B1 | 2/2002 | Shipp et al. |
| 5,702,048 A | 12/1997 | Eberlin | 6,352,541 B1 | 3/2002 | Kienzle et al. |
| 5,709,706 A | 1/1998 | Kienzle et al. | 6,391,035 B1 | 5/2002 | Appleby et al. |
| 5,713,911 A | 2/1998 | Racenet et al. | 6,423,079 B1 | 7/2002 | Blake, III |
| 5,713,912 A | 2/1998 | Porter | 6,428,548 B1 | 8/2002 | Durgin et al. |
| 5,720,756 A | 2/1998 | Green et al. | 6,440,144 B1 | 8/2002 | Bacher |
| 5,722,982 A | 3/1998 | Ferreira et al. | 6,461,363 B1 | 10/2002 | Gadberry et al. |
| 5,725,537 A | 3/1998 | Green et al. | 6,464,710 B1 | 10/2002 | Foster |
| 5,725,538 A | 3/1998 | Green et al. | 6,494,886 B1 | 12/2002 | Wilk et al. |
| 5,725,542 A | 3/1998 | Yoon | 6,517,536 B2 | 2/2003 | Hooven et al. |
| 5,733,295 A | 3/1998 | Back et al. | 6,520,972 B2 | 2/2003 | Peters |
| 5,755,726 A | 5/1998 | Pratt et al. | 6,527,786 B1 | 3/2003 | Davis et al. |
| 5,766,189 A | 6/1998 | Matsuno | 6,537,289 B1 | 3/2003 | Kayan et al. |
| 5,769,857 A | 6/1998 | Reztzov et al. | 6,546,935 B2 | 4/2003 | Hooven |
| 5,772,673 A | 6/1998 | Cuny et al. | 6,551,333 B2 | 4/2003 | Kuhns et al. |
| 5,776,146 A | 7/1998 | Sackier et al. | 6,569,171 B2 | 5/2003 | DeGuillebon et al. |
| 5,776,147 A | 7/1998 | Dolendo | 6,579,304 B1 | 6/2003 | Hart et al. |
| 5,779,718 A | 7/1998 | Green et al. | 6,599,298 B1 | 7/2003 | Forster et al. |

| Patent Number | Date | Inventor |
|---|---|---|
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,446 B2 | 12/2005 | Hommann et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,635 B2 | 1/2006 | Sugiyama et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,696 B2 | 1/2008 | Wilson, Jr. et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |

| | | |
|---|---|---|
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |

FOREIGN PATENT DOCUMENTS

| | | |
|---|---|---|
| EP | 1 609 427 A1 | 12/2005 |
| EP | 1 712 191 A2 | 10/2006 |
| EP | 1 908 423 A | 4/2008 |
| EP | 1 913 881 A1 | 4/2008 |
| WO | WO2005/091457 | 9/2005 |
| WO | WO 2006/042076 | 4/2006 |
| WO | WO 2006/042084 | 4/2006 |
| WO | WO 2006/042110 | 4/2006 |
| WO | WO 2008/118928 A2 | 10/2008 |
| WO | WO 2008/127968 A | 10/2008 |

OTHER PUBLICATIONS

International Search Report for application EP 07 25 3905 date Feb. 7, 2008.
European Search Report for corresponding Eruopean Application EP07253807—Date of Mailing Aug. 1, 2008 (1 page).
International Search Report from PCT Application No. PCT/US08/58185 dated Sep. 9, 2008.
International Search Report from PCT Application No. PCT/US08/59859 dated Sep. 18, 2008.
European Search Report corresponding to EP 09252053; date of mailing is Dec. 1, 2009; date of completion of Search is Nov. 24, 2009 (3 Pages).
European Search Report corresponding to EP 09252049; date of mailing is Jan. 12, 2010; date of completion of Search is Dec. 11, 2009 (3 Pages).
European Search Report corresponding to EP 09252051; date of mailing is Jan. 28, 20 1 0; date of completion of Search is Dec. 21, 2009 (3 Pages).

European Search Report corresponding to EP 09252050; date of mailing is Jan. 21, 2010; date of completion of Search is Dec. 23, 2009 (3 Pages).

European Search Report corresponding to EP 09252054; date of mailing is Jan. 22, 2010; date of completion of Search is Jan. 7, 2010 (3 Pages).

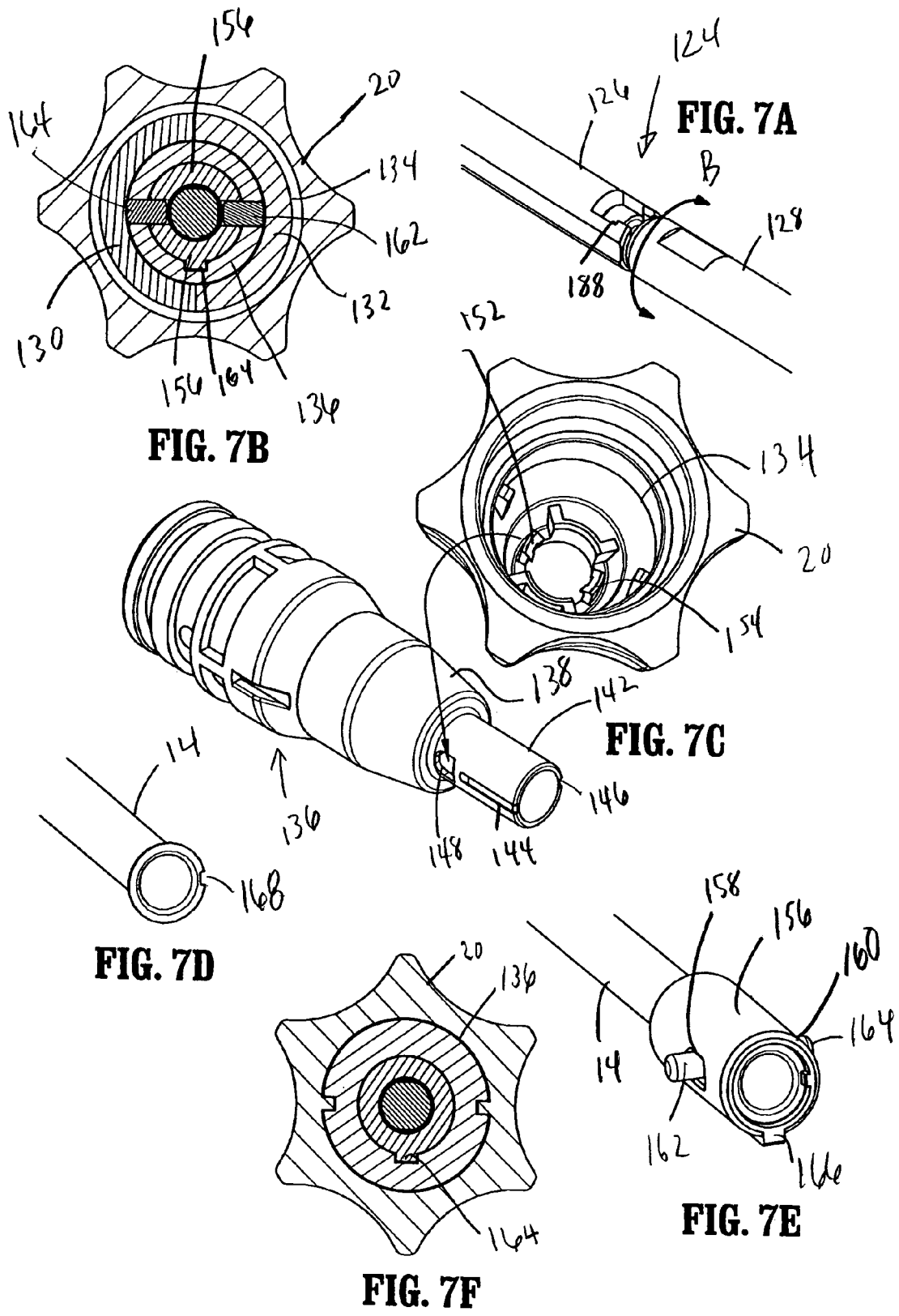

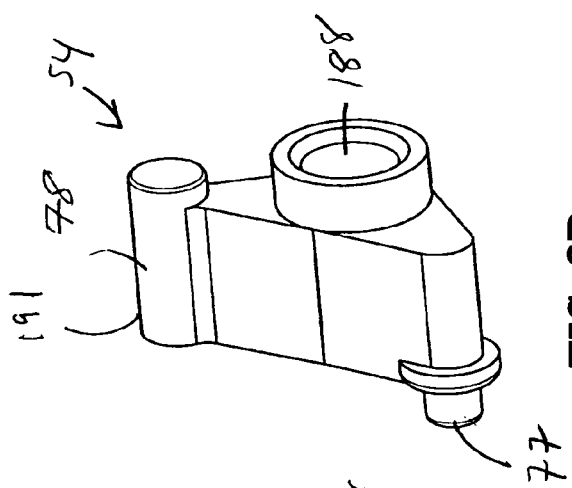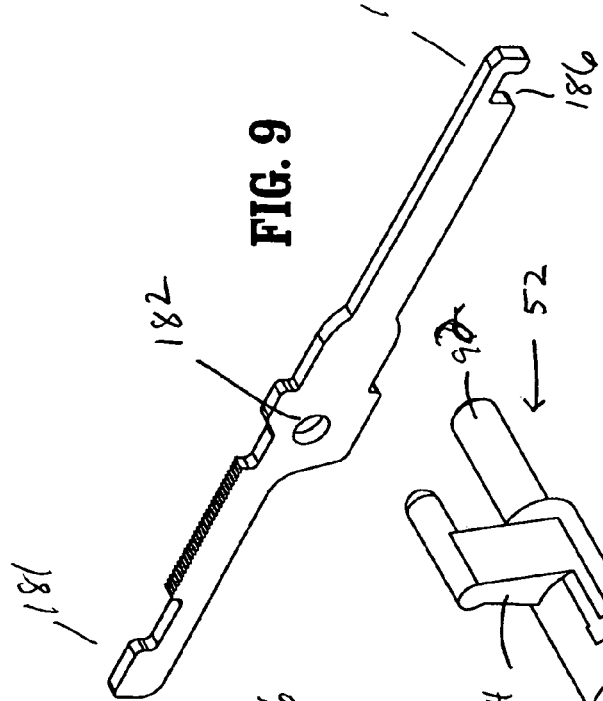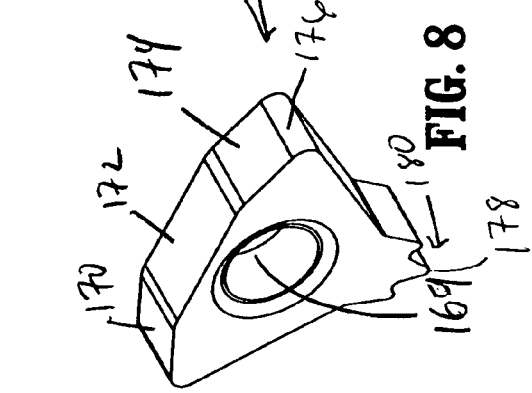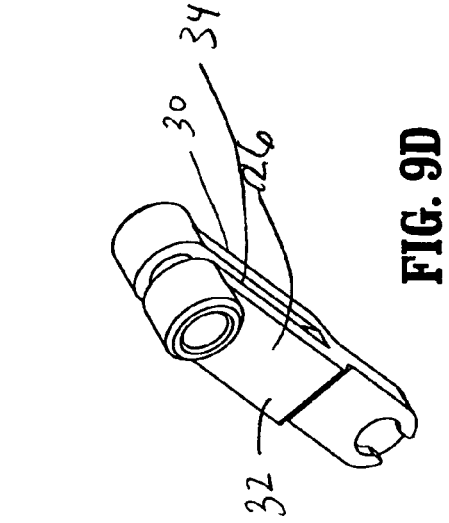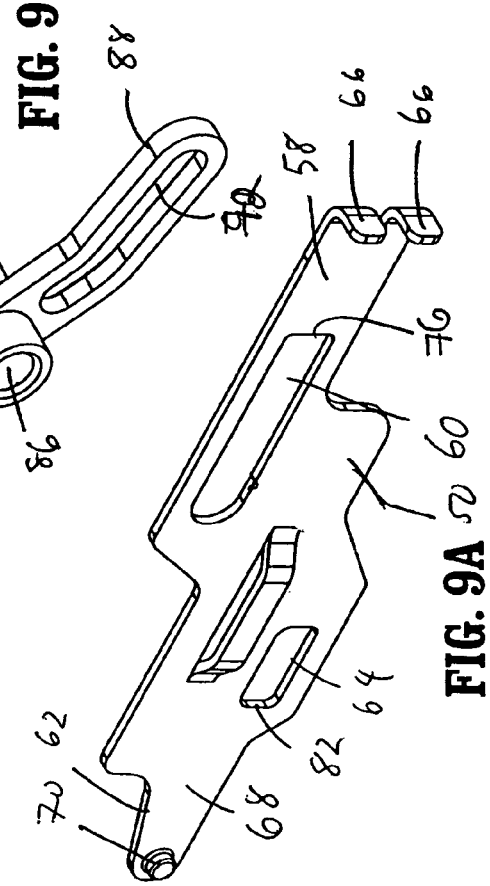

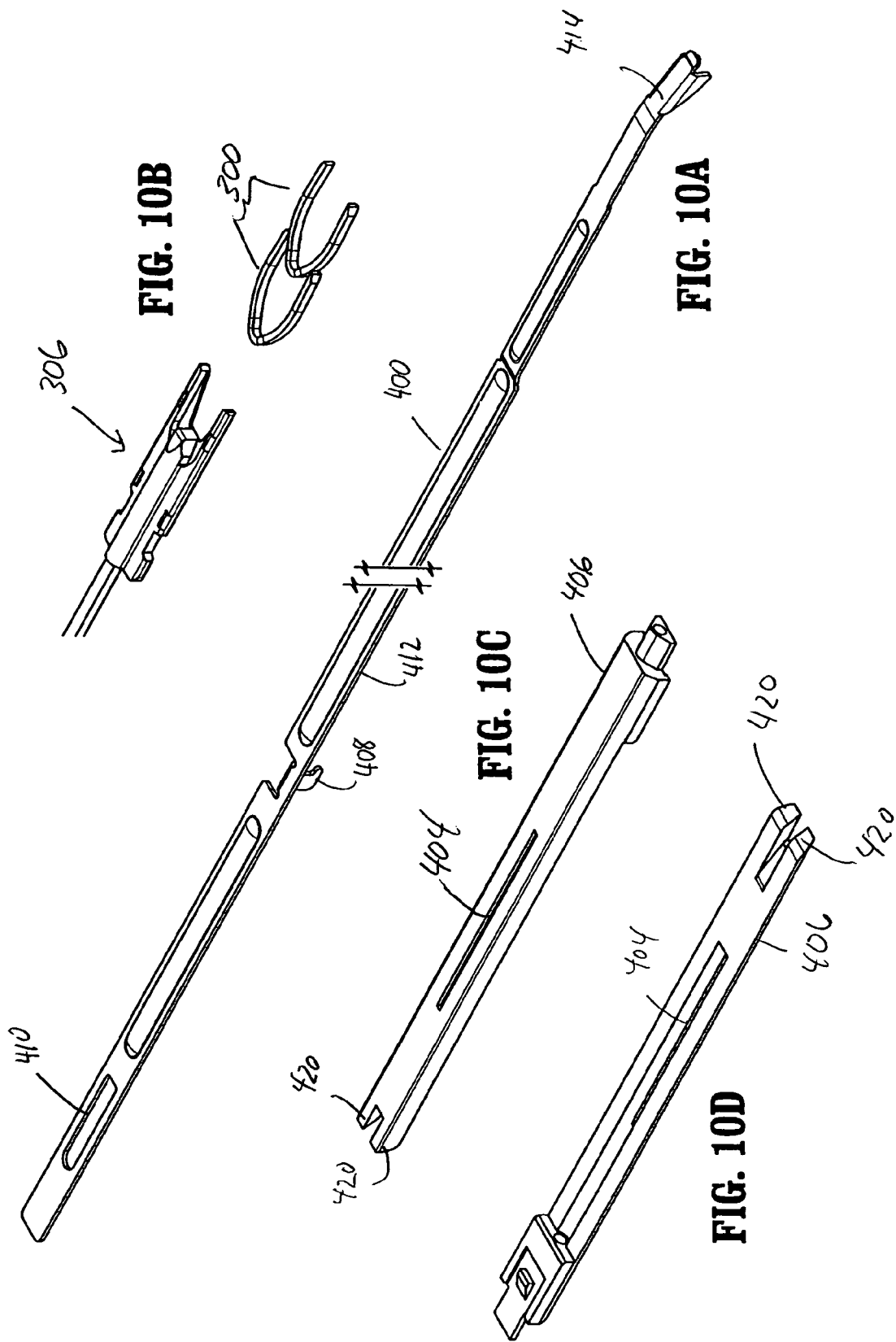

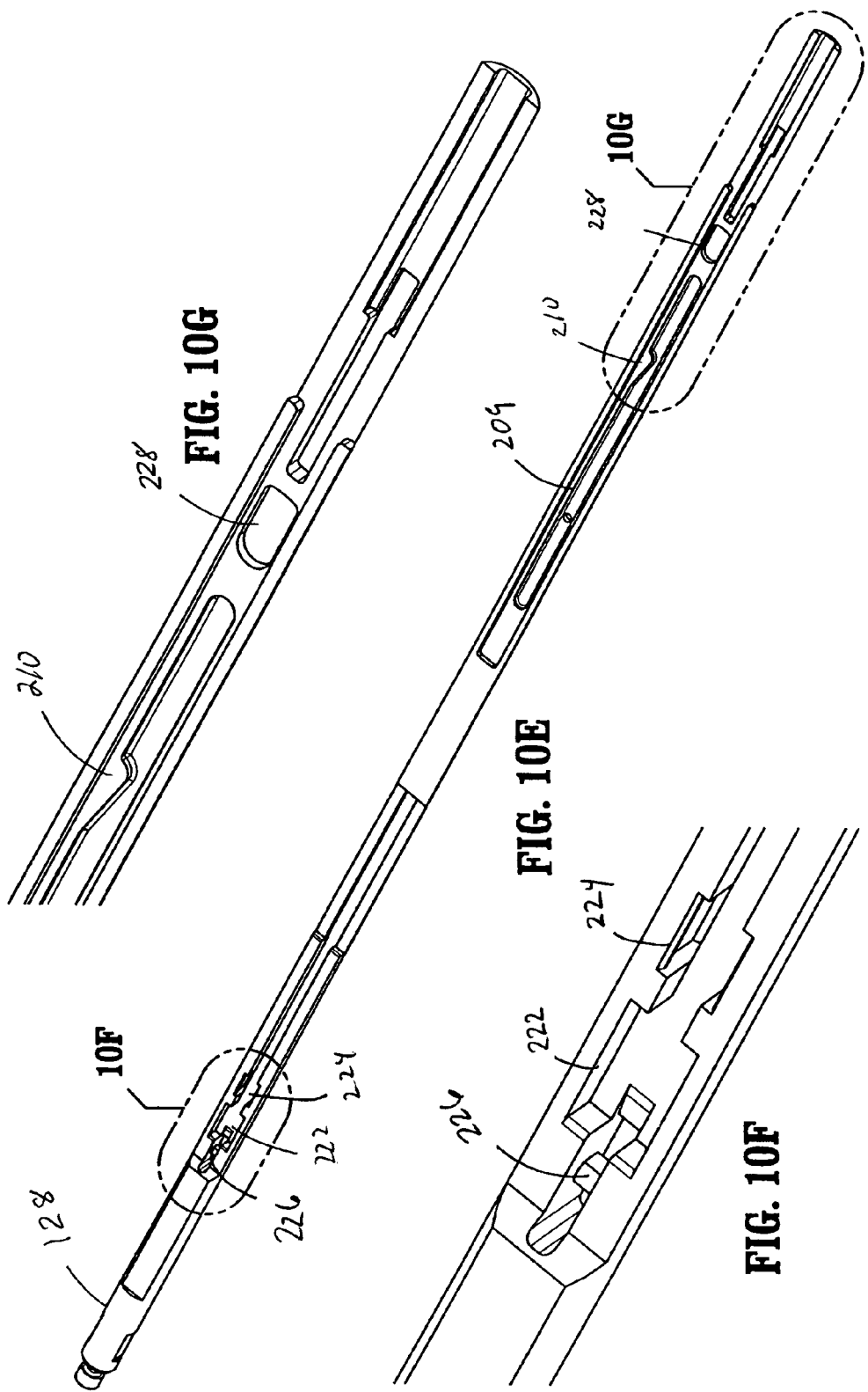

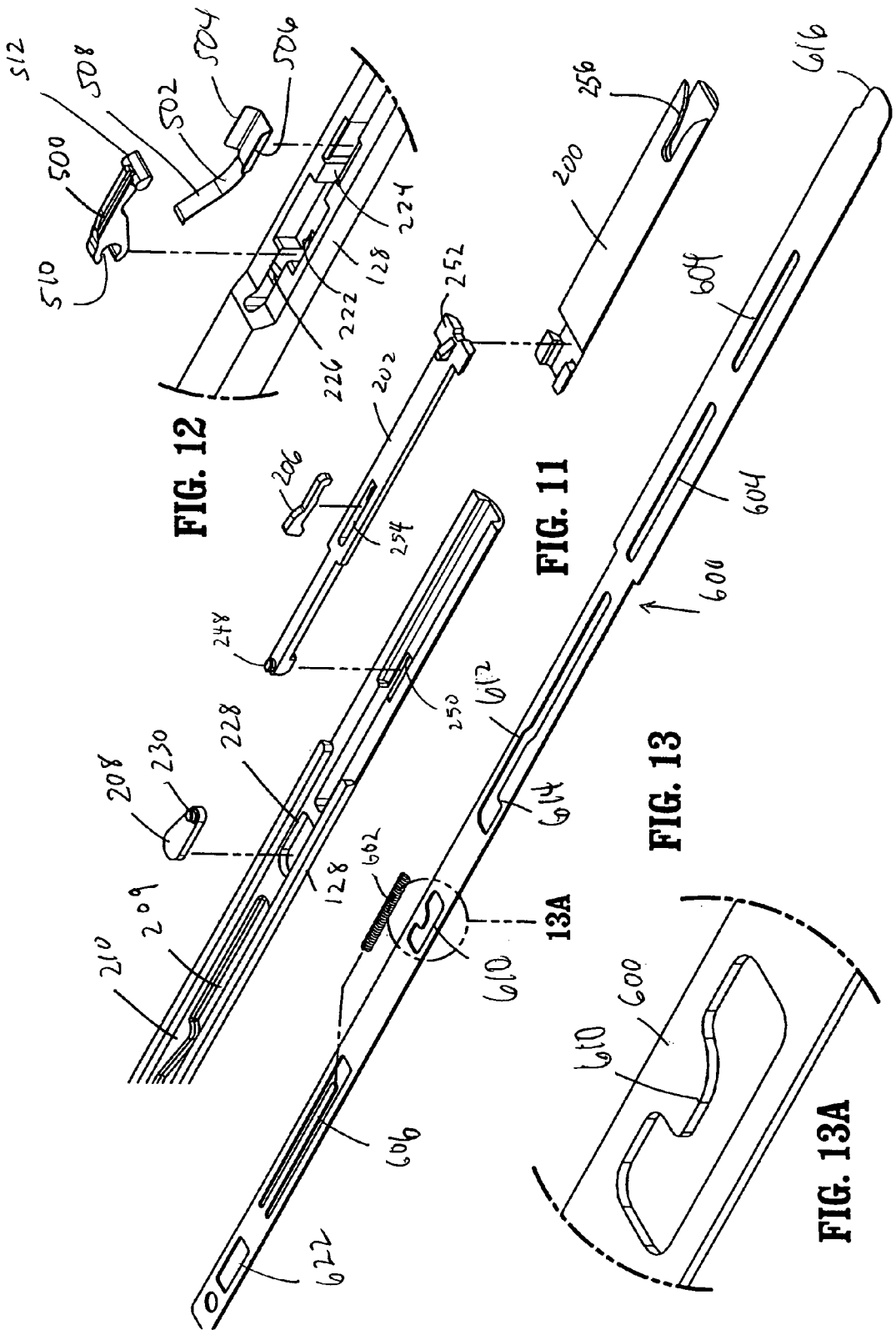

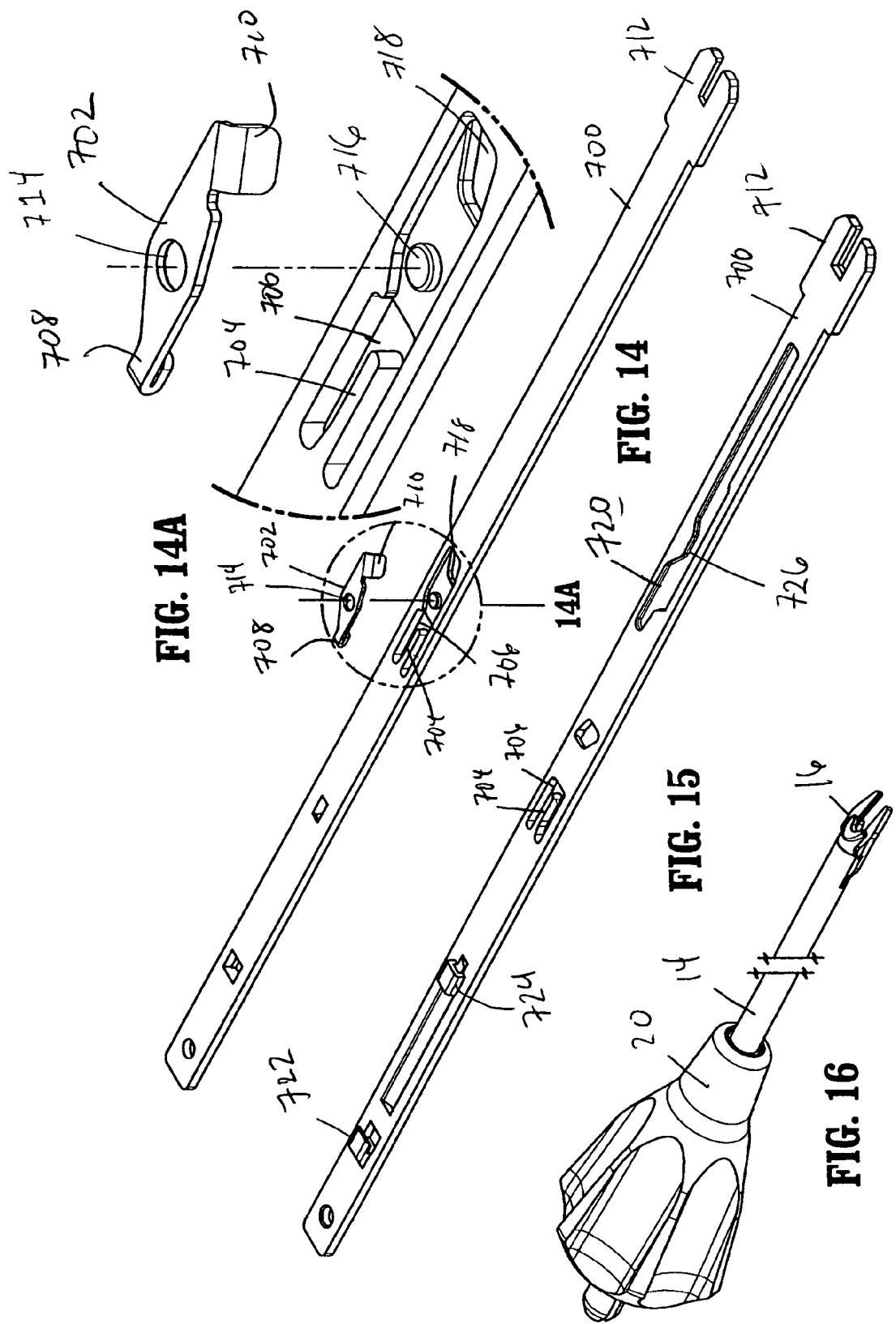

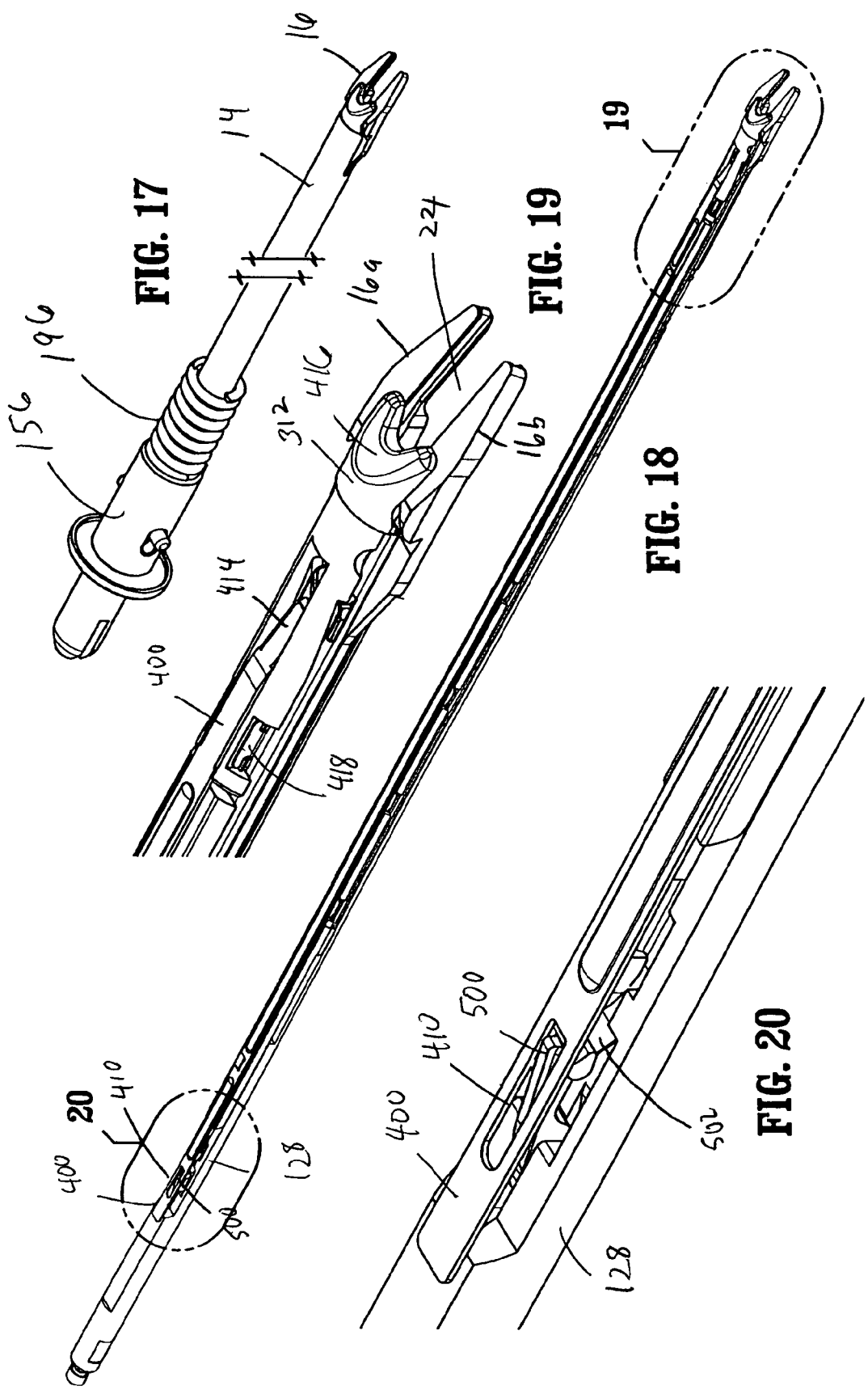

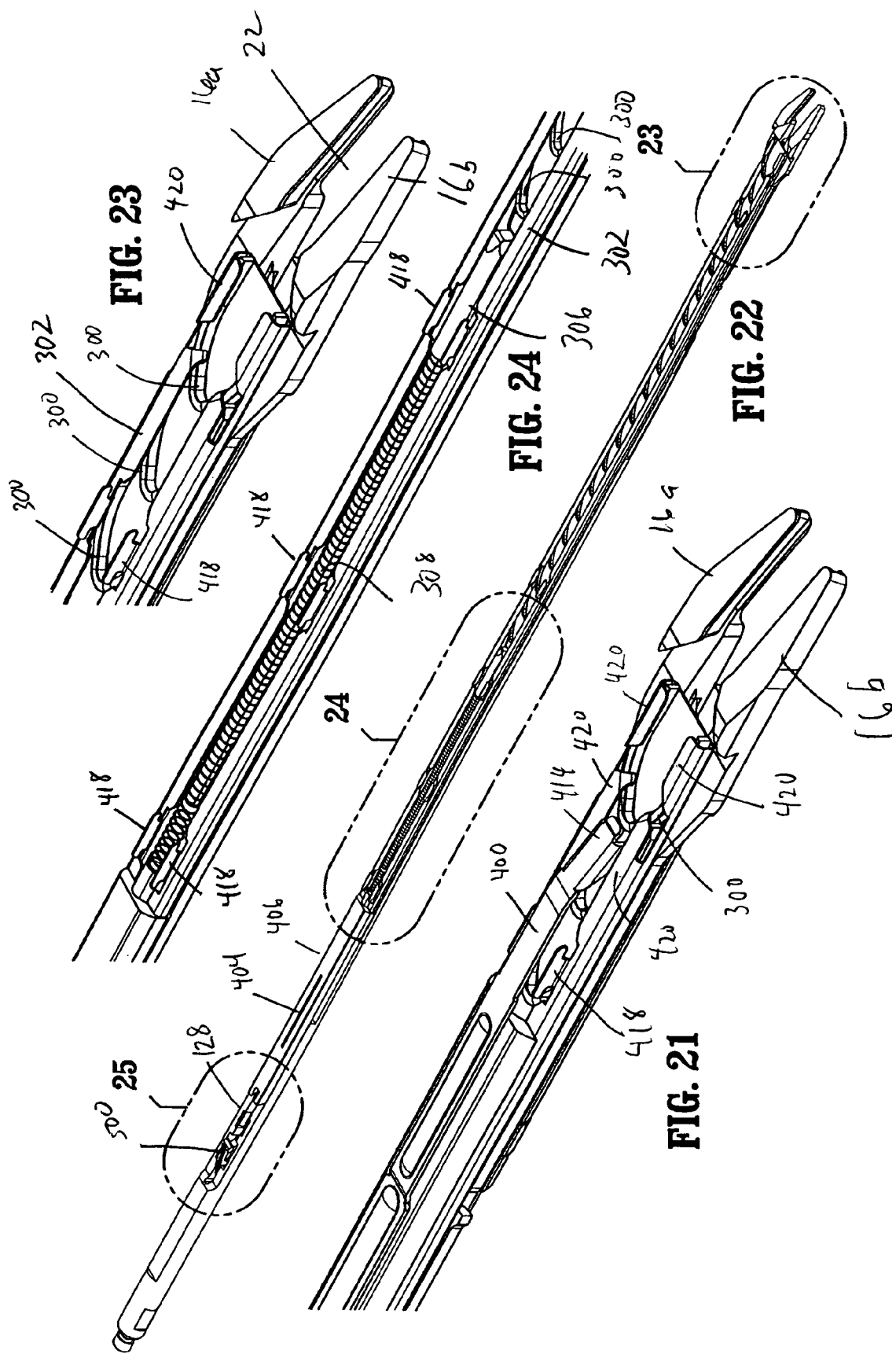

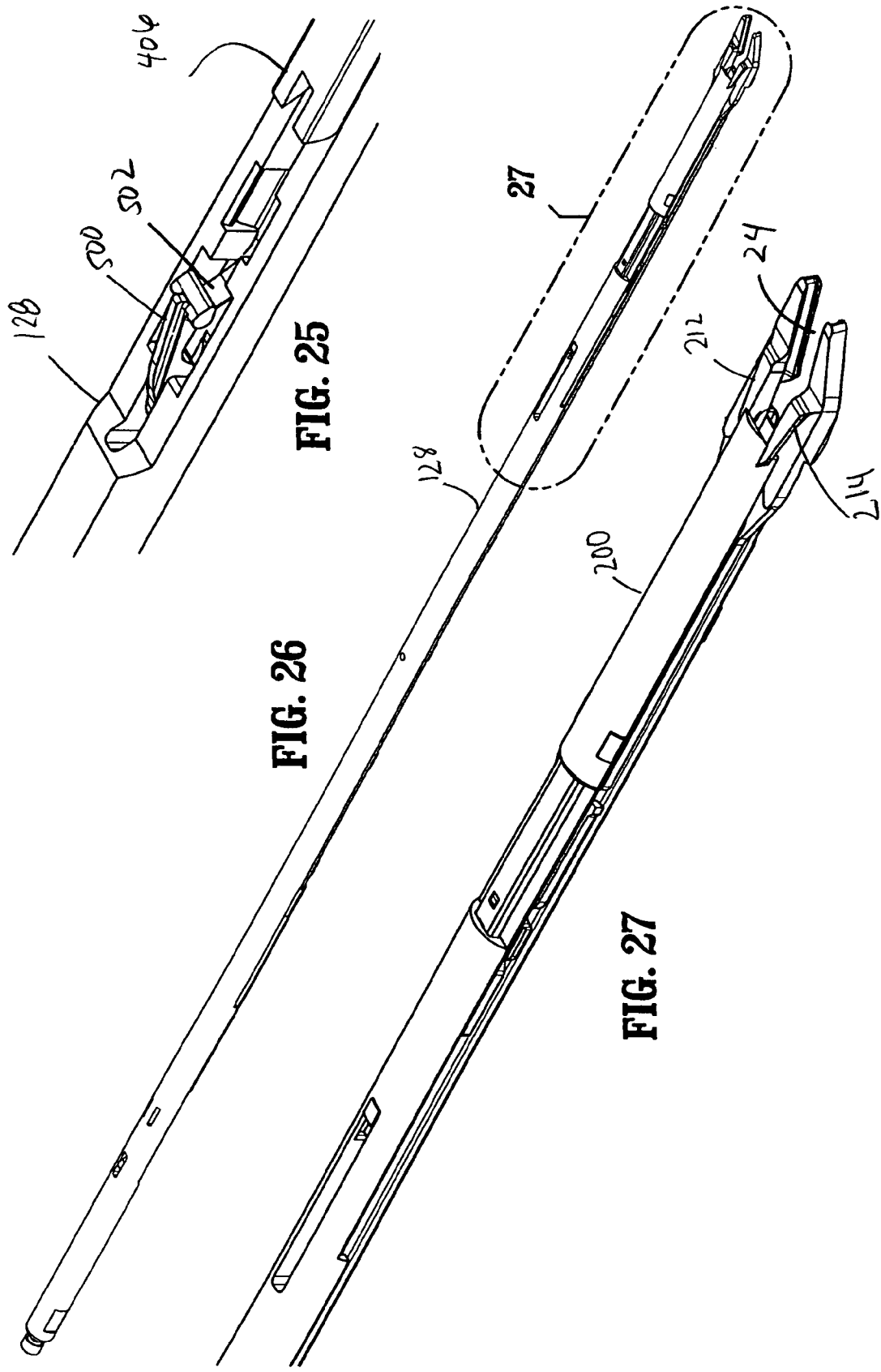

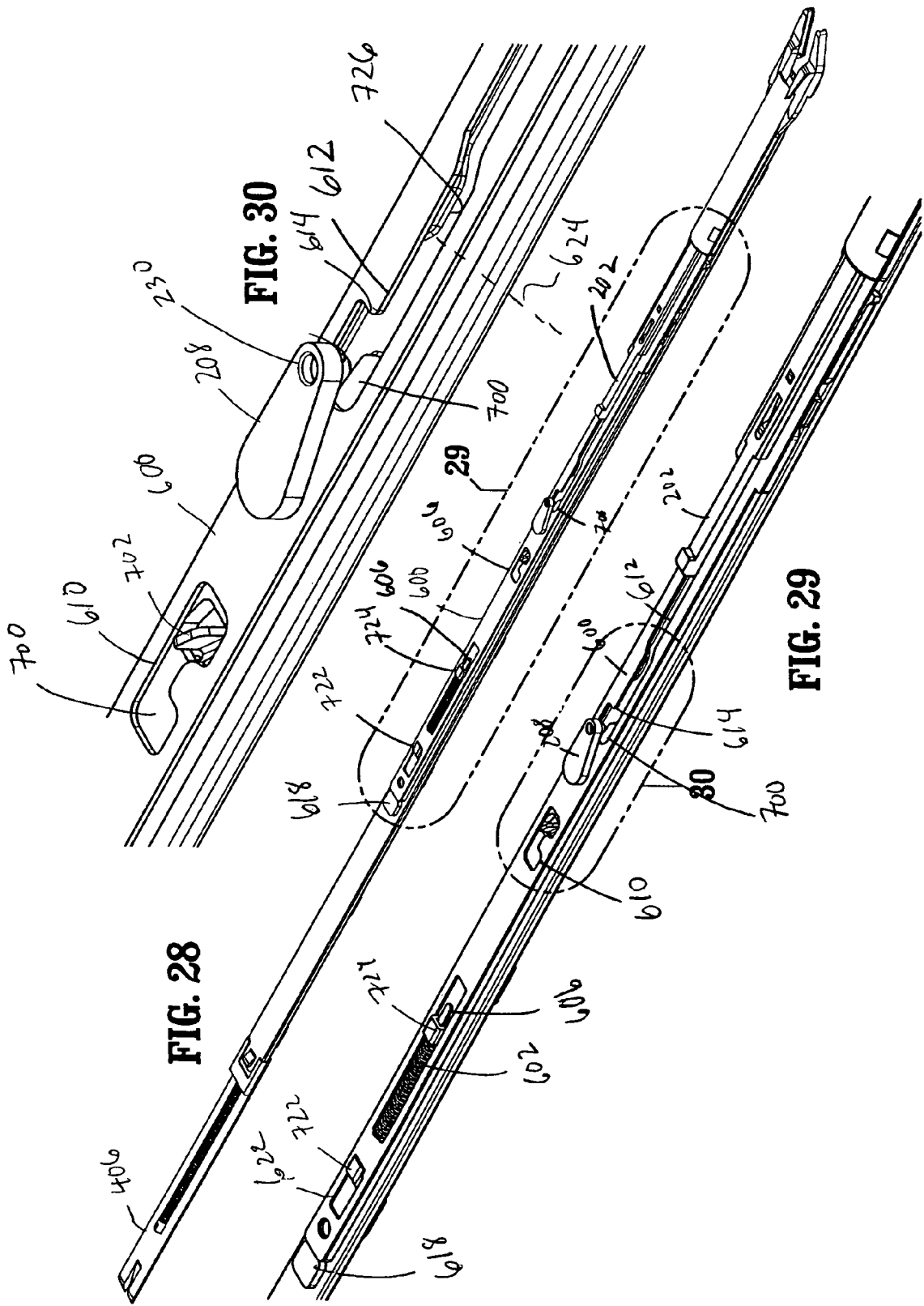

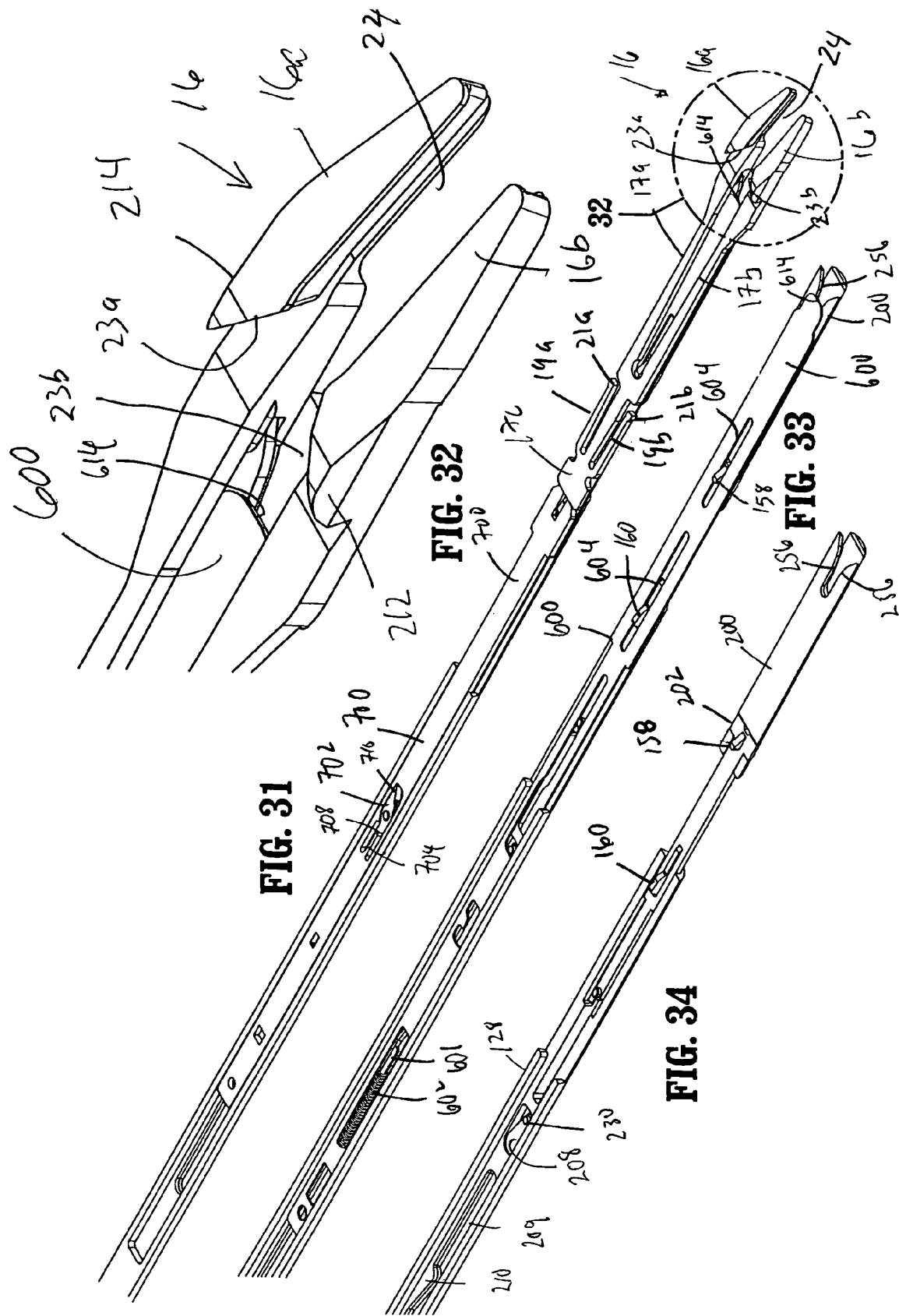

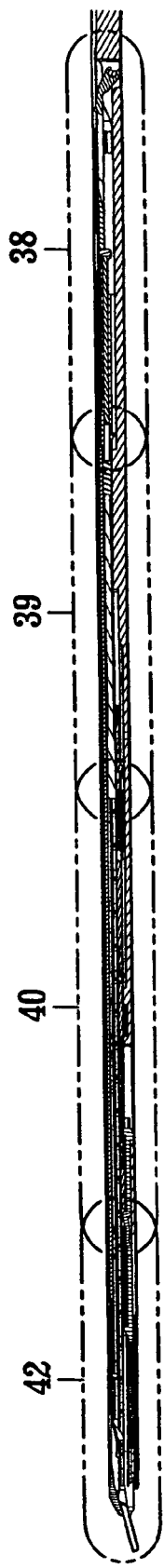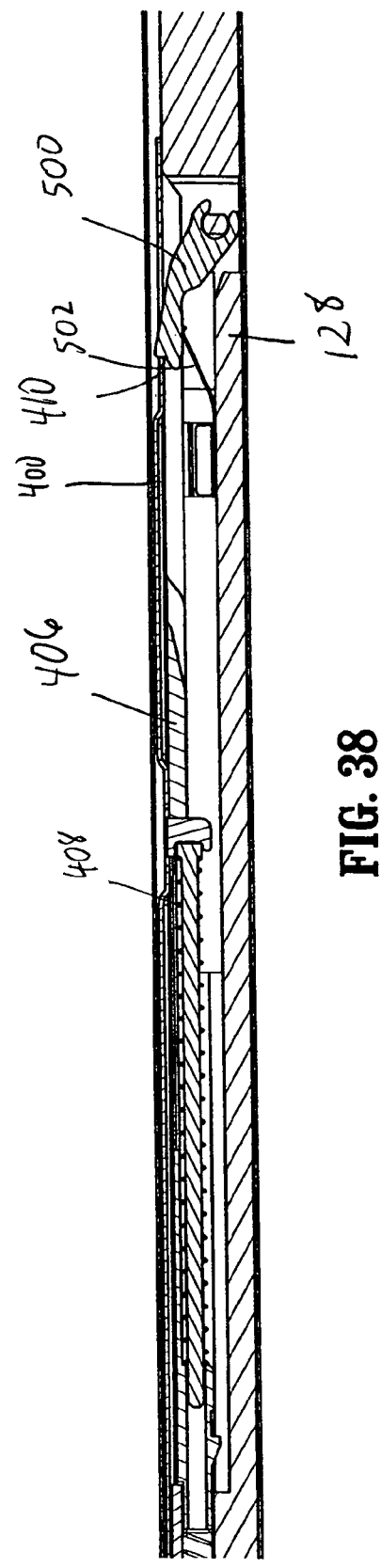
FIG. 37
FIG. 38

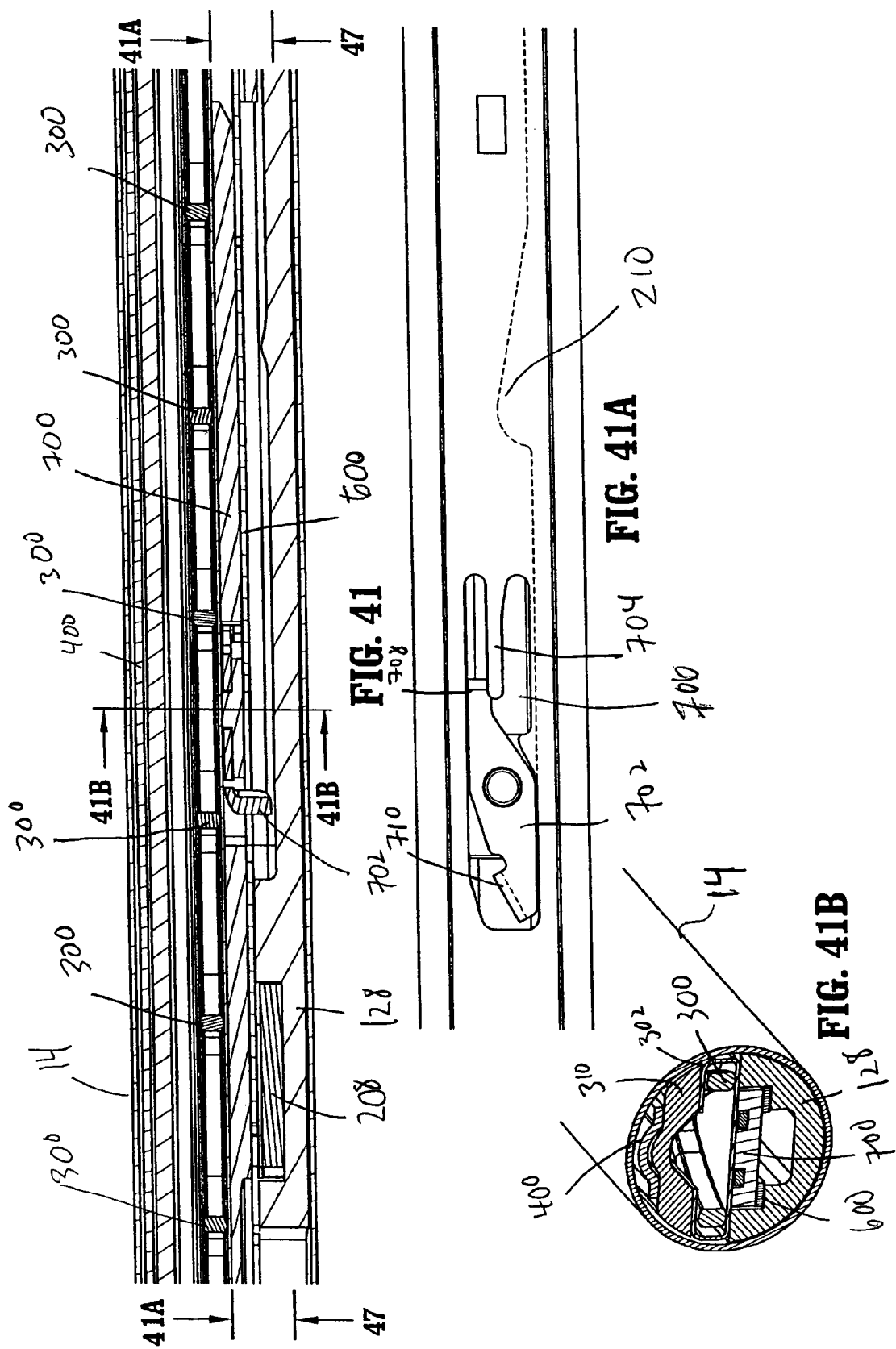

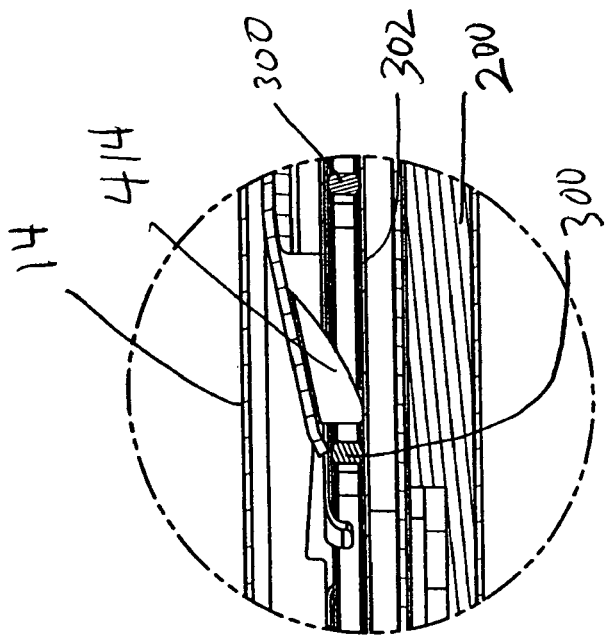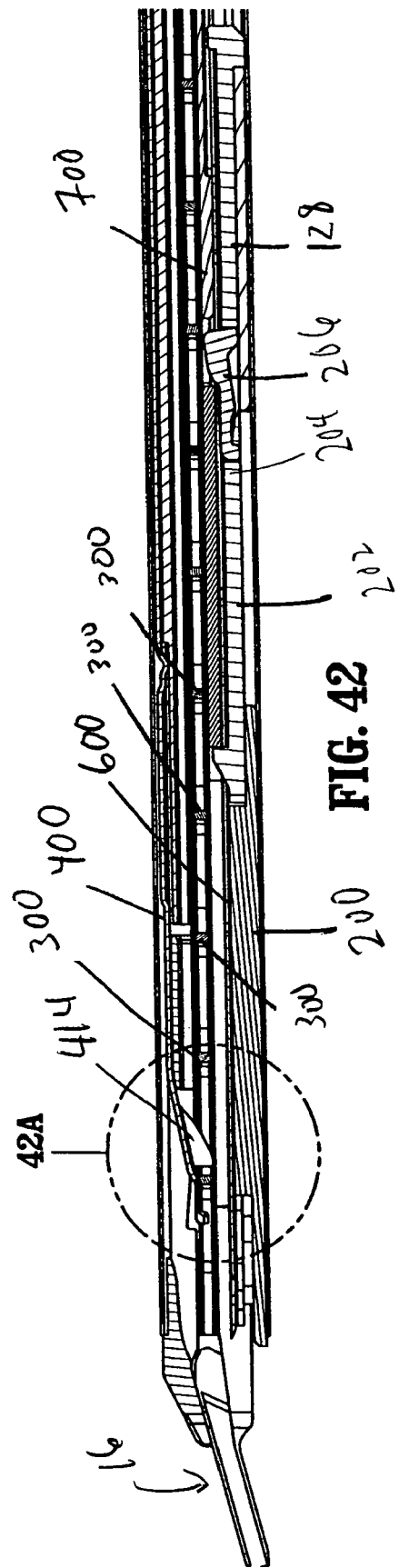

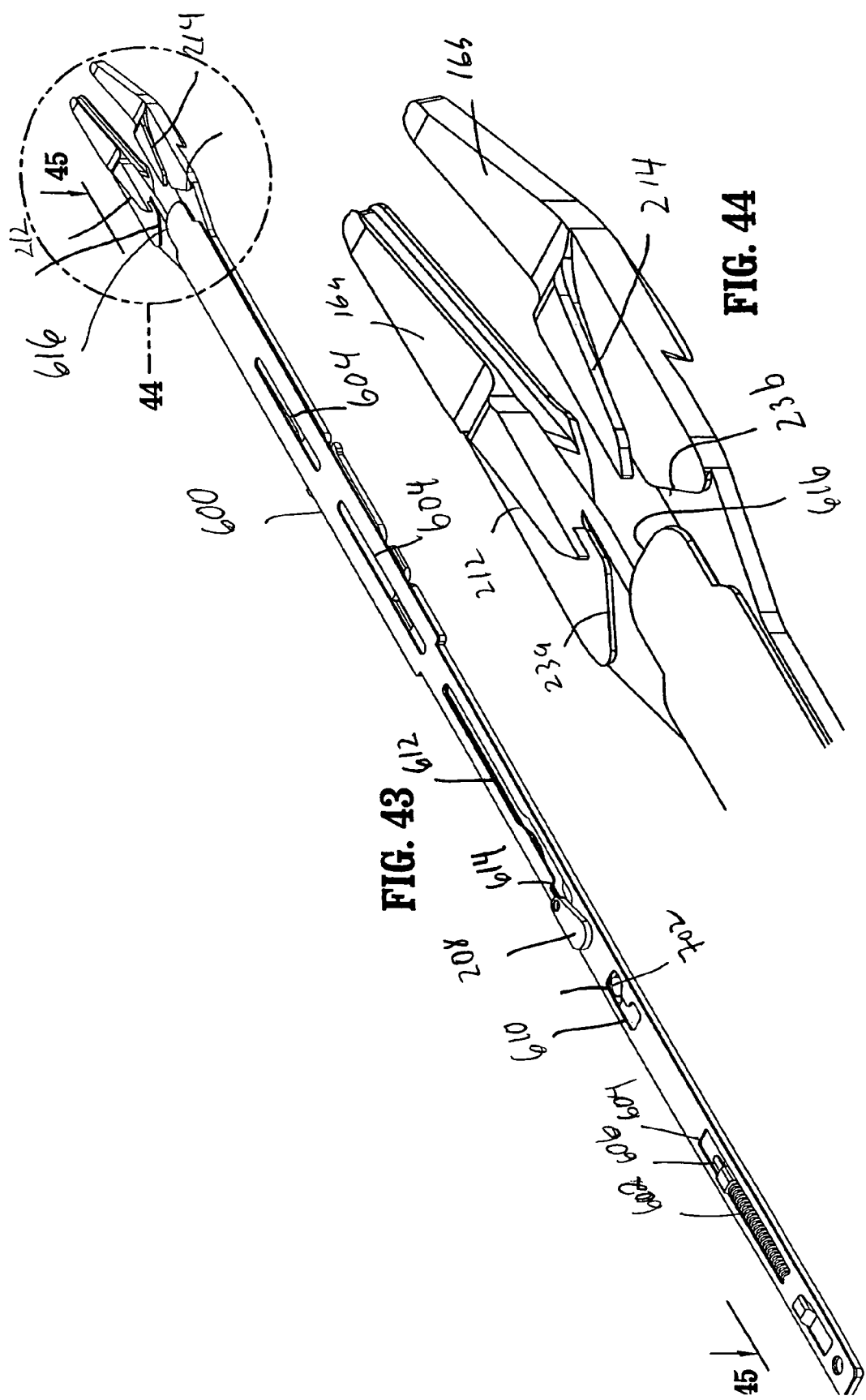

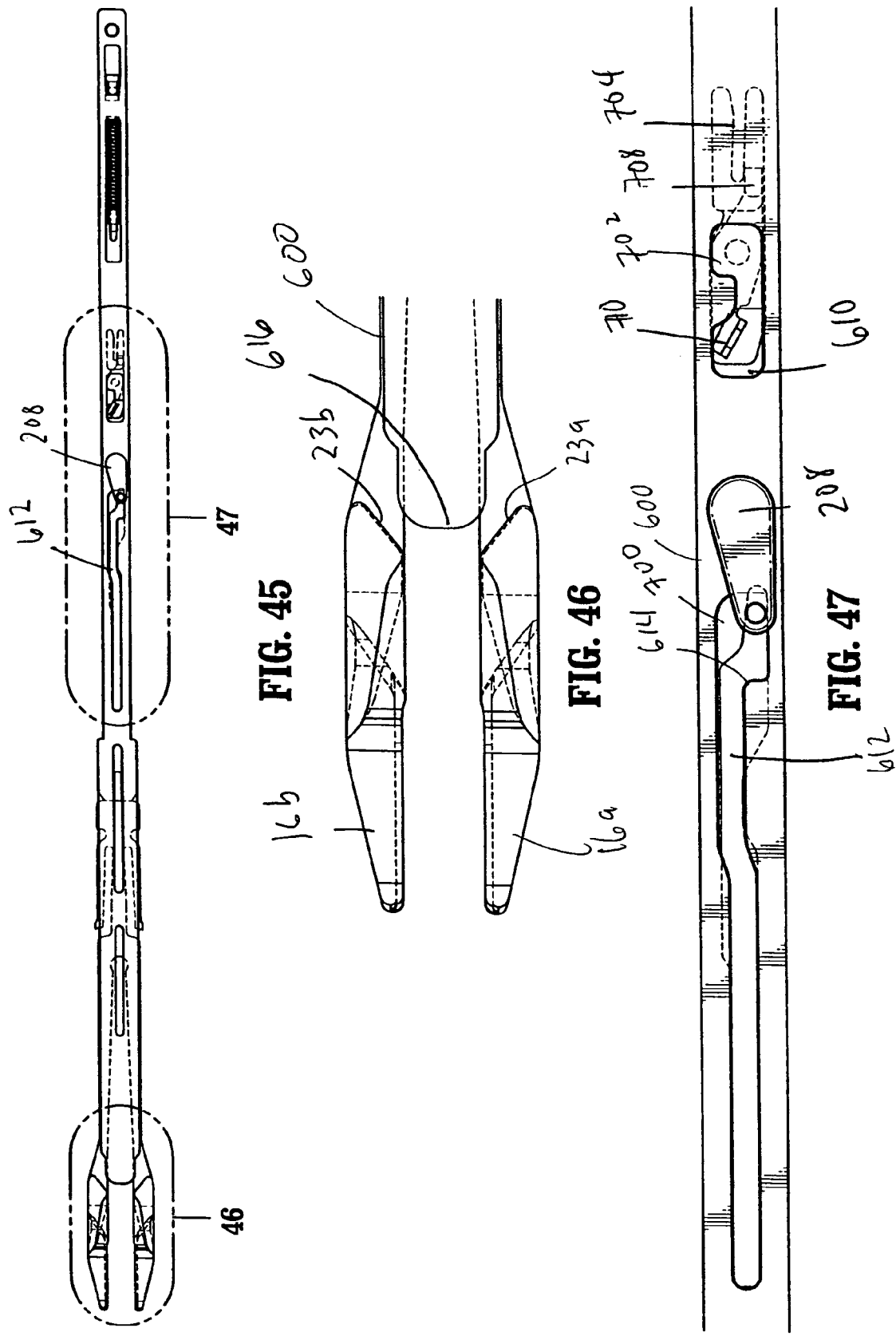

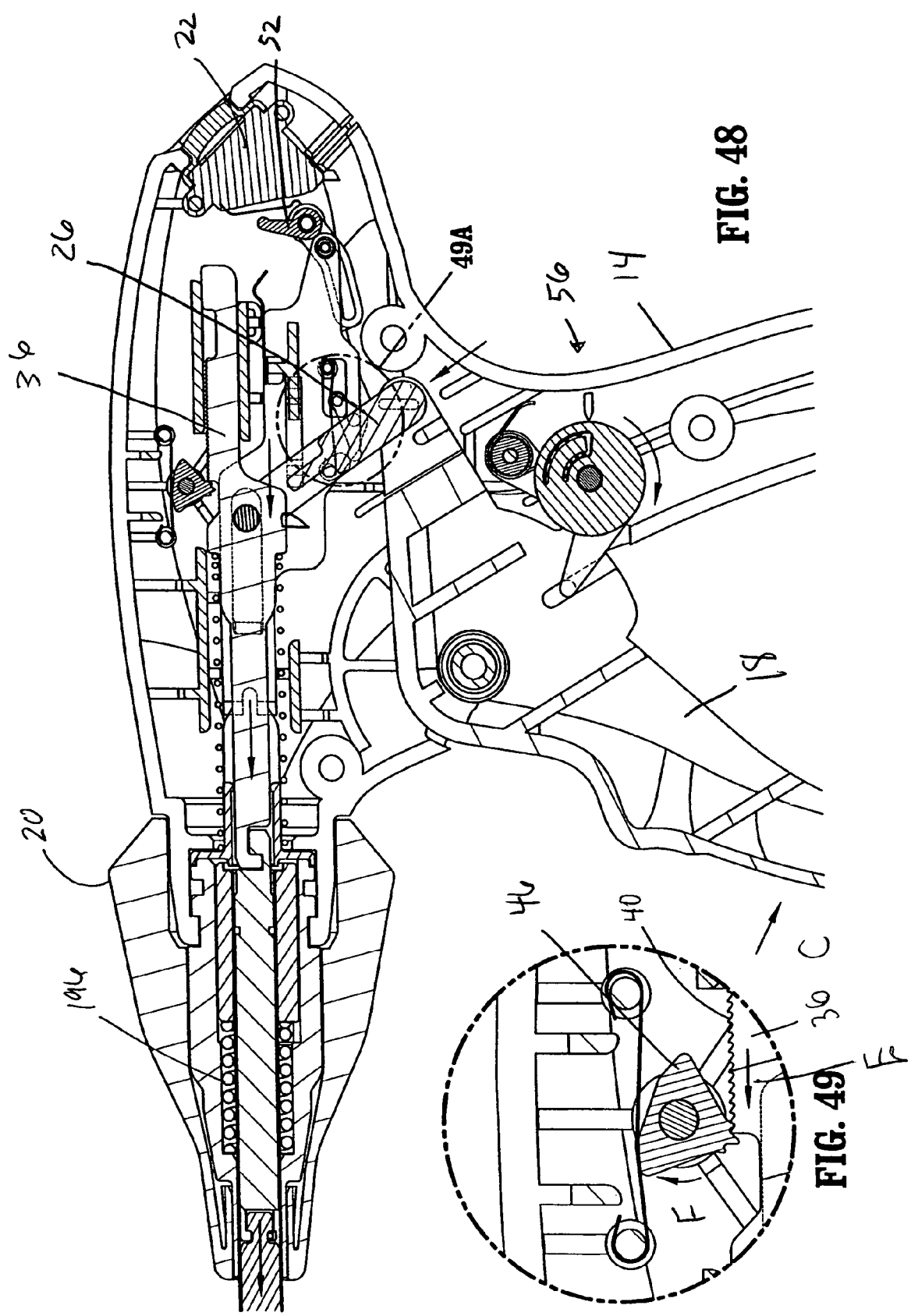

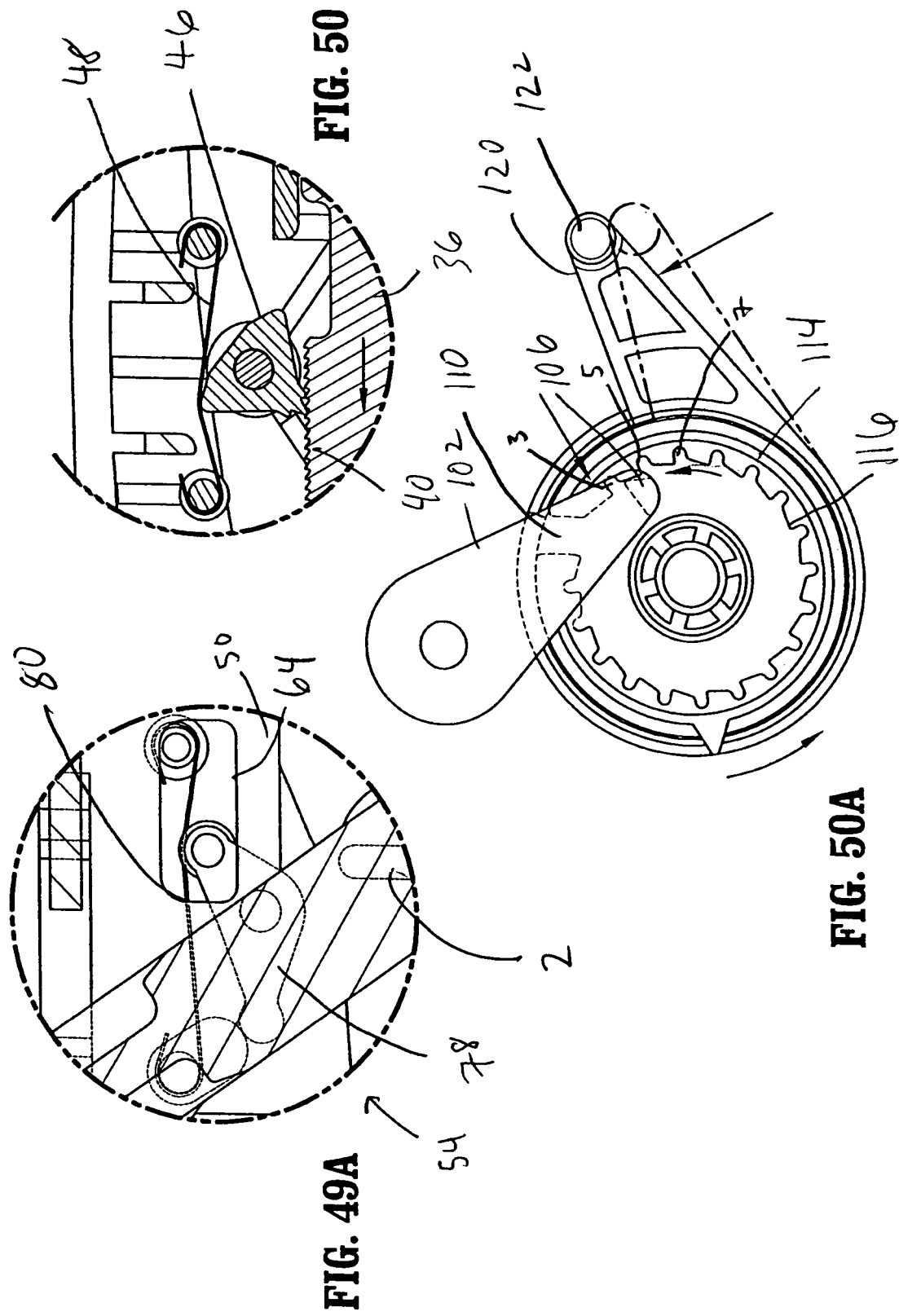

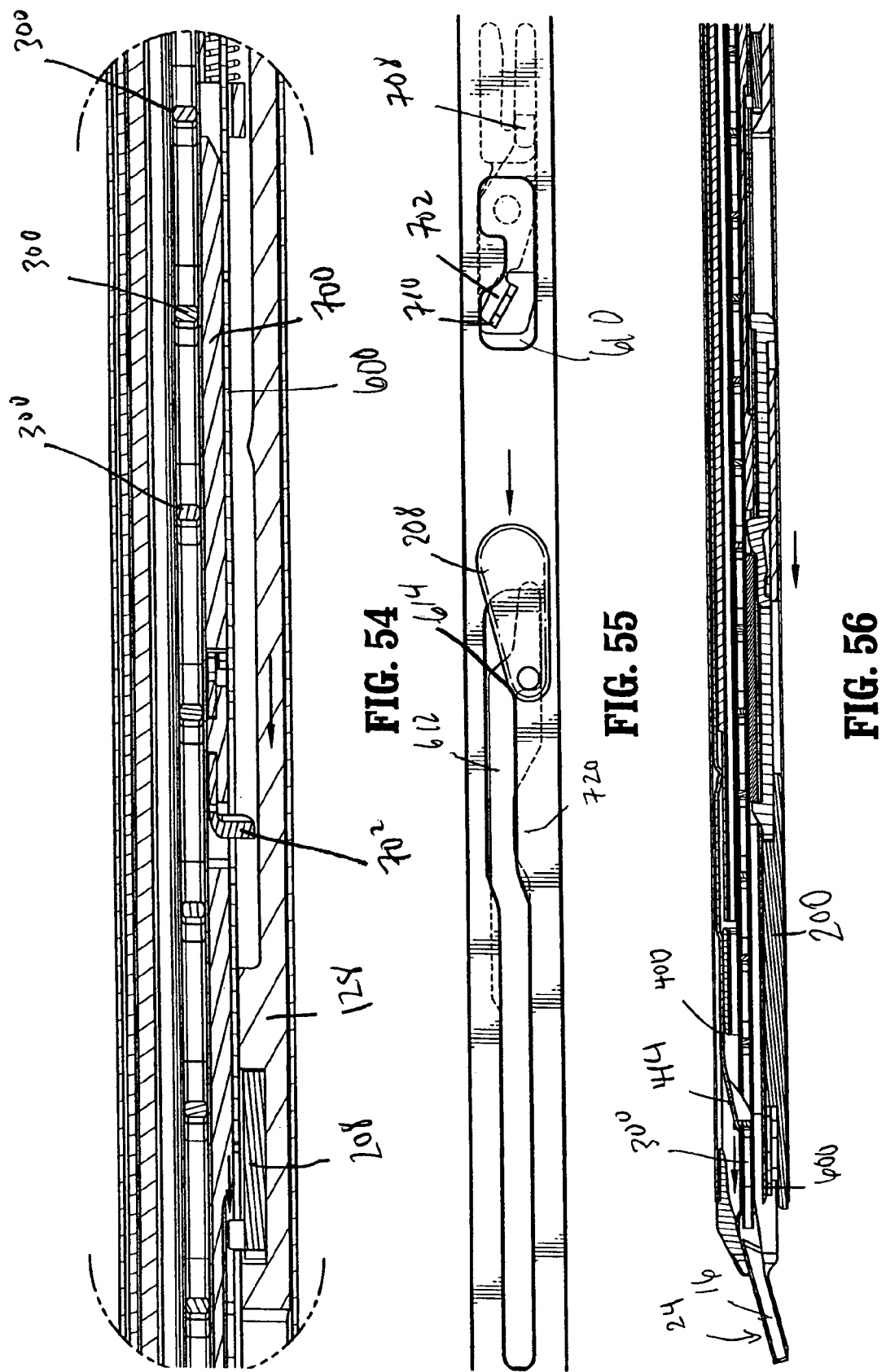

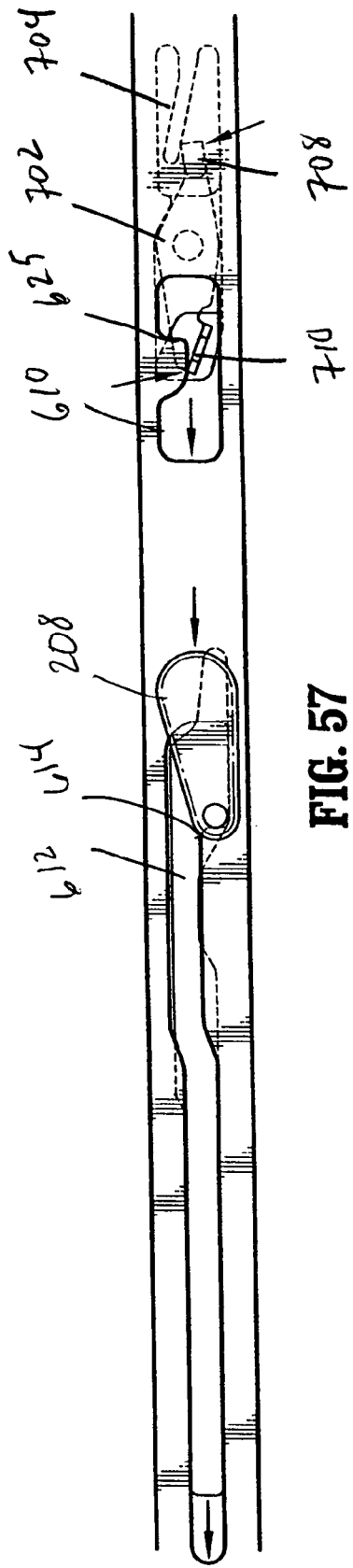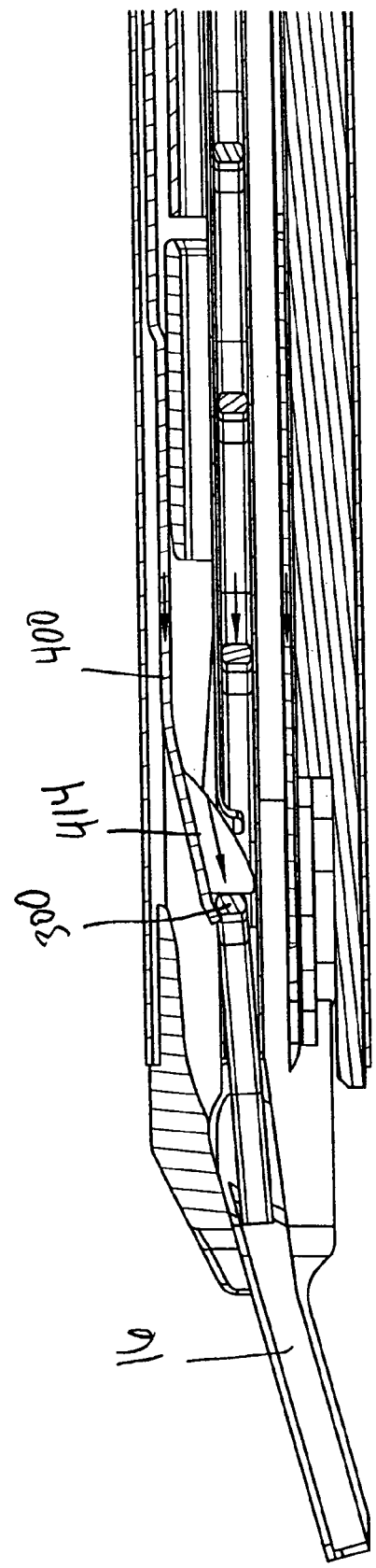
FIG. 57
FIG. 58

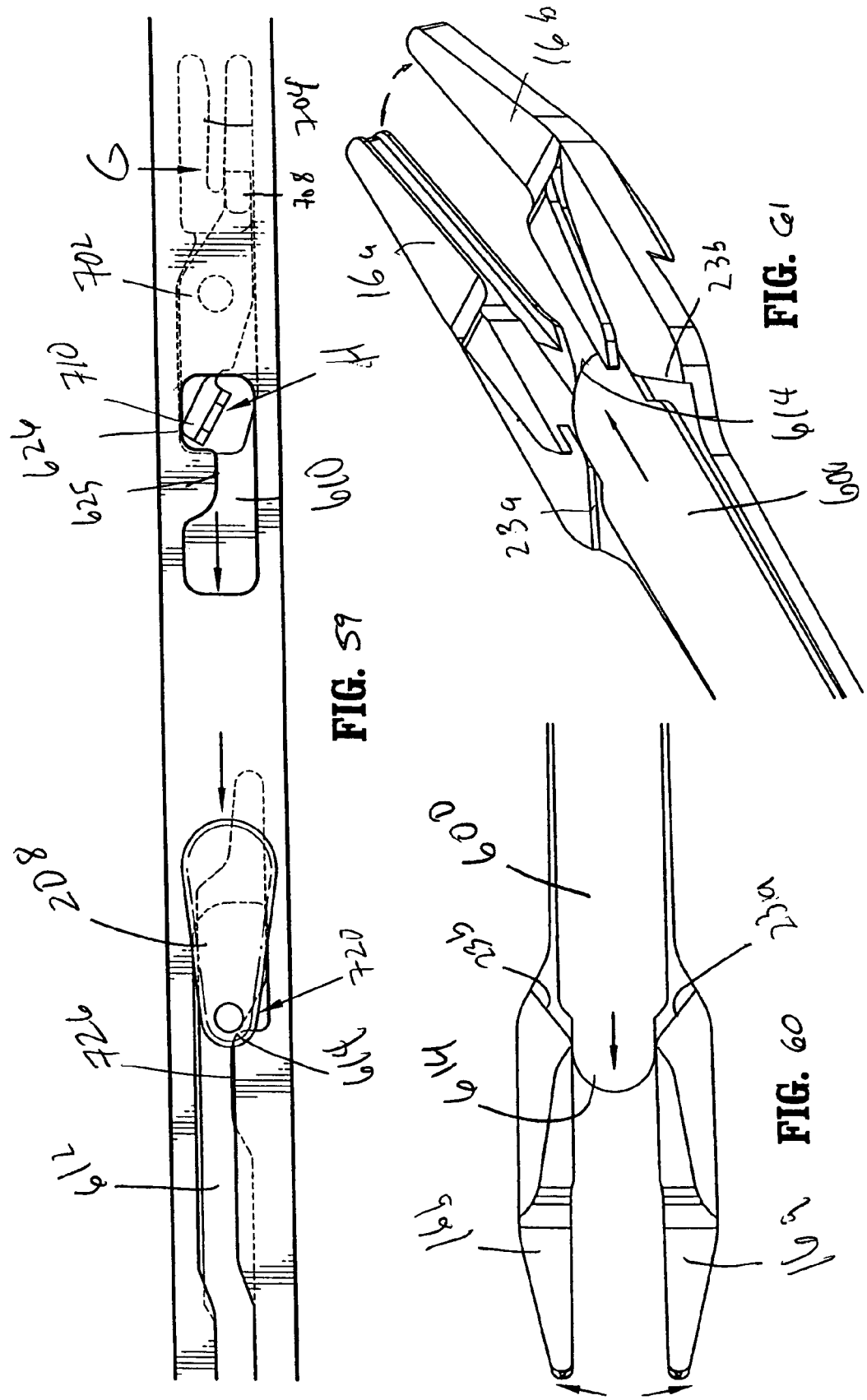

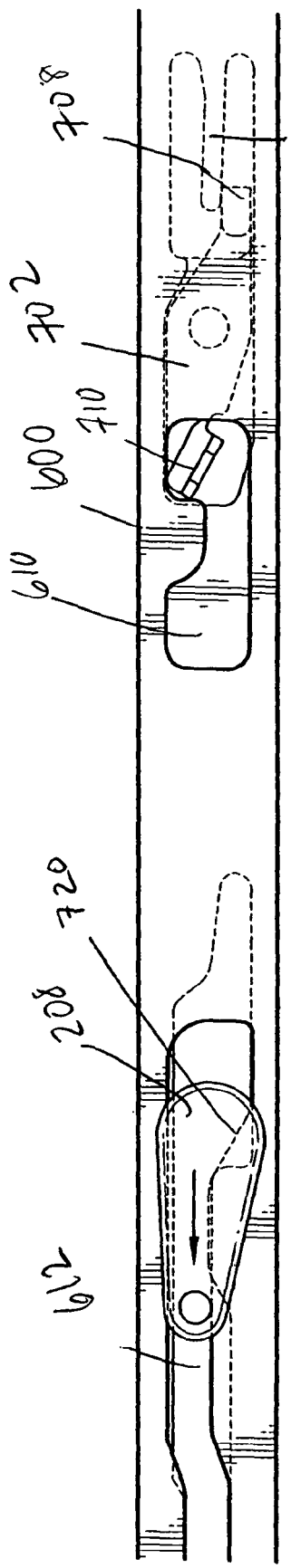
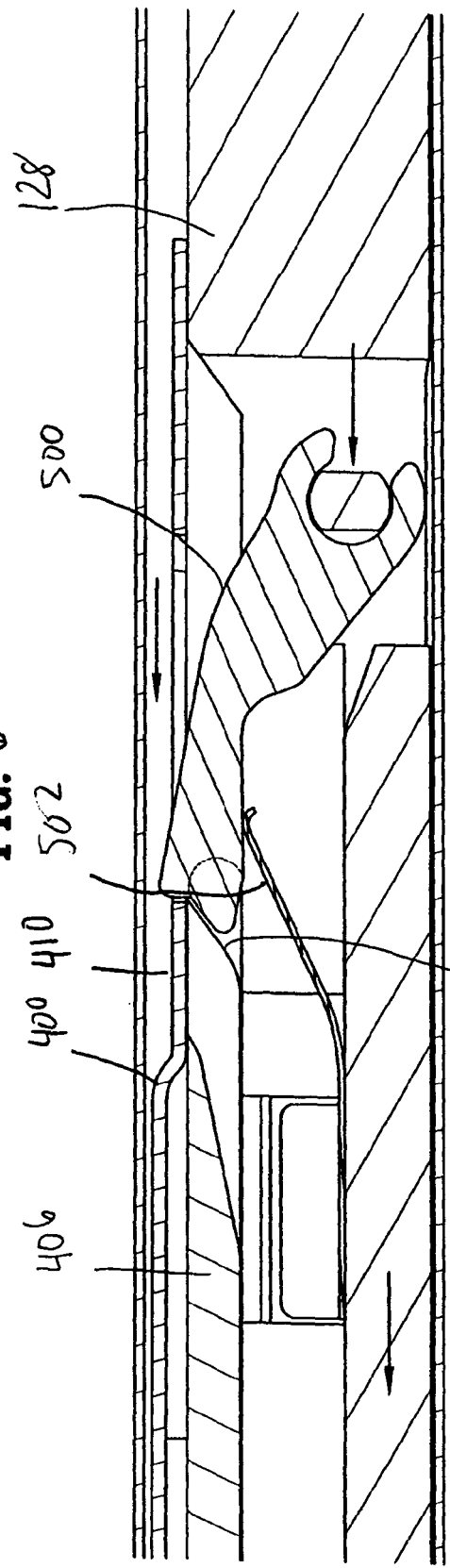
FIG. 62
FIG. 63

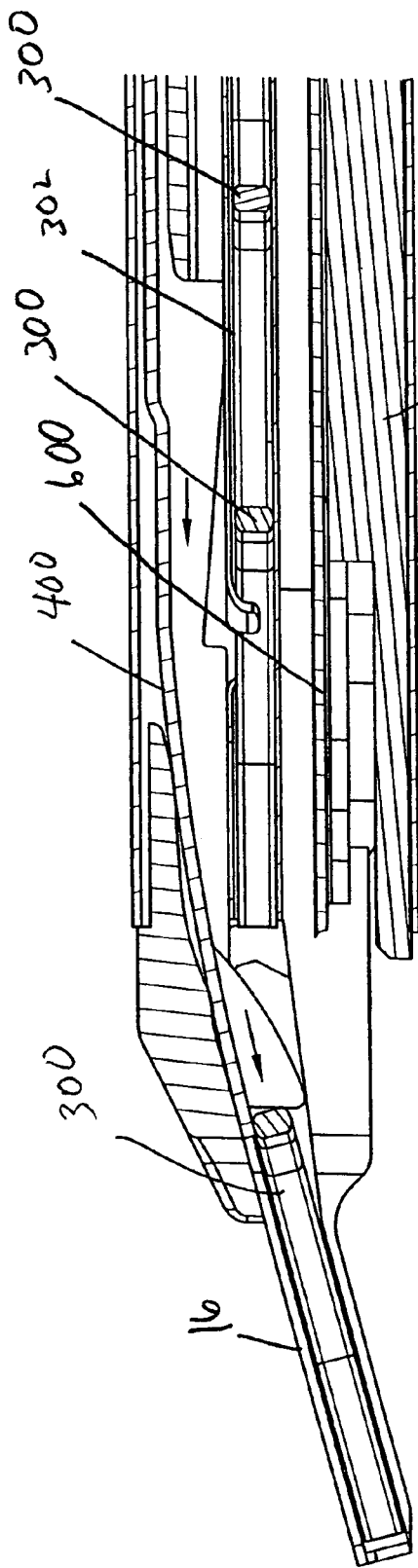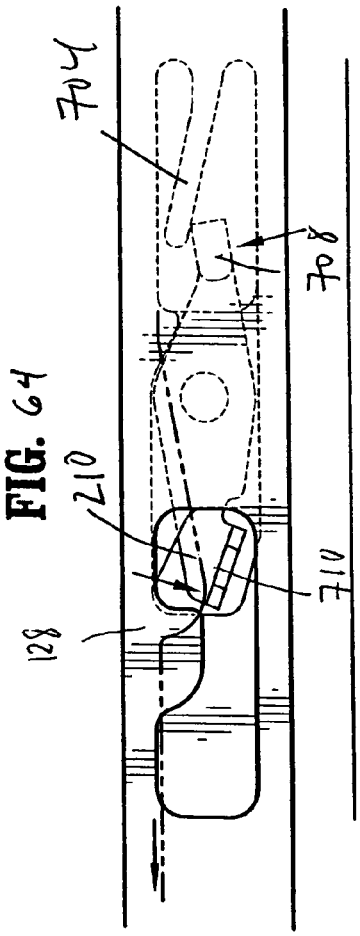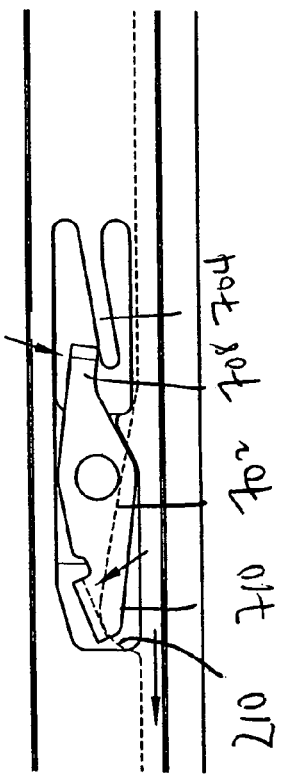

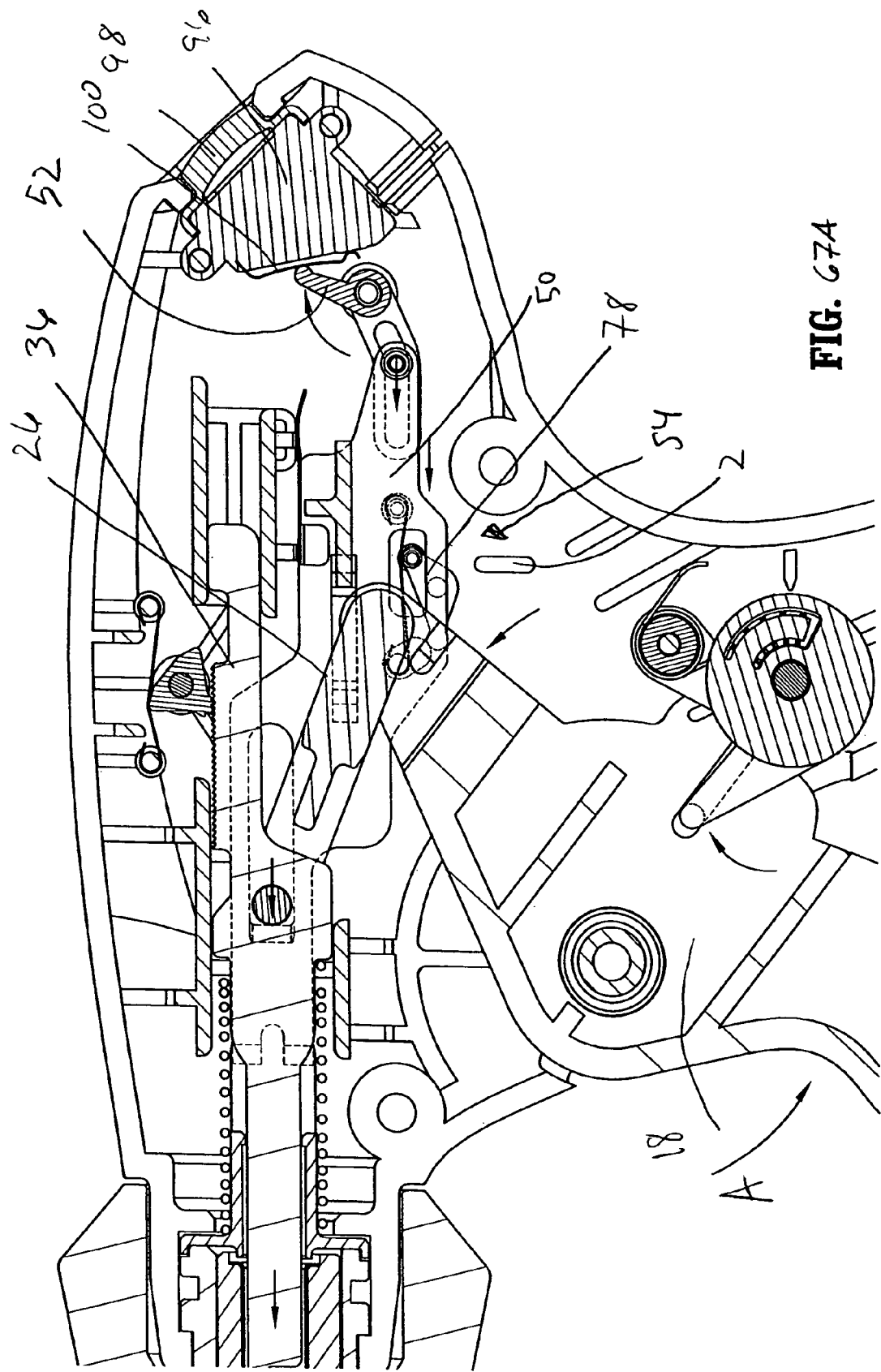

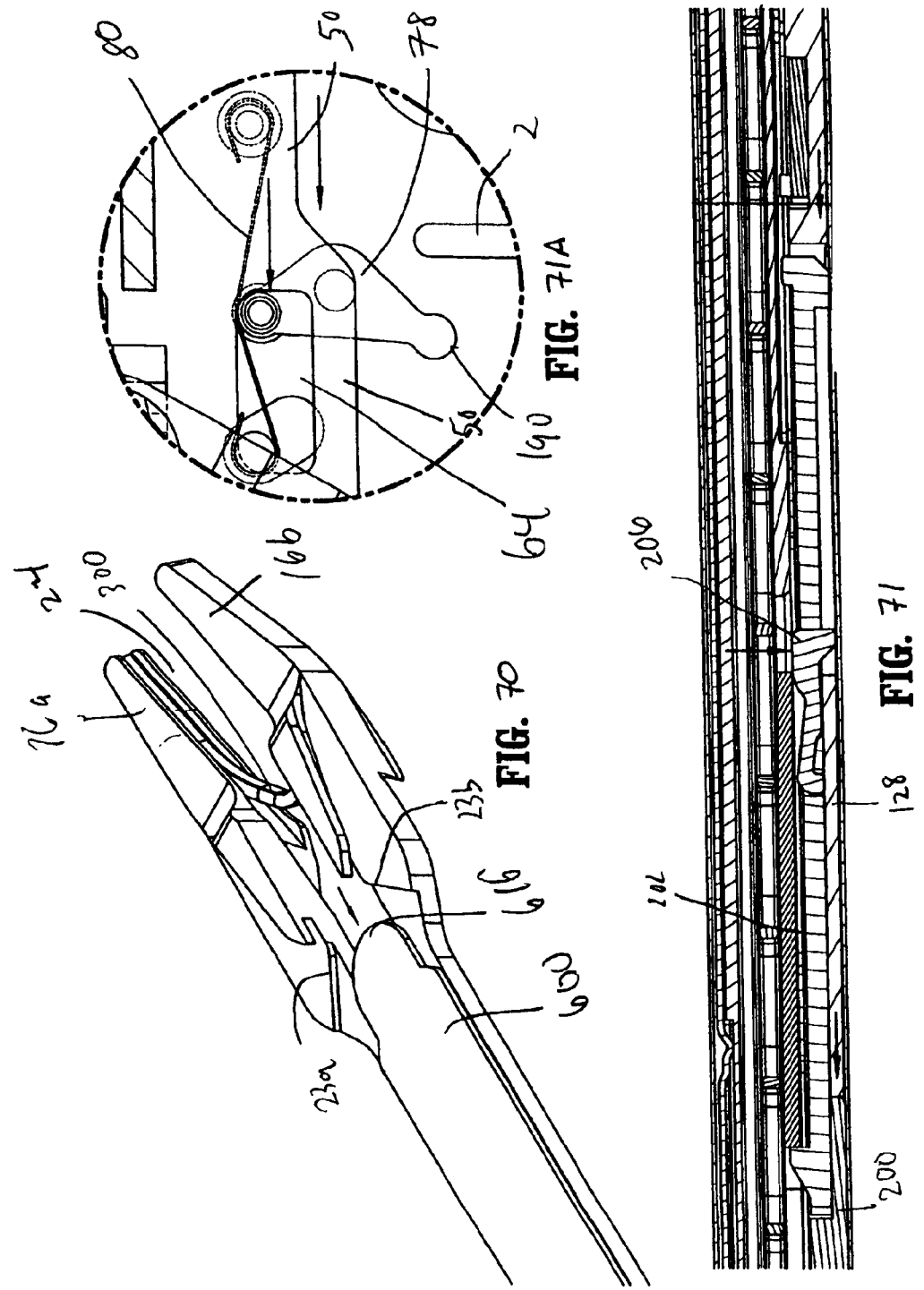

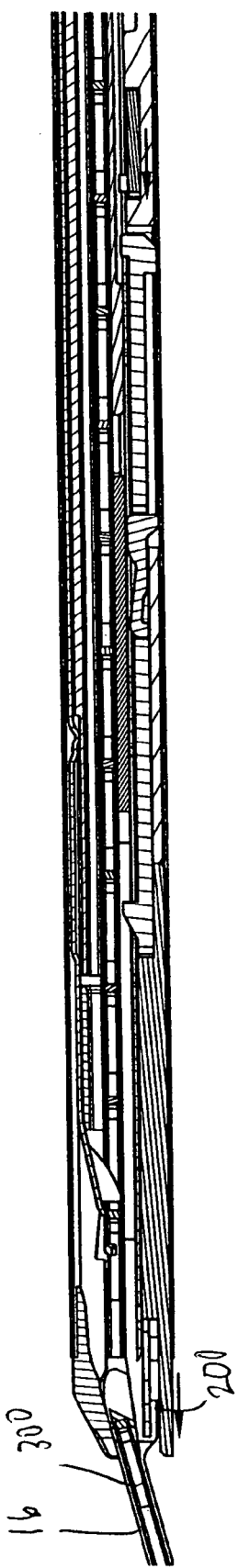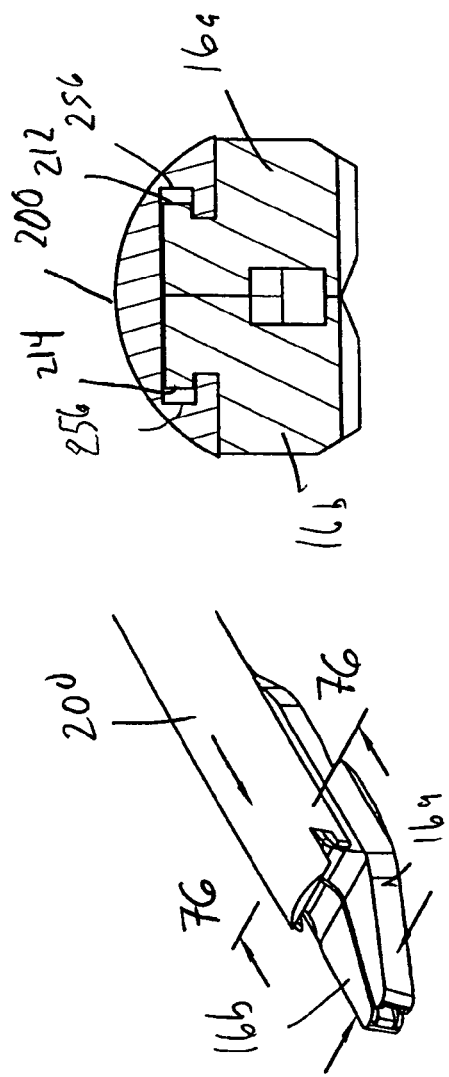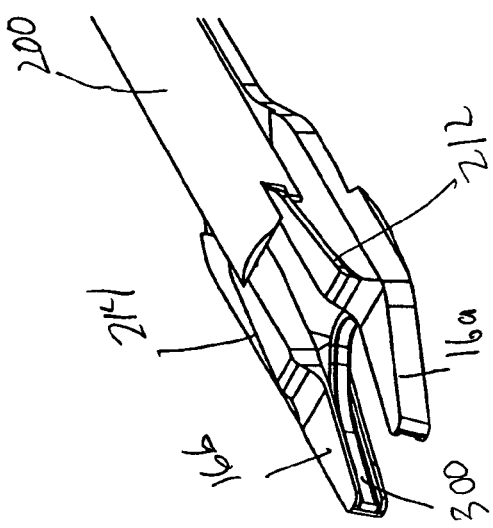

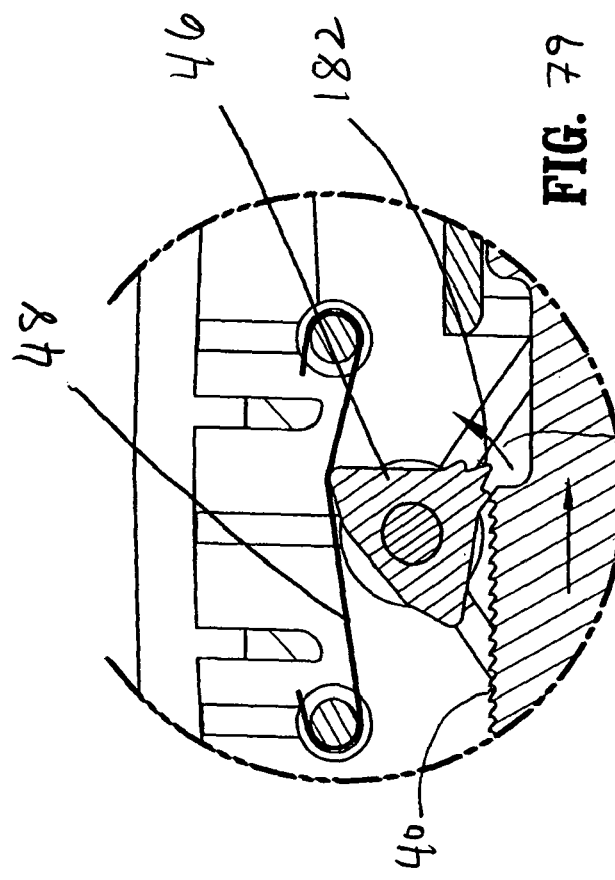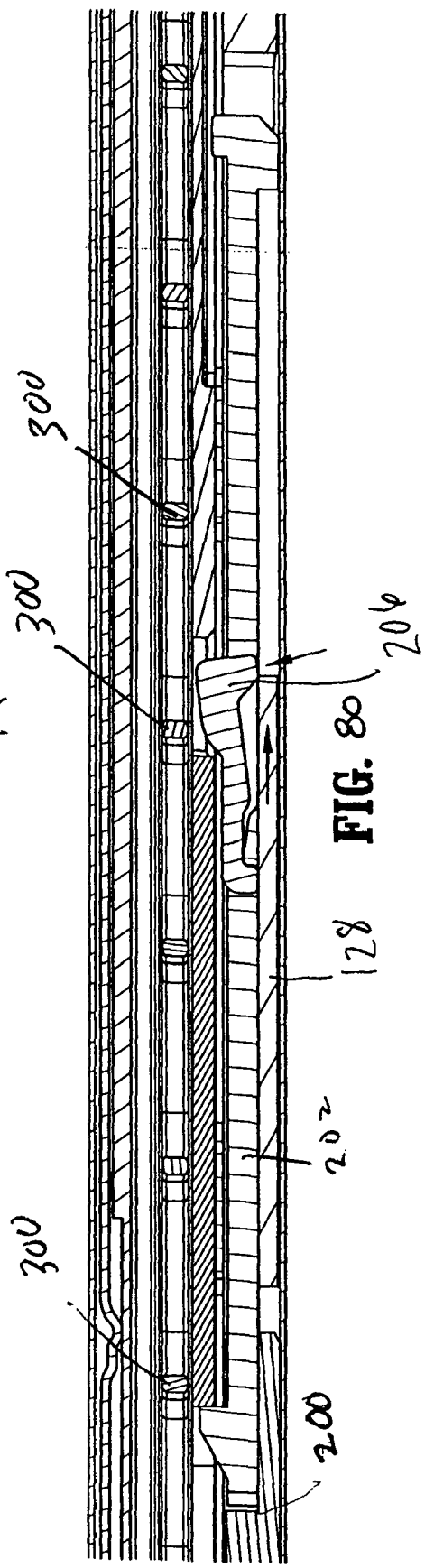

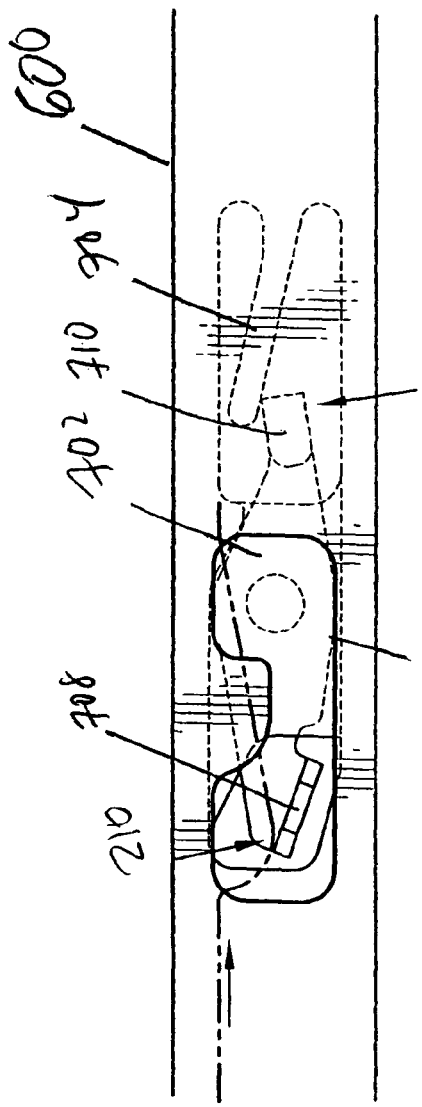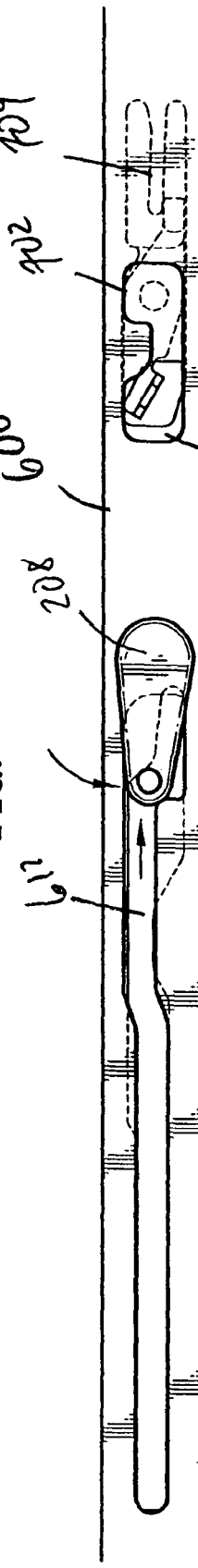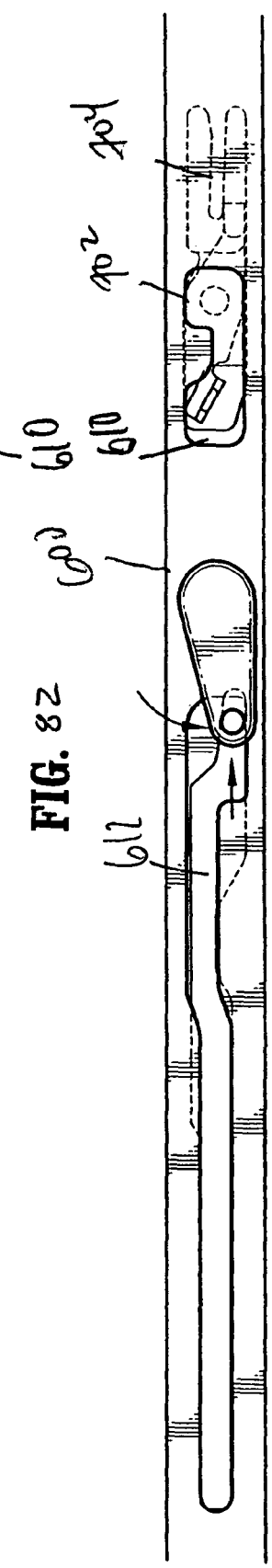
FIG. 81
FIG. 82
FIG. 83

ENDOSCOPIC SURGICAL CLIP APPLIER

CROSS REFERENCE TO RELATED PATENT APPLICATIONS

The instant patent application is a continuation-in-part of U.S. patent application Ser. No. 11/245,523 filed on Oct. 7, 2005 now U.S. Pat. No. 7,637,917 which claims priority to U.S. Provisional Patent Application Ser. No. 60/617,104 filed on Oct. 8, 2004 and U.S. Provisional Patent Application Ser. No. 60/617,016 filed on Oct. 8, 2004 which are all herein incorporated by reference in their entirety.

BACKGROUND

1. Technical Field

The present disclosure relates to a surgical clip applier. More particularly, the present disclosure relates to a surgical clip applier having a mechanism for stabilizing a jaw structure of the surgical clip applier and also having a mechanism to prevent firing the surgical clip applier when the surgical clip applier has exhausted the amount of stored clips to prevent a dry firing of the surgical clip applier.

2. Background of Related Art

Laparoscopic procedures are performed in the interior of the abdomen. The procedures are through a small incision and through a narrow endoscopic tube or cannula inserted through a small entrance incision in the skin. Minimally invasive procedures performed elsewhere in the body are often generally referred to as "endoscopic" procedures. The surgeon will insert and extend a tube or cannula device in the body through the entrance incision to provide an access port. This port allows insertion of various surgical instruments therethrough.

These instruments such as the instant clip applier are used for performing surgical procedures on organs, blood vessels, ducts, or body tissue far removed from the incision. Often during these procedures, it is necessary to apply hemostatic clips to blood vessels or various ducts to prevent the flow of body fluids therethrough during the procedure. Many different hemostatic clips having different geometries may be used and all are within the scope of the present disclosure.

One advantage of minimally invasive surgical procedures is the reduction of trauma to the patient as a result of accessing internal organs through smaller incisions. Known endoscopic clip appliers have greatly facilitated the advent of more advanced minimally invasive procedures by permitting a number of clip applications during a single entry into the body cavity. Commercially available endoscopic clip appliers are generally of 10 mm outer diameter and are adapted to be introduced through a 10 mm cannula. Other commercially available endoscopic clip appliers may also be generally of 5 mm outer diameter and are adapted to be introduced through a 5 mm cannula.

As minimally invasive procedures continue to evolve and the advantages thereof are extended to additional clinical applications, it has become desirable to further reduce incision size(s) and therefore the size of all instrumentation introduced therethrough.

The structure of surgical instruments intended to perform numerous functions within a confined space is necessarily complex. The assembly process for these instruments is often complicated and may involve numerous relatively small parts to perform the numerous functions with repeatability. It is therefore desirable to maximize the ease with which such instruments may be assembled. It is also desirable to provide an endoscopic clip applier having a structure that minimizes torque on the jaws and to facilitate the easy application of surgical homeostatic clips while further minimizing the required incision size at the surgical site. It is also desirable to provide an endoscopic clip applier having a structure that prevents the surgeon from firing the clip applier (and locks the handle) when there are no more remaining hemostatic clips in the clip applier. It is also further desirable to provide an endoscopic clip applier having a structure that provides the surgeon with multiple redundant signals that the clip applier has fired and applied the clip.

SUMMARY

It is an object of the present disclosure to provide a surgical clip applier that prevents a dry firing of the surgical clip applier when there are no remaining clips and that cannot fire when there are no remaining clips.

It is a further object of the present disclosure to provide a surgical clip applier that signals a surgeon when a clip has fired.

It is still another object of the present disclosure to provide a surgical clip applier that visually signals a surgeon when a clip has fired.

It is yet another object of the present disclosure to provide a surgical clip applier that has an elongated knob to allow a surgeon to rotate the elongated knob to rotate the endoscopic portion using only an index finger.

It is still yet another object of the present disclosure to provide a surgical clip applier that has a driver lockout mechanism that is easy to manufacture.

According to a first aspect of the present disclosure, there is provided a surgical clip applying apparatus with a handle portion, a body extending distally from the handle portion defining a longitudinal axis and a number of surgical clips disposed within the body. The apparatus has a movable member biased in the housing adjacent the wedge plate. An actuator longitudinally advances the wedge plate a predetermined distance to a distal most position. The wedge plate has an end being disposed between first and second jaw portions at the distal most position. The wedge plate end is configured to maintain the jaw assembly in the spaced apart position during loading of the surgical clip and the wedge plate end reduces torque on the jaw assembly during the loading. The movable member holds the wedge plate in the distal most position during the loading and the movable member is deflected at a conclusion of the loading. The movable member releases the wedge plate upon deflection and the rotatable member allowing a longitudinal proximal retraction of the wedge plate from the distal most position.

According to another aspect of the present disclosure, there is provided an apparatus for application of surgical clips to body tissue. The apparatus has a handle assembly with a handle and a trigger movable relative to the handle. The trigger has a trigger lockout notch. The apparatus also has a body extending distally from the handle portion and defining a longitudinal axis and a plurality of surgical clips disposed within the body and a jaw assembly mounted adjacent a distal end portion of the body with the jaw assembly including first and second jaw portions movable between a spaced apart and an approximated position.

The apparatus also has a clip pusher configured to individually distally advance a surgical clip to the jaw assembly while the jaw portions are in the spaced apart position. The apparatus also further has an actuator at least partially disposed within the body and longitudinally movable in response to actuation of the handle portion.

The apparatus further has a lockout mechanism with a first rotatable member with a first shaft and a first arm having a first pawl. The first shaft fixedly engages the handle portion and the mechanism has a second rotatable member with an escape notch on a radial position of the second rotatable member with a second post, and a plurality of teeth disposed around substantially an inner circumference of an inner surface of the second rotatable member. The mechanism has a third rotatable member with an aperture for receiving the second post and the third rotatable member is configured to engage with the trigger.

The pawl rotates in the inner surface of the second rotatable member to mesh with the teeth and the pawl advances to a next tooth of the plurality of teeth when the trigger is fired. The teeth are complementary in number to the remaining clips and when the clips are exhausted the pawl is advanced to the escape notch. If the trigger is fired and the clips are exhausted, the first pawl traverses out from the second rotatable member to the trigger notch. The pawl mates with the trigger notch to prevent firing.

According to still another aspect of the present disclosure there is provided an apparatus for application of surgical clips to body tissue comprising a handle portion and a body extending distally from the handle portion and defining a longitudinal axis. The apparatus also has a plurality of surgical clips disposed within the body and a jaw assembly mounted adjacent a distal end portion of the body. The jaw assembly further comprises first and second jaw portions movable between a spaced apart and an approximated position. The apparatus has a wedge plate longitudinally movable between the first and the second jaw portions and a clip pusher configured to individually distally advance a surgical clip to the jaw assembly while the jaw portions are in the spaced apart position.

The apparatus also has an actuator at least partially disposed within the body and longitudinally movable in response to actuation of the handle portion, and a jaw closure member positioned adjacent the first and the second jaw portions to move the jaw portions to the approximated position. The actuator longitudinally advances the wedge plate a predetermined distance to a distal most position. The wedge plate has an end being disposed between the first and the second jaw portions at the distal most position. The wedge plate end is configured to maintain the jaw assembly in the spaced apart position during loading of the surgical clip. The end reduces torque on the jaw assembly during the loading and the actuator further actuates a signal device. The signal device indicates that at least one of the clips has fired.

According to yet another aspect of the present disclosure there is provided an apparatus for application of surgical clips to body tissue. The apparatus has a handle portion, and a body extending distally from the handle portion and defining a longitudinal axis. The apparatus has surgical clips disposed within the body and a jaw assembly mounted adjacent a distal end portion of the body with the jaw assembly further comprising first and second jaw portions movable between a spaced apart and an approximated position. The apparatus has a wedge plate longitudinally movable between the first and the second jaw portions and a clip pusher configured to individually distally advance a surgical clip to the jaw assembly while the jaw portions are in the spaced apart position. The apparatus also has an actuator at least partially disposed within the body and longitudinally movable in response to actuation of the handle portion. The apparatus further has a jaw closure member positioned adjacent the first and the second jaw portions to move the jaw portions to the approximated position. The actuator longitudinally advances the wedge plate a predetermined distance to a distal most position and the wedge plate has an end being disposed between the first and the second jaw portions at the distal most position.

The wedge plate end is configured to maintain the jaw assembly in the spaced apart position during loading of the surgical clip. The end reduces torque on the jaw assembly during loading. The actuator further actuates an audible device configured to indicate that at least one of the clips has fired.

According to still yet another aspect there is provided an apparatus for application of surgical clips to body tissue. The apparatus has a handle portion, a body extending distally from the handle portion and defining a longitudinal axis, and a plurality of surgical clips disposed within the body. The apparatus also has a jaw assembly mounted adjacent a distal end portion of the body with the jaw assembly further comprising first and second jaw portions movable between a spaced-apart and an approximated position. The apparatus also has a wedge plate longitudinally movable between the first and the second jaw portions, and a clip pusher configured to individually distally advance a surgical clip to the jaw assembly while the jaw portions are in the spaced apart position. The apparatus also has an actuator at least partially disposed within the body and longitudinally movable in response to actuation of the handle portion, and a jaw closure member positioned adjacent the first and the second jaw portions to move the jaw portions to the approximated position. The actuator longitudinally advances the wedge plate a predetermined distance to a distal most position, and the wedge plate has an end being disposed between the first and the second jaw portions at the distal most position. The wedge plate end is configured to maintain the jaw assembly in the spaced apart position during loading of the surgical clip. The wedge plate end reduces torque on the jaw assembly during loading. The apparatus further has the body connected to the handle by a rotatable member. The rotatable member is fixedly connected to the handle and the body. Upon rotation of the rotatable member the body rotates and the jaw portions rotate. The rotatable member is a plurality of members having a first elongated knob housing and a second knob with a plurality of notches being disposed therearound. The second knob is disposed over the knob housing. At least one of the members is adapted to be rotated by an index finger for rotating the body.

According to yet another aspect of the present disclosure there is provided an apparatus for application of surgical clips to body tissue. The apparatus has a handle portion and a body extending distally from the handle portion and defining a longitudinal axis. The apparatus also has a plurality of surgical clips disposed within the body and a jaw assembly mounted adjacent a distal end portion of the body. The jaw assembly includes first and second jaw portions movable between a spaced apart and an approximated position. The apparatus also has a feed bar configured to individually distally advance a surgical clip to the jaw assembly while the jaw portions are in the spaced apart position. The apparatus further has a clip pusher disposed proximal to the plurality of clips and configured to bias the plurality of clips in a distal manner with an actuator at least partially disposed within the body and longitudinally movable in response to actuation of the handle portion. The apparatus also has a jaw closure member positioned adjacent the first and second jaw portions to move the jaw portions to the approximated position and a rack having a plurality of ratchet teeth being connected to the actuator. A pawl with at least one tooth is configured to engage the ratchet teeth. The pawl is biased in the handle portion. As the actuator is moved longitudinally the plurality of ratchet teeth are passed over the pawl. The pawl is configured to prevent an inadvertent return of the actuator before full actuation of the apparatus.

The apparatus also has a bar being disposed in proximity to the feed bar. The bar is biased by a spring and lodged between a ceiling and a floor of the clip carrying channel. The clip carrying channel includes a distal window. As the clip pusher moves distally each time a clip is released from the apparatus the clip pusher moves the bar distally. When the bar is in substantial alignment with the distal window, the bar moves through the distal window to deflect the feed bar to a second position. The feed bar in the second position prevents the actuator from moving proximally and thereby manipulates the pawl to be engaged with the ratchet teeth of the rack. The pawl and rack prevent the actuator from longitudinally moving.

An apparatus for application of surgical clips to body tissue includes a handle portion and a body extending distally from the handle portion and defining a longitudinal axis. The apparatus also has a plurality of surgical clips disposed within the body and a jaw assembly mounted adjacent a distal end portion of the body. The jaw assembly includes first and second jaw portions movable between a spaced apart and an approximated position. The apparatus also includes a feed bar configured to individually distally advance a surgical clip to the jaw assembly while the jaw portions are in the spaced apart position. The feed bar includes at least one proximal fin.

The apparatus also has a clip pusher disposed proximal to the plurality of clips and configured to bias the plurality of clips in a distal manner. The apparatus also has an actuator at least partially disposed within the body and longitudinally movable in response to actuation of the handle portion. The actuator includes a proximal window. A jaw closure member is positioned adjacent the first and second jaw portions to move the jaw portions to the approximated position. A rack having a plurality of ratchet teeth is connected to the actuator. The apparatus also includes a pawl having at least one tooth configured to engage the ratchet teeth with the pawl biased in the handle portion.

As the actuator is moved longitudinally, the ratchet teeth are passed over the pawl. The pawl is configured to prevent inadvertent return of the actuator before full actuation of the apparatus. The apparatus also has a bar disposed in proximity to the feed bar. The bar is biased by a spring and lodged between a ceiling and a floor of a clip carrying channel.

The clip carrying channel includes a distal window. As the clip pusher moves distally each time a clip is released from the apparatus, the clip pusher moves the bar distally. When the bar is in substantial alignment with the distal window, the bar that is biased by the spring moves through the distal window to deflect the feed bar to a second position.

The feed bar in the second position includes the proximal fin in engagement with the proximal window of the actuator. The engagement of the feed bar and the actuator prevents retraction but not advancement of the actuator and thereby manipulates the pawl to be engaged with the rack in a substantially intermediate position. The pawl and rack prevent the actuator from moving longitudinally to thereby lock the actuator.

An apparatus for application of surgical clips to body tissue includes a clip pusher that incrementally moves distally each time a clip is released from the apparatus. When the clip pusher reaches a predetermined distal point in the clip carrying channel, the feed bar is deflected to a second position. The feed bar in the second position has a portion that is in engagement with the actuator.

The feed bar in the second deflected position prevents retraction but not advancement of the actuator and thereby manipulates the pawl to be engaged with ratchet teeth of the rack. The pawl and rack prevent the actuator from moving longitudinally to thereby lock the actuator.

BRIEF DESCRIPTION OF THE DRAWINGS

Various embodiments will be described herein below with reference to the drawings wherein:

FIG. 7A is a perspective view of the spindle link engaging the spindle;

FIG. 7B is a rear view of the knob with a number of components therein;

FIG. 7C is a perspective view of the knob exploded from a knob housing;

FIG. 7D is a perspective view of the outer tubular member having a notch;

FIG. 7E is a perspective view of the outer tubular member with a bushing;

FIG. 7F is a rear view of the knob connected to the knob housing and bushing of FIG. 7E;

FIG. 8 is a perspective view of a pawl;

FIG. 9 is a perspective view of a driving member;

FIG. 9A is a perspective view of an actuator plate;

FIG. 9B is a perspective view of a signaling device;

FIG. 9C is a perspective view of a LCD lever;

FIG. 9D is a perspective view of a wishbone link;

FIG. 10A is a perspective view of a feed bar;

FIG. 10B is a perspective view of a follower and surgical clips;

FIGS. 10C and 10D are opposite perspective views of a trip block;

FIG. 10E is a perspective view of a spindle;

FIG. 10F is an enlarged area of detail of FIG. 10E;

FIG. 10G is an enlarged area of detail of FIG. 10E;

FIG. 11 is a perspective view of the distal end of the spindle and a driver;

FIG. 12 is a perspective view of a trip lever with the trip lever spring on the spindle;

FIG. 13 is a perspective view of a wedge plate;

FIG. 13A is a perspective view of a "C" shaped window on the wedge plate of FIG. 13;

FIGS. 14 and 15 are opposite perspective views of a filler component;

FIG. 14A is an exploded view of a rotatable member being above a spring bar member in the filler component;

FIG. 16 is a perspective view of the rotation assembly;

FIG. 17 is a perspective view of the overpressure assembly;

FIG. 18 is a perspective view of the spindle and jaw assembly;

FIG. 19 is an enlarged area of detail of the spindle and jaw assembly of FIG. 18 with a feed bar and a pusher connected to the feed bar;

FIG. 20 is an enlarged area of detail of FIG. 18;

FIG. 21 is an enlarged view of the distal end of the surgical clip applier with outer member removed;

FIG. 22 is a perspective view of the surgical clip applier with parts removed showing a clip channel member and a follower biasing a number of clips;

FIG. 23 is an enlarged area at detail of FIG. 22;

FIG. 24 is an enlarged area of detail of FIG. 22;

FIG. 25 is an enlarged area of detail of FIG. 22;

FIG. 26 is a perspective view of the spindle, driver and jaw assembly;

FIG. 27 is an enlarged area of detail of FIG. 26;

FIG. 28 is a perspective view of the cam link and wedge plate assembly;

FIG. 29 is an enlarged area of detail of FIG. 28;

FIG. 30 is an enlarged area of detail of FIG. 29;

FIG. 31 is a perspective view of the filler component and jaw assembly;

FIG. 32 is an enlarged perspective view of the jaw assembly of FIG. 31;

FIGS. 33 and 34 are perspective views of the distal end of the spindle including wedge plate and driver with the wedge plate removed in FIG. 33;

FIG. 37 is an enlarged area of detail of FIG. 35;

FIG. 38 is in enlarged area of detail of FIG. 37 showing the trip lever;

FIG. 41 is an enlarged area of detail of FIG. 40;

FIG. 41A is a top view of the filler component with the rotatable member engaging the spring bar member;

FIG. 41B is a cross sectional view of the distal end of the surgical clip applier along line 41B-41B of FIG. 41;

FIG. 42 is a side view, shown in section, of the distal end of the surgical clip applier of FIG. 37 with the feed bar engaging a clip;

FIG. 42A is an enlarged area of detail of FIG. 42;

FIG. 43 is a perspective view of the wedge plate and jaw assembly;

FIG. 44 is an enlarged area of detail of FIG. 43;

FIG. 45 is a top view of FIG. 43 taken along line 45-45;

FIG. 46 is an enlarged area of detail of FIG. 45 showing the jaw and the wedge plate;

FIG. 47 is an enlarged area of detail of FIG. 45 showing the wedge plate and cam link;

FIG. 48 is a side view, shown in section, of the handle housing at the beginning of an initial stroke;

FIG. 49 is an enlarged area of detail of FIG. 48 showing the rack and pawl;

FIG. 49A is an enlarged area of detail of FIG. 48 showing the audible click lever and rib;

FIG. 50 is an enlarged area of detail of FIG. 48 similar to FIG. 49;

FIG. 50A is an enlarged area of detail of the lockout mechanism of FIG. 48;

FIG. 54 is an enlarged area of detail of FIG. 53 illustrating the spindle movement;

FIG. 55 is a top view of the wedge plate and filler component illustrating the movement of the cam link in the cam slot;

FIG. 56 is a side view, shown in section, illustrating the feed bar advancing a clip;

FIG. 57 is a top view of the wedge plate and cam link moving distally and the wedge plate moving relative to the follower with the rotatable member rotating and contacting the spring bar member;

FIG. 58 is a side view, shown in section, illustrating a clip entering the jaws;

FIG. 59 is a further top view of the cam link and wedge plate movement with the camming feature of the spindle contacting the cam link;

FIG. 60 is a top view of the wedge plate entering the jaw structure;

FIG. 61 is a perspective view illustrating the rounded distal end of the wedge plate opening the jaw structure for loading;

FIG. 62 is a top view illustrating further advancement of the cam link in the cam slot of the wedge plate;

FIG. 63 is a side view, shown in section, illustrating the trip lever engaged with the feed bar;

FIG. 64 is a side view, shown in section, illustrating a clip that entered the jaws with the feed bar at a most distal position;

FIG. 65 is a top view illustrating the rotatable member in the "C" shaped window of the wedge plate;

FIG. 65A is a bottom view illustrating the rotatable member in the "C" shaped window of the wedge plate deflecting the spring bar member of the filler component;

FIG. 67A is a side view of the handle housing with the trigger at a greater stroke;

FIG. 70 is a perspective view of the wedge plate retracting from the jaw structure;

FIG. 71 is a side view, shown in section, with the spindle engaging the driver and a driver lockout member engaging the spindle;

FIG. 71A is a side view of the handle section with the click lever rotatable to contact the rib in the housing for an audible alarm;

FIG. 73 is a side view, shown in section, of the driver camming the jaws closed about a surgical clip;

FIGS. 74 to 76 are sequential views of the driver camming the jaws closed about a surgical clip;

FIG. 79 is an enlarged area of detail of the pawl resetting;

FIG. 80 is a side view, shown in section, illustrating the spindle retracting;

FIG. 81 is a top view illustrating the rotatable member of the filler component resetting;

FIGS. 82 and 83 are top views illustrating the cam link resetting within the wedge plate;

FIGS. 84 through 86 are side views illustrating the lockout mechanism rotating and the shaft portion of the first rotatable member traversing through the escape notch to engage a corresponding notch in the trigger to prevent the trigger from firing;

FIG. 87 is an exploded view of another embodiment of the clip applier with a filler component, a wedge plate, a link cam and a spindle;

FIG. 88A is a top view of the filler component resting on the wedge plate and on the spindle;

FIG. 88B is a top view of the link cam and the wedge plate resting on the spindle with the filler component removed;

FIG. 88C is a top view of the link cam and the wedge plate resting on the spindle with the cam slot of the spindle being shown in phantom lines for illustration purposes;

FIG. 89 is a close up view of the link cam engaging the wedge plate and traversing in the cam slot of the spindle along window 89 of FIG. 88C;

FIG. 90 is a perspective view of a first component of an alternative signaling device of the present clip applier;

FIG. 91 is a top view of the first component of the signaling device of FIG. 90;

FIG. 92 is a side view of the first component;

FIG. 93 is a front view of a channel of the first component;

FIG. 94 is a perspective view of a second component of the alternative signaling device of the present clip applier;

FIG. 95 is a perspective view of the handle portion of the present clip applier with a rib portion and a lateral click strip;

Figure 96:
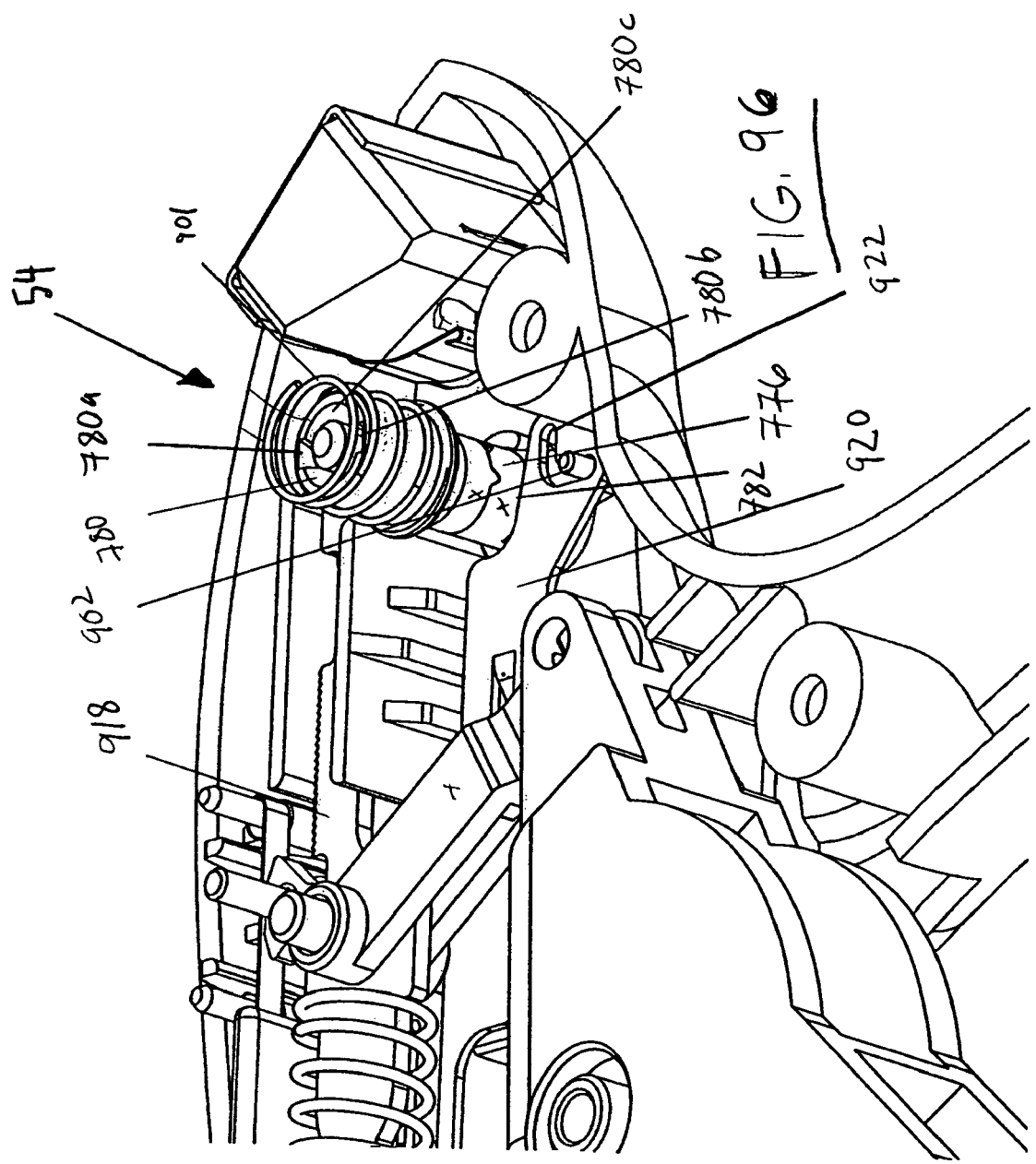
Figure 97:
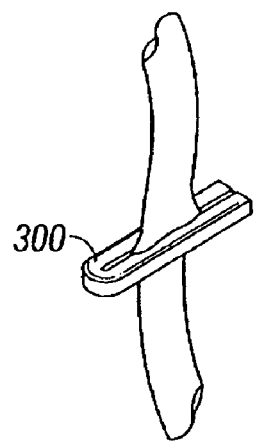
Figure 98:
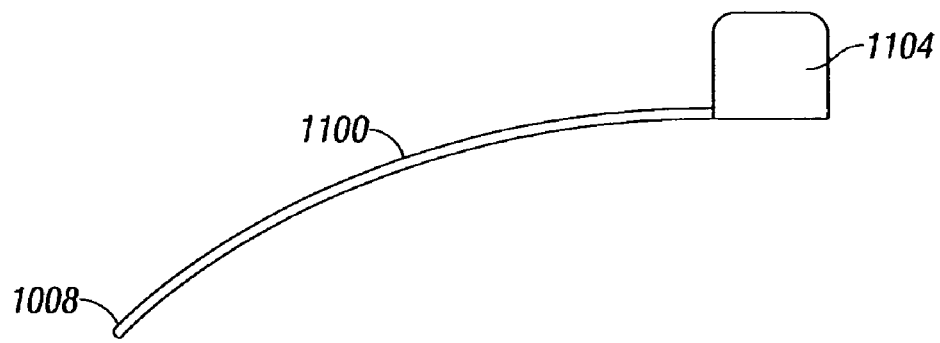
Figure 99:
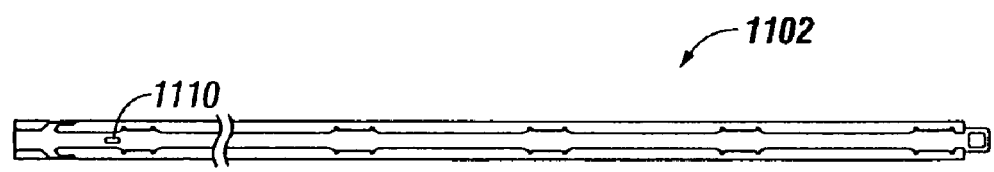
Figure 100:
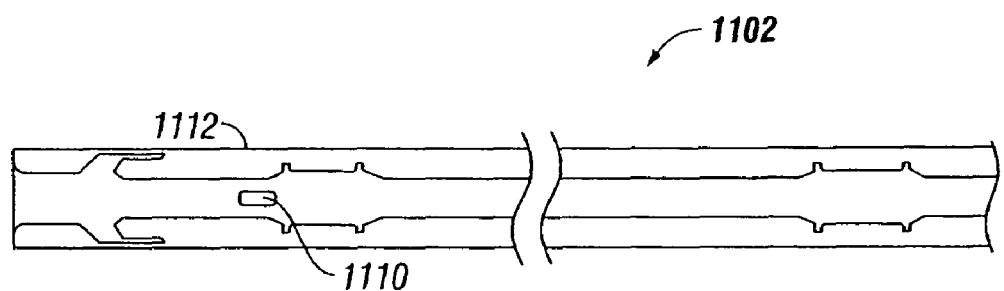
Figure 101:
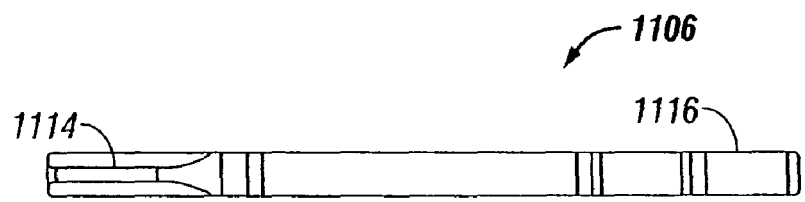
Figure 102:
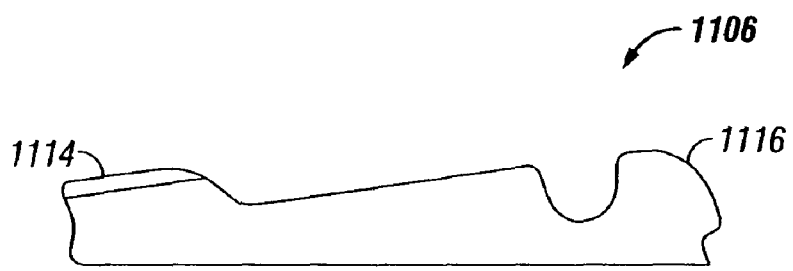
Figure 102A:
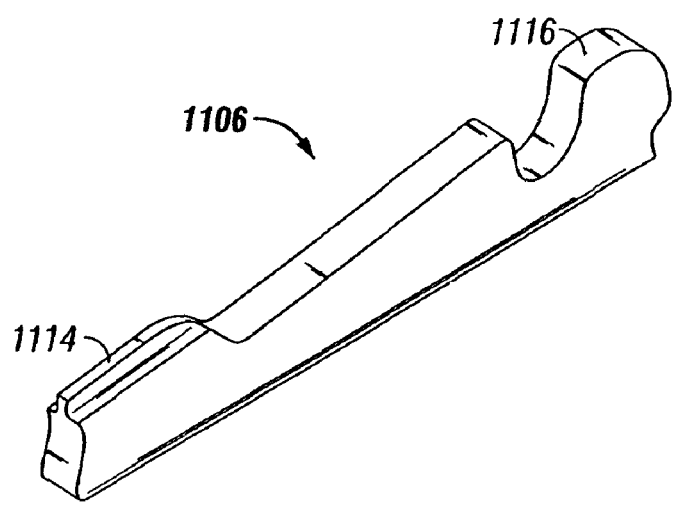
Figure 103:
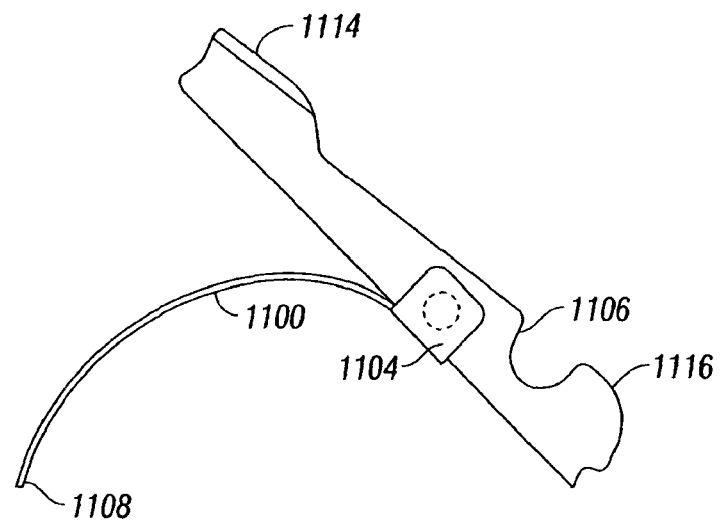
Figure 104:
Figure 105:
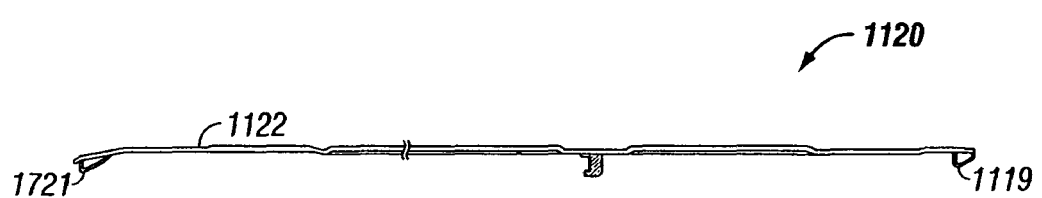
Figure 106:
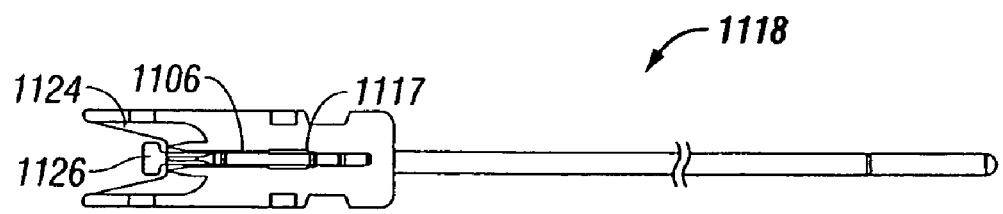
Figure 107:
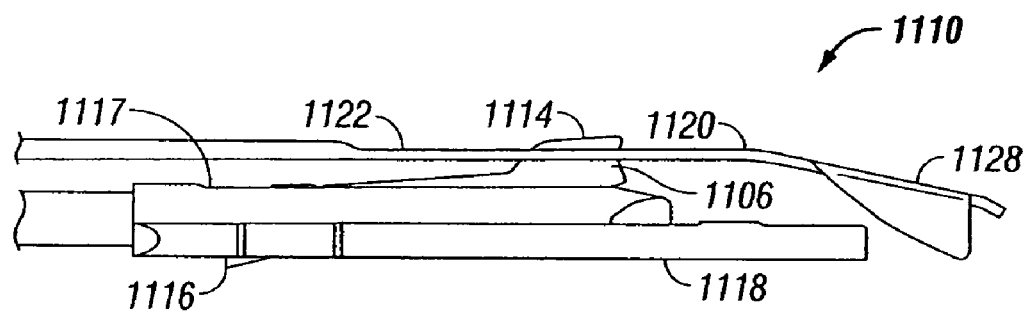
Figure 108:
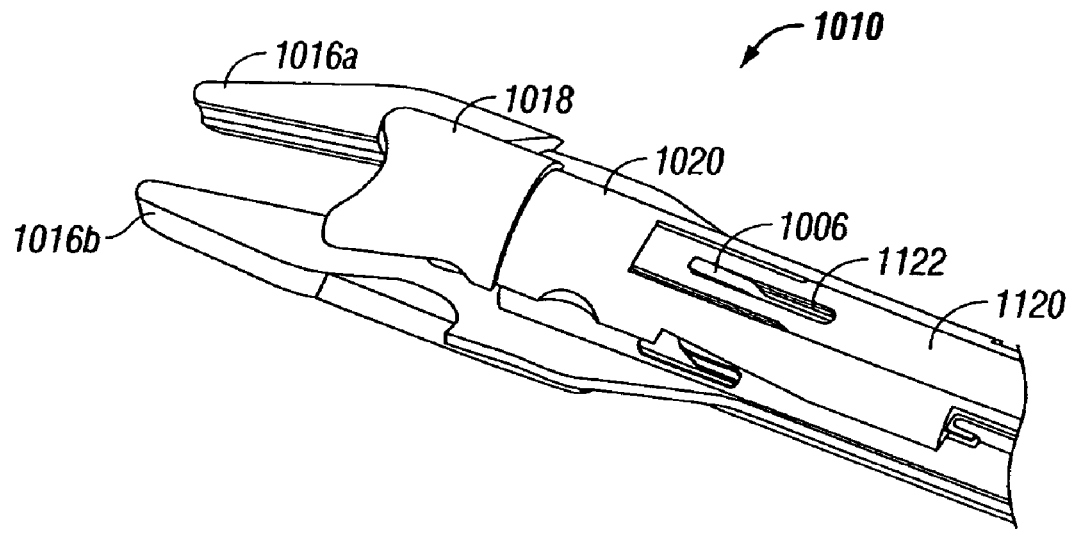
Figure 109:
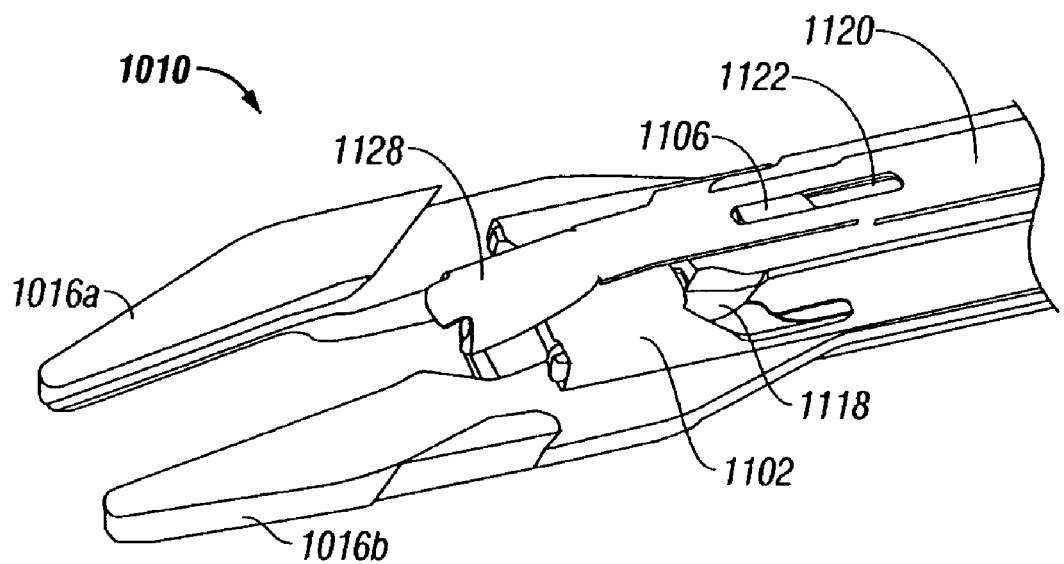
Figure 110:
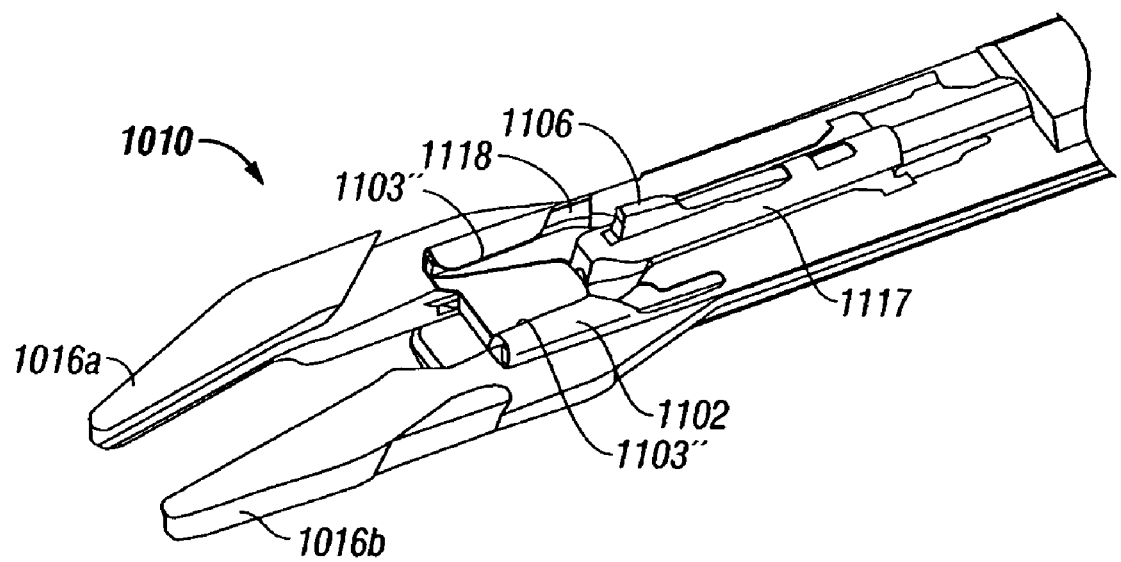
Figure 111:
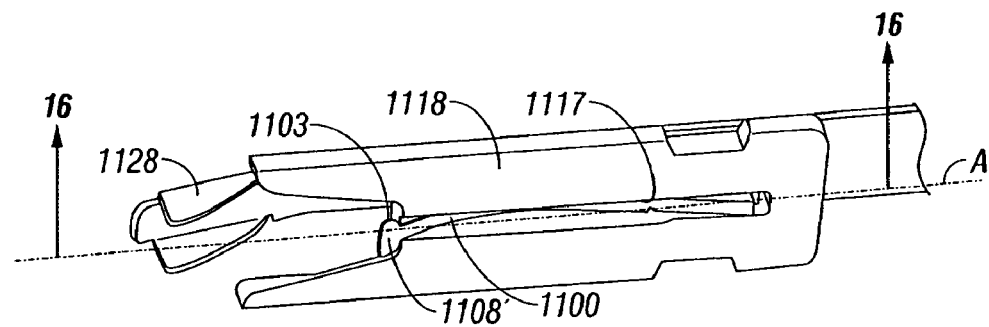
Figure 112:
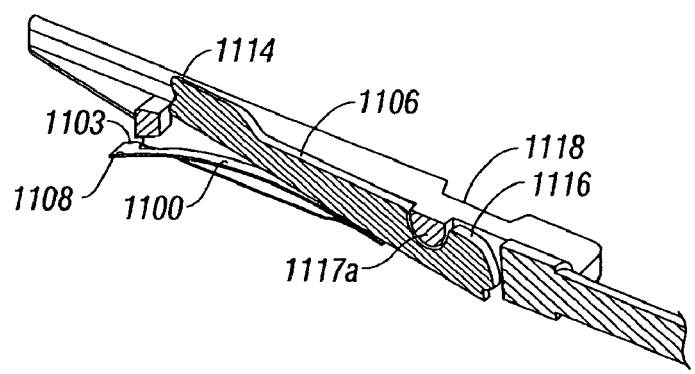
Figure 113:
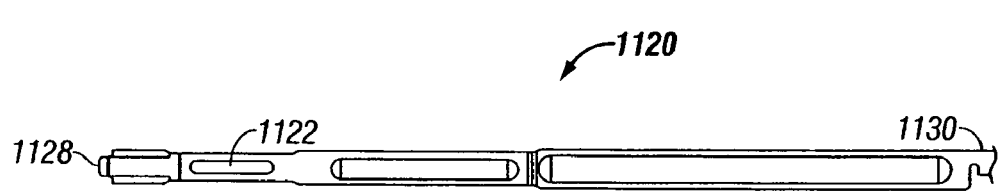
Figure 114:
Figure 114A:
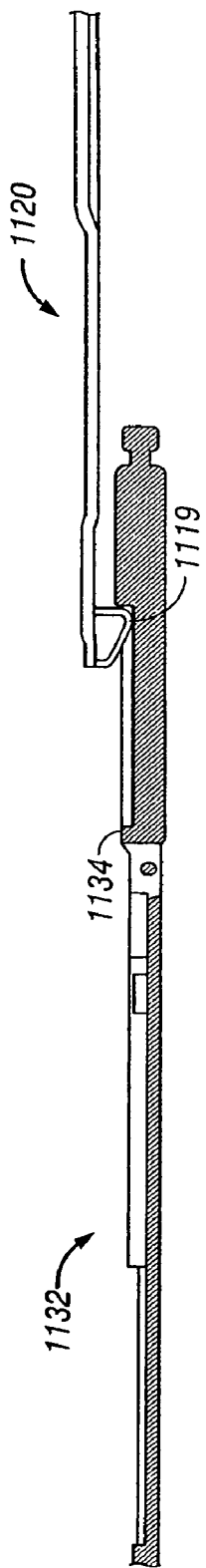
Figure 115:
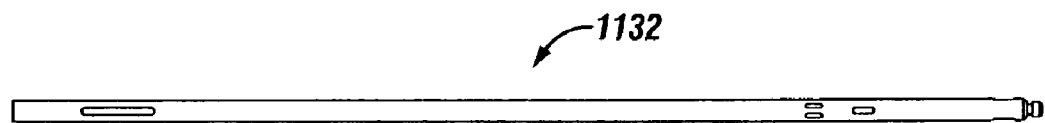
Figure 116:
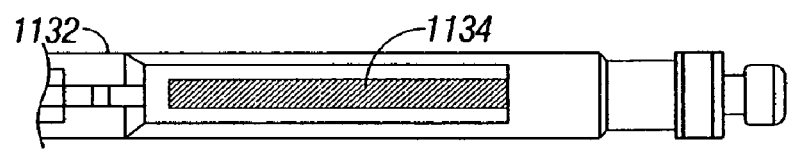
Figure 117:
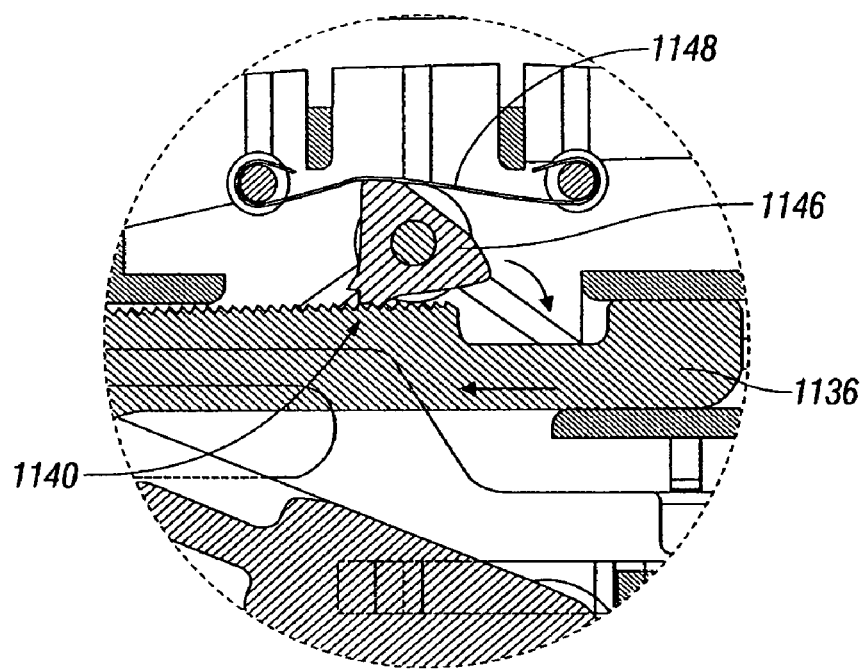
Figure 118:
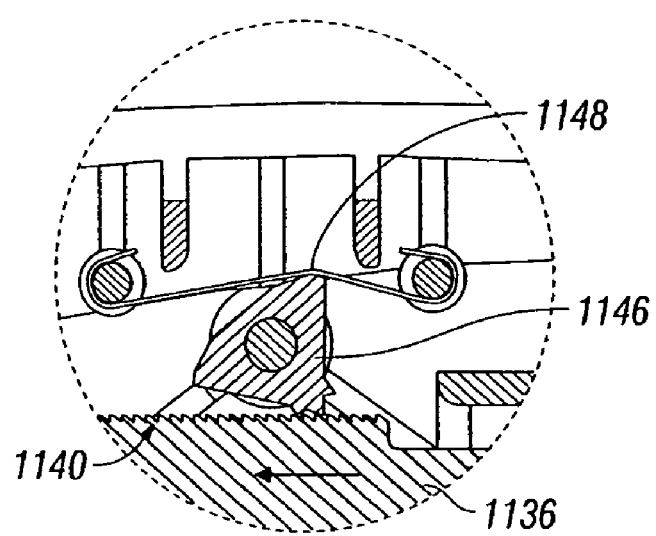
Figure 119:
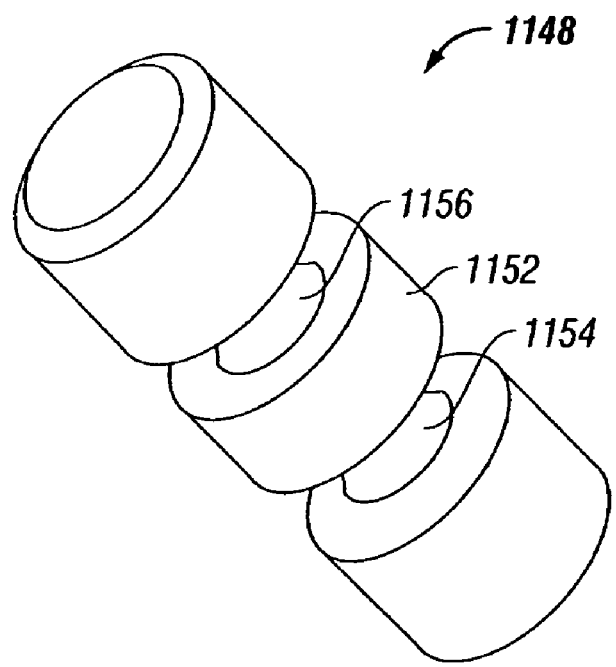
Figure 126:
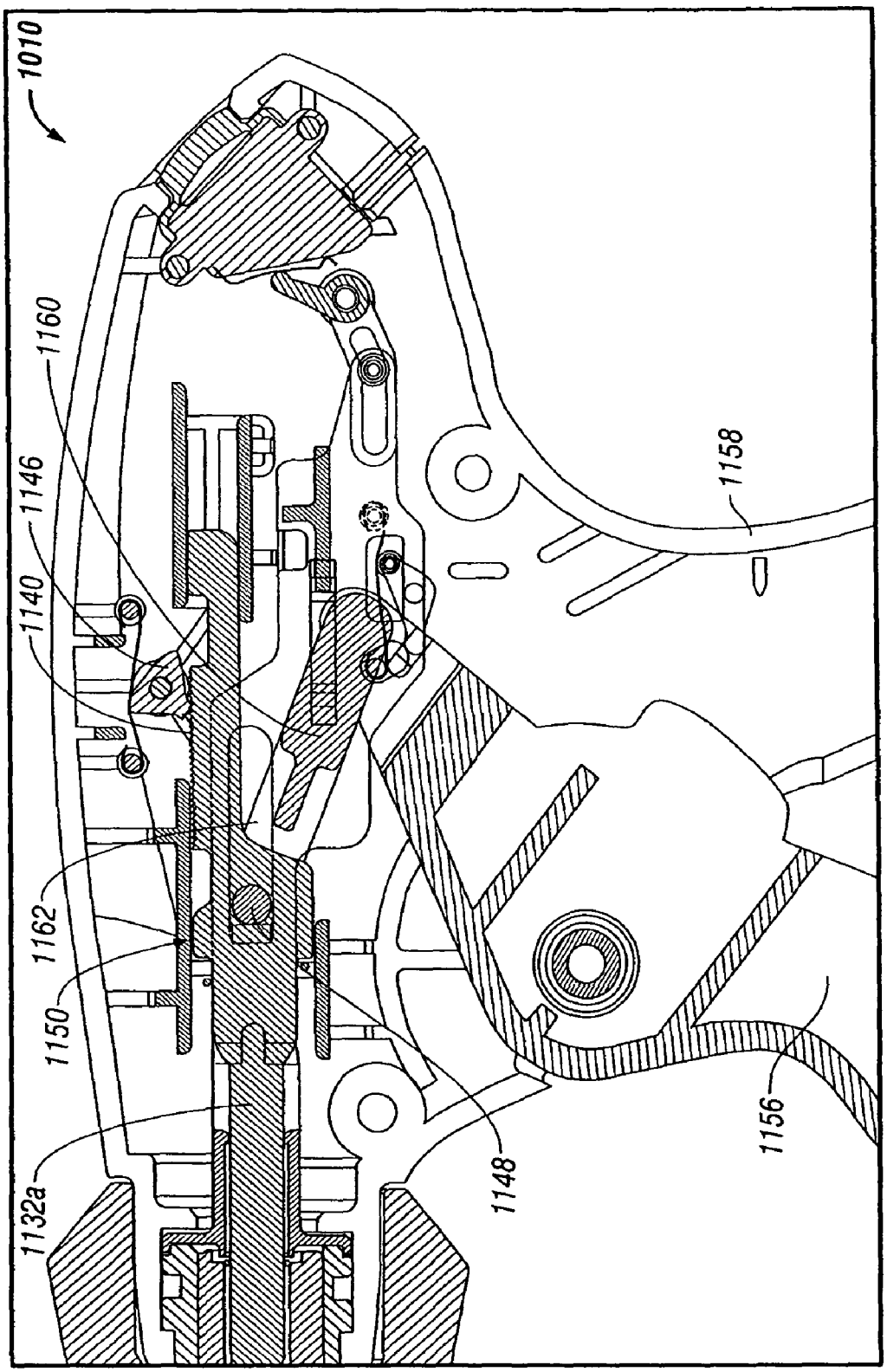
Figure 121:
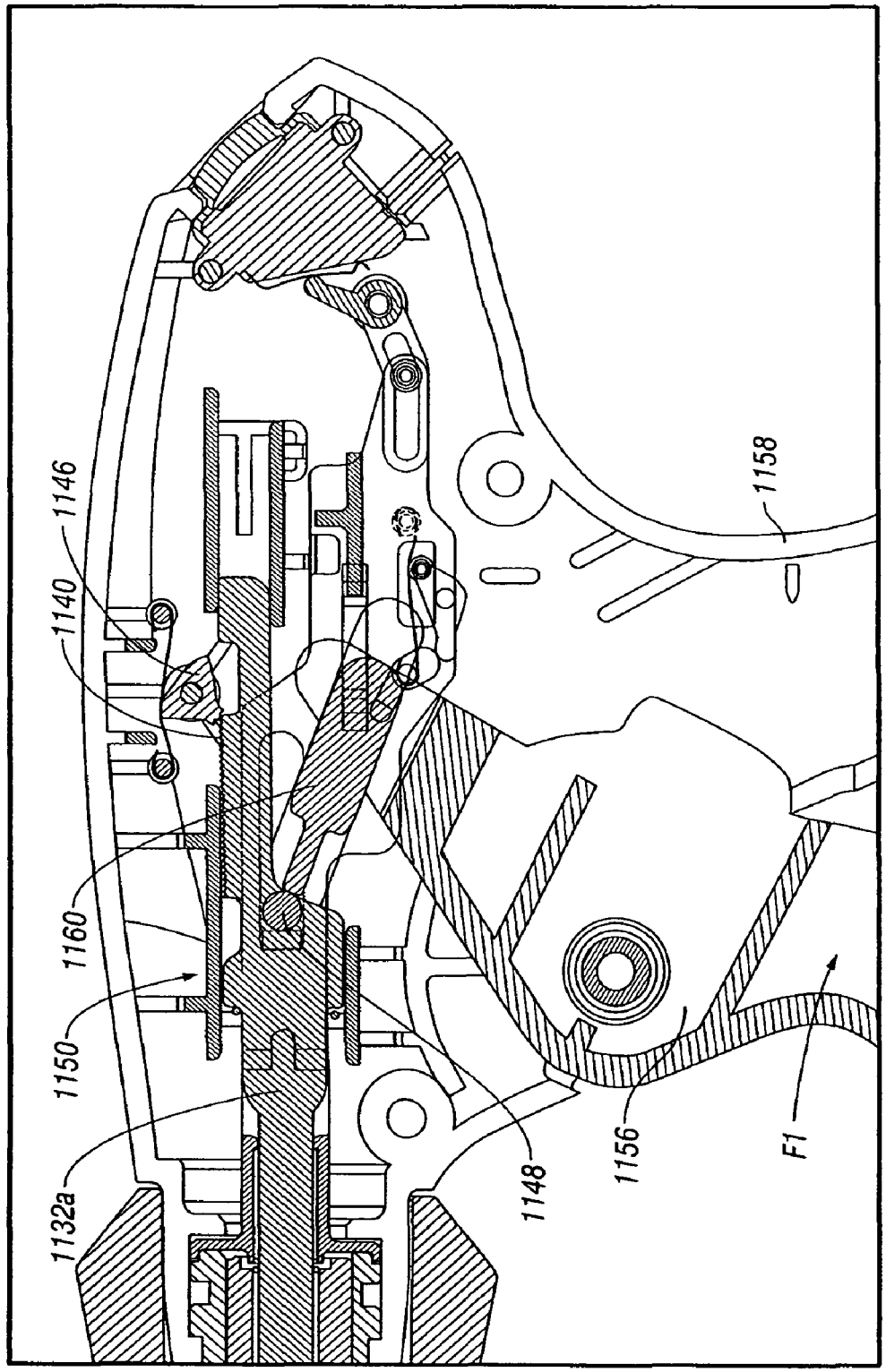
Figure 122:
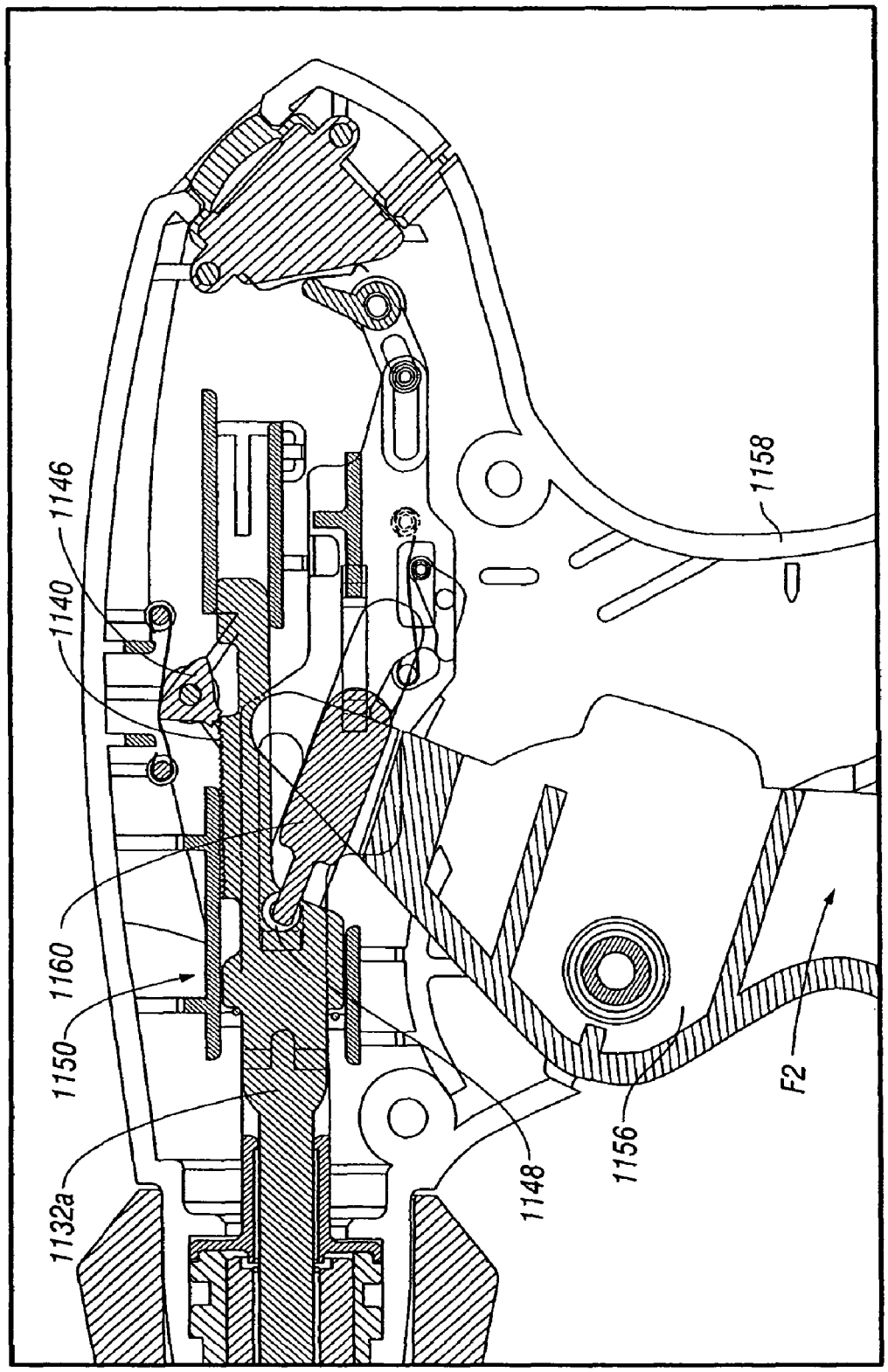

FIG. 96 is a perspective view of the handle portion having the assembled signaling device;

FIG. 97 is a perspective view of a clip applied to a vessel;

FIG. 98 is a side view of a spring;

FIG. 99 is a top view of a clip carrying channel according to another embodiment of the present disclosure;

FIG. 100 shows an enlarged view of the clip carrying channel of FIG. 99;

FIG. 101 illustrates a top view of a lockout bar;

FIG. 102 shows a side view of the lockout bar of FIG. 101;

FIG. 102A is a perspective view of the lockout bar of FIG. 101;

FIG. 103 shows a partially assembled view of the lockout bar of FIGS. 101 and 102 and the spring of FIG. 98;

FIG. 104 is a top view of a clip follower;

FIG. 105 shows a side view of a feed bar having a distal nose and a pair of proximal fins;

FIG. 106 shows a top view of the lockout bar of FIG. 101 in a channel of the clip follower;

FIG. 107 illustrates the lockout bar extending into the distal aperture of the feed bar;

FIG. 108 illustrates another view of the embodiment of the clip applier having the lockout bar extending into the distal aperture of the feed bar;

FIG. 109 illustrates another view of the embodiment of the clip applier having the cover removed and showing the lockout bar extending into the distal aperture of the feed bar;

FIG. 110 illustrates another view of the embodiment of the clip applier having the cover and feed bar removed and showing the lockout bar in the feed bar;

FIG. 111 illustrates another a bottom view of the clip follower with the lockout bar and spring in the channel of the clip follower;

FIG. 112 is a cross sectional view of the clip follower having the lockout bar and the spring in the channel along line 16-16 of FIG. 111;

FIG. 113 is a top view of the feed bar having a distal nose and a distal aperture;

FIGS. 114 through 115 are a cross sectional view and bottom view of the spindle of the clip applier having a proximal window;

FIG. 116 is an enlarged view of the window of the spindle of FIG. 114;

FIG. 117 is a side view of the pawl and rack being reset or in the "at rest" or home position;

FIG. 118 is a side view of the pawl and rack being in the intermediate position and configured to prevent retraction of the spindle;

FIG. 119 is a perspective view of a shear pin according to the present disclosure;

FIG. 120 is a side cross-sectional view of the clip applier illustrating the rack and pawl locking out the spindle;

FIG. 121 is a side cross-sectional view of the clip applier illustrating an initial movement of the trigger; and FIG. 122 is a side cross-sectional view of the clip applier illustrating a further movement of the trigger.

DETAILED DESCRIPTION OF THE EMBODIMENTS

There is disclosed a novel endoscopic surgical clip applier having a jaw control mechanism configured to maintain jaws of the surgical clip applier in a spaced apart and stable position during insertion of a surgical clip. The novel endoscopic surgical clip applier also has a lockout mechanism. The lockout mechanism prevents the surgical clip applier from firing when there are no remaining hemostatic clips. The novel endoscopic surgical clip applier also has a signaling device for alerting the surgeon that a clip has been fired. It should be noted that, while the disclosed jaw control mechanism, the driver lockout and the signaling device are all shown and described in an endoscopic surgical clip applier, the disclosed mechanisms are applicable to any surgical clip applier or another instrument having a pair of compressible jaws. Reference should be made to the drawings where like reference numerals refer to similar elements throughout the various figures.

Figure 1:
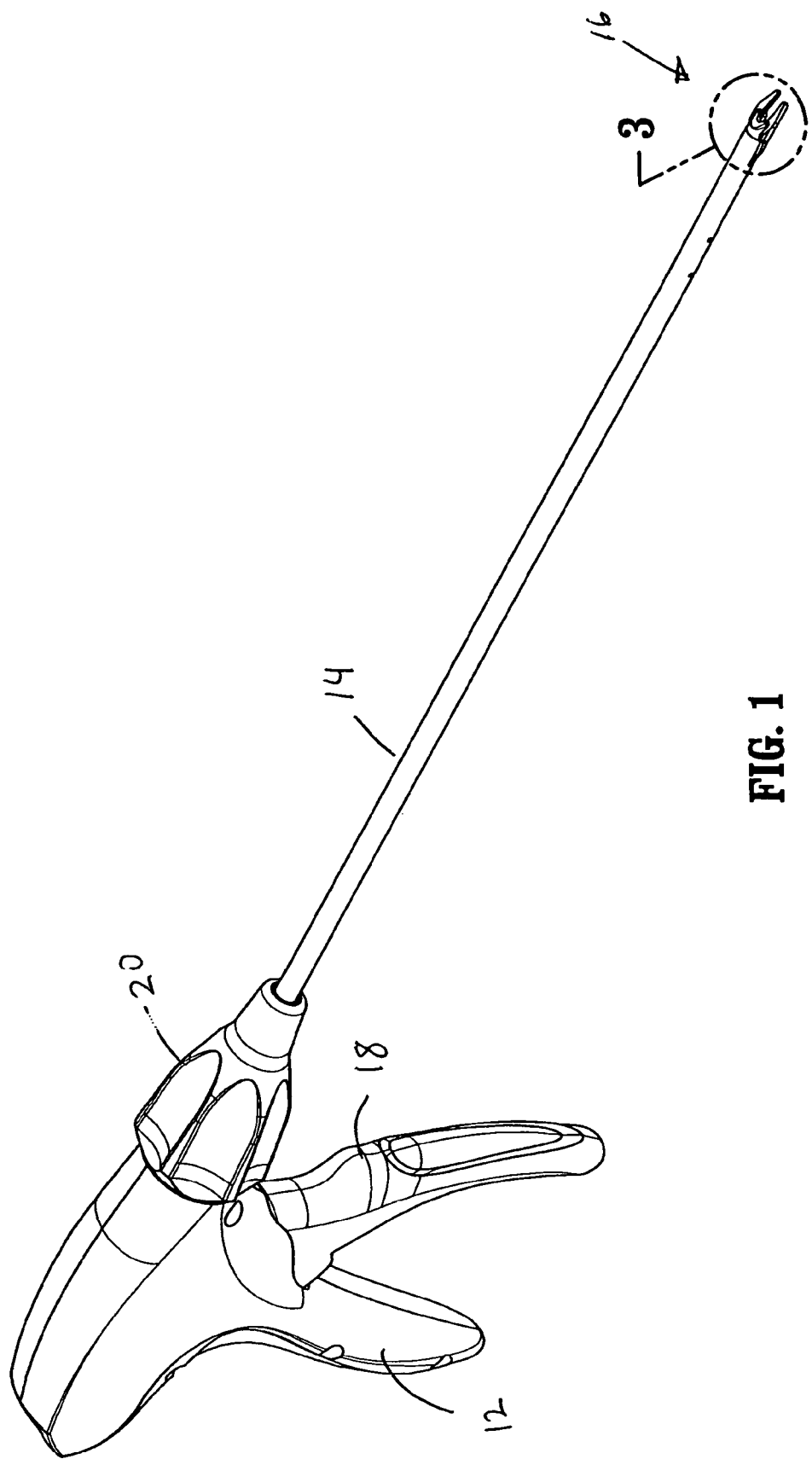
FIG. 1 is a perspective view of a surgical clip applier.

There is disclosed a novel endoscopic surgical clip applier of the present disclosure. Referring now to FIG. 1, the surgical clip applier 10 generally has a handle assembly 12 and an endoscopic portion with an elongated tubular member 14 that extends distally from the handle assembly 12. The handle assembly 12 is made from a thermoplastic material and the elongated member is made from a biocompatible material. In one embodiment, the material may be a stainless steel or in yet another embodiment a titanium material or alloy. A pair of jaws 16 is mounted on the distal end of the tubular member 14. The jaws 16 are actuated by a trigger 18. The trigger is movably mounted in handle assembly 12.

The jaws 16 are also formed from a suitable biocompatible material such as stainless steel, titanium or a suitable alloy. The endoscopic portion also has a knob 20. The knob 20 is rotatably mounted on a distal end of the handle assembly 12 and is connected to the elongated tubular member 14 to provide a three hundred sixty degree rotation of the elongated tubular member 14 and the jaws 16 thereon relative to a longitudinal center axis of the elongated tubular member 14. A significant aspect of the clip applier 10 is that the knob 20 has a suitable configuration so as to be rotated simply using a surgeon's finger, and will be discussed in depth below.

Figures 2, 3:
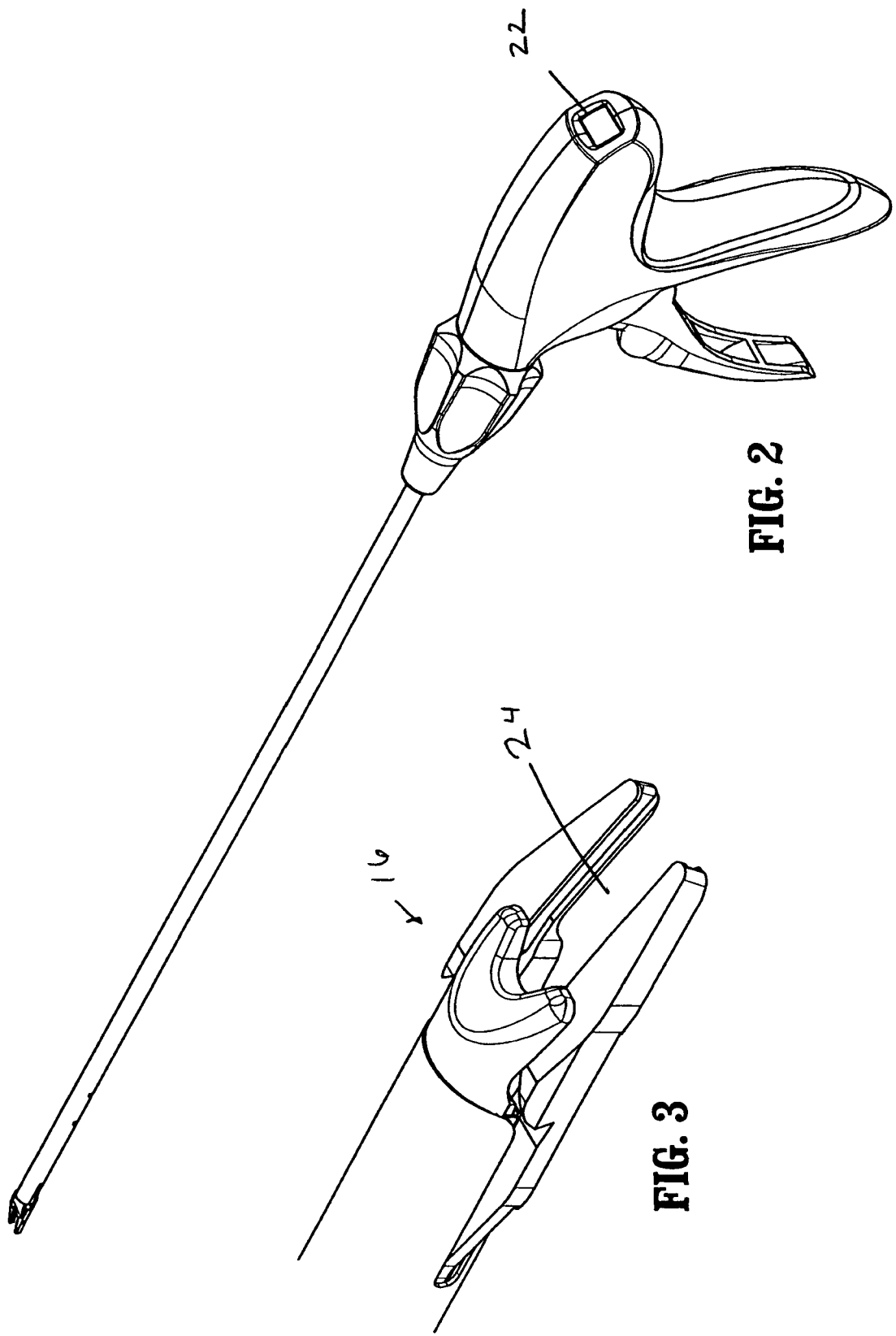
FIG. 2 is another perspective view of the surgical clip applier of FIG. 1.
FIG. 3 is an enlarged perspective view of the jaw structure of the surgical clip applier.
Figure 2A:
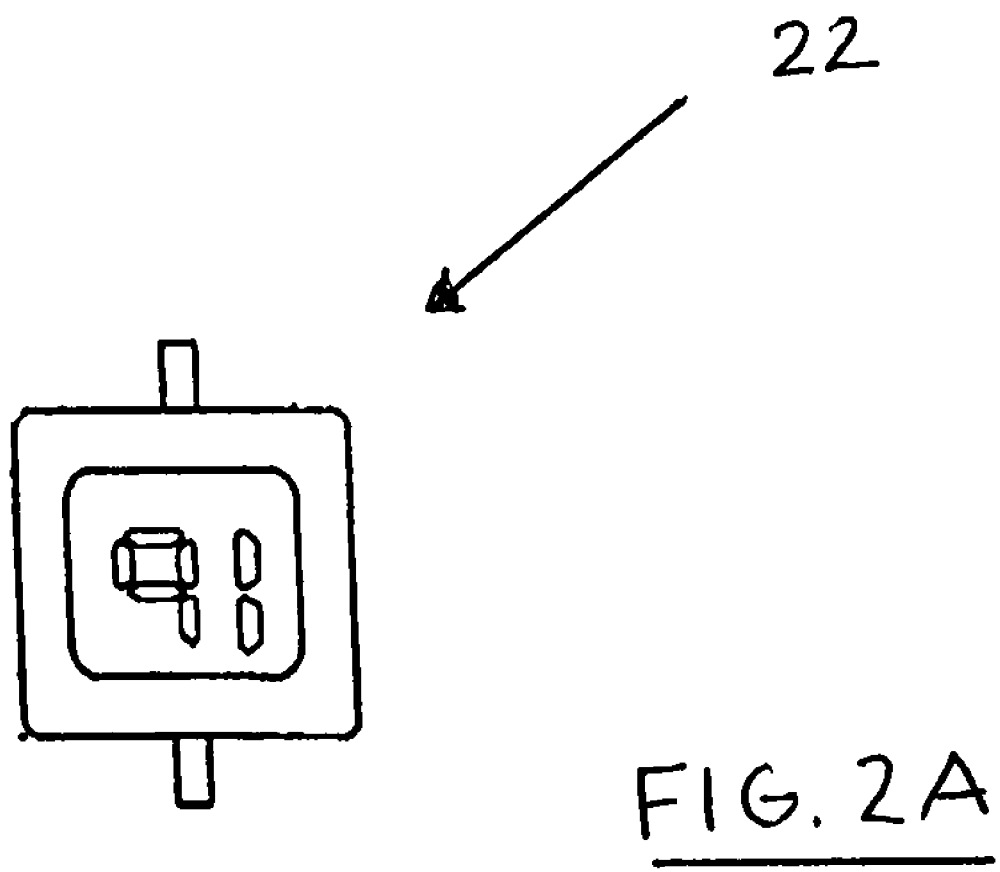
FIG. 2A shows a front view of a display of the surgical clip applier showing a displayed parameter.
Figure 4:
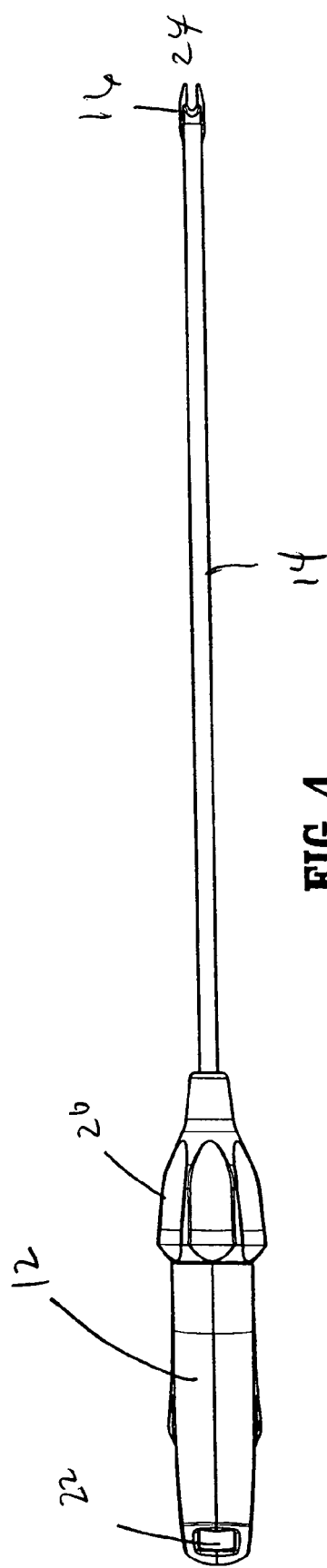
FIG. 4 is a top view of the surgical clip applier.

Referring now to FIG. 2, the endoscopic surgical clip applier 10 has a display 22. The display 22 may be any device known in the art to provide an indication of an event. The event may be related to the procedure or the operation of the clip applier 10. The display 22 in a preferred embodiment may be a liquid crystal display. However, in another embodiment, the display 22 may be a plasma display, one or more light emitting diodes, a luminescent display, a multi-color display, a digital display, an analog display, a passive display, an active display, a so called "twisted nematic" display, a so called "super twisted nematic" display, a "dual scan" display, a reflective display, a backlit display, an alpha numeric display, a monochrome display, a so called "Low Temperature Polysilicon Thin Film Transistor" or LPTS TFT display, or any other display 22 that indicates a parameter, information or graphics related to the procedure or the clip applier 10. In one embodiment, the display is a liquid crystal display 22 or "LCD". The LCD 22 may be a black and white or color display that displays one or more operating parameters of the clip applier 10 to the surgeon. Referring now to FIG. 2A, there is shown a front view of the LCD display 22. The display 22 shows a displayed parameter. In one embodiment, the displayed parameter may be an amount of remaining clips, a number clips that have been used, a position parameter, a surgery time of usage, or any other parameter of the procedure. The LCD 22 may display text, a graphic or a combination thereof. In one embodiment, the LCD 22 may have a tab made from a Mylar or another polymeric insulating material that is disposed between a LCD 22 battery and a contact of the LCD 22 to prevent the battery from being drained during storage. The tab may extend out of the clip applier 10 in order to allow for removal of the tab. Once removed, the tab will be pulled out from the clip applier 10 and will permit the battery to contact the electrical contact of the LCD 22 to energize the LCD 22 with power. In one embodiment of the present clip applier 10, the LCD 22 has a lens that magnifies the display. The lens of the LCD 22 may magnify the display to any desired size in order to allow a surgeon to read the display with ease from a distance. Referring now to FIG. 3, the jaws 16 have a channel 24 for receipt of a single surgical clip therein. As is known, a surgical clip may be applied or placed in the channel 24 by a loading structure of the clip applier 10 to apply the hemostatic clip in, for example, a body cavity.

Figure 6A:
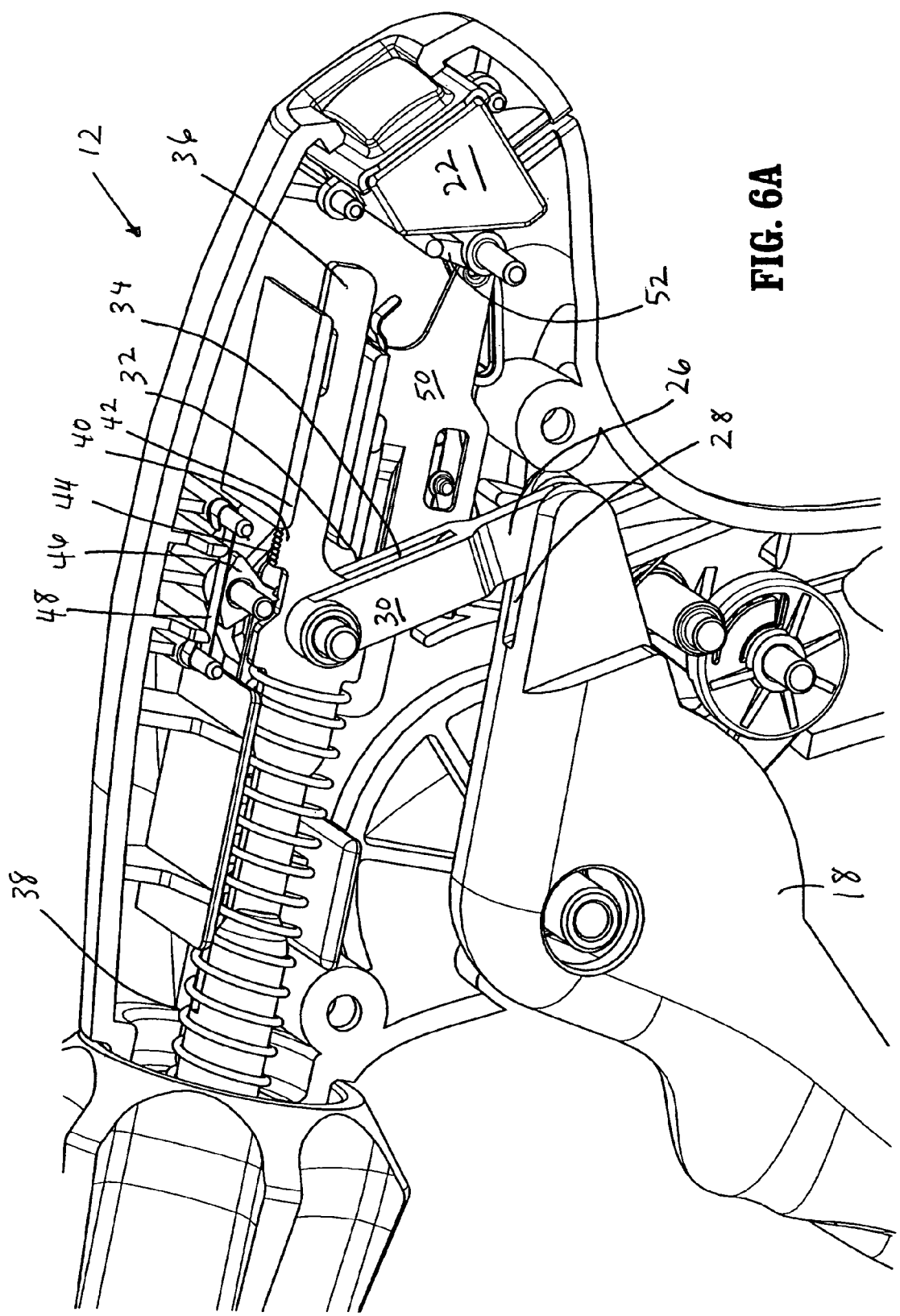
FIG. 6A is a side view, with half of the body removed, of the handle assembly of the surgical clip applier.

Referring now to FIG. 6A, the handle assembly 12 of the endoscopic surgical clip applier 10 is shown from a first open lateral side of the handle assembly 12. The endoscopic surgical clip applier 10 has the trigger 18 connected to a wishbone link 26. The wishbone link 26 is a member that on one end is connected to the trigger 18 through a trigger slot 28 and on an opposite end has first and a second wishbone shaped members 30, 32. The first and a second wishbone shaped members 30, 32 form a space 34 for receipt of a driving member 36.

The driving member 36 is a substantially flat member that is longitudinally disposed in the handle assembly 12 as shown and is intended to move one or more driving structures to load, and actuate the jaws 16 to form a fully formed clip, and then reset to an initial position for the next clip application. A return spring 38 is disposed to surround the driving member 36. The driving member 36 is connected to a driving mechanism to fire the clip applier 10 and is suitably connected such that after the trigger 18 is actuated and the wishbone link 26 advances the driving member 36 in a longitudinal or distal manner, the return spring 38 will return the driving member 36 and the trigger 18 to its original position for the next clip application.

The driving member 36 is advantageous. The driving member 36 prevents an inadvertent return of the trigger 18 before a full actuation of the open clip applier 10 by impeding movement at an intermediate position once the driving member 36 begins to advance distally. The driving member 36 has a rack 40. The rack 40 is disposed on a top side 42 thereof.

The rack 40 has a number of teeth 44 and the teeth 44 are engaged to engage with another complementary surface to prevent inadvertent return of the trigger 18 and the driving member 18 before a full actuation of the surgical clip applier 10. The surgical clip applier 10 has a pawl 46 with a pawl return spring 48. The pawl 46 is biased with the pawl spring 48 to engage with the teeth 44 of the rack 40. The teeth 44 and the pawl 46 prevent a release of the trigger 18 before a full actuation of the trigger 18 as described herein below.

Figure 6B:
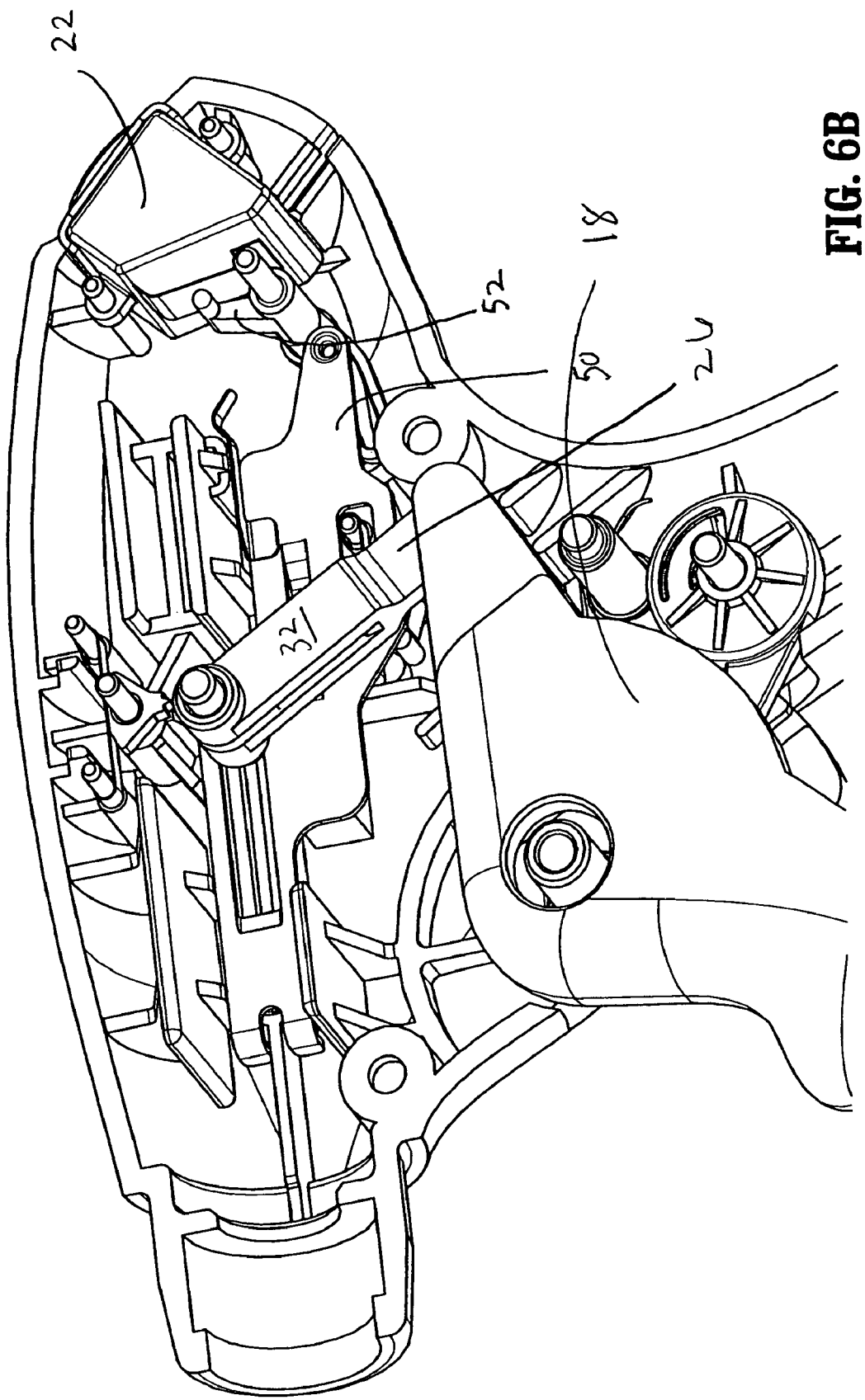
FIG. 6B is an opposite side view relative to FIG. 6A with half of the body removed of the handle assembly of the surgical clip applier.

Referring now to FIG. 6B, the clip applier 10 further has an actuator plate 50. The actuator plate 50 is longitudinally disposed in the handle assembly 12. The actuator plate 50 is disposed below the driving member 36 and is operatively connected to a LCD lever 52.

Referring now to FIG. 6B, the LCD lever 52 is a suitable structure to be operatively connected to the LCD display 22. Lever 52 moves a suitable mechanism or contact in the LCD display 22 to permit the LCD display 22 to be actuated and thus display one or more operating parameters of the clip applier 10. In one embodiment, the actuator plate 50 is connected to the LCD lever 52 to move the corresponding LCD display 22 structure or contact to display an amount of remaining clips that the surgeon has to fire. In another embodiment, the display may be a number of light emitting diodes, a liquid plasma display, an electronic device or display, a changeable display or a combination thereof.

Figure 6C:
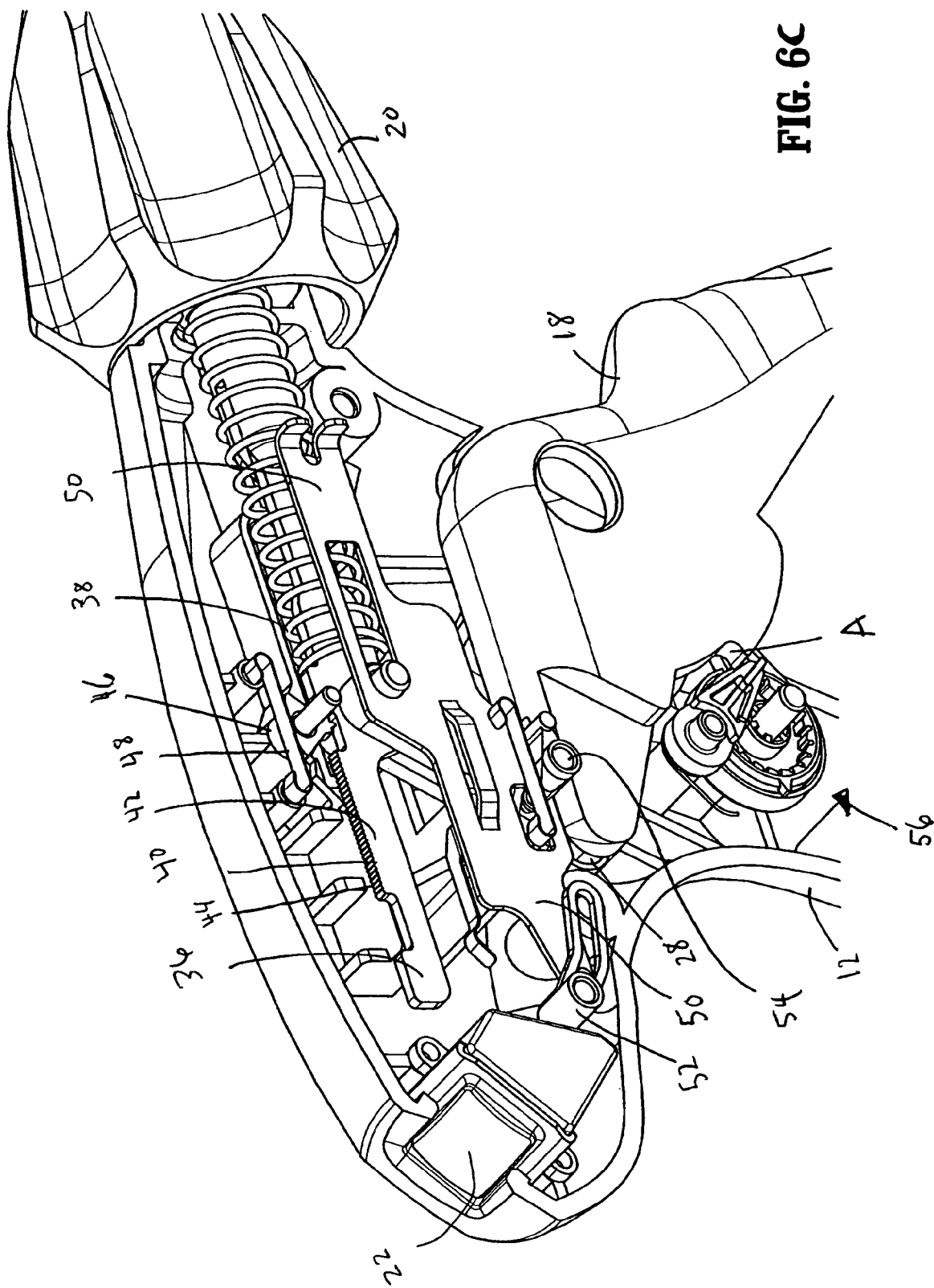
FIG. 6C is a perspective view of FIG. 6B with half of the body removed, of the handle assembly of the surgical clip applier.

Referring now to FIG. 6C, the actuator plate 50 further has a signaling device 54. The signaling device 54 is a device that is connected to the actuator plate 50 and that can provide the user with an audible signal that the open clip applier 10 has fired the surgical clip. The signaling device 54 emits a sound once the clip applier 10 is fired to provide audible feed back to the surgeon. In another embodiment, the signaling device 54 may be another electronic device that emits a characteristic sound. The signaling device 54 may emit a sound in response to a deflection of the handle or trigger, a compression of a clip, a loading of the clip, a loading of a new clip, an exhaustion of all of the clips, or may emit several different sounds depending on the clip applier 10 event. The characteristic sound may be a click, a chirp, a sound, a voice, a recording, a combination of sounds, or any acoustic wave at any decibel level. The signaling device 54 may further provide an identification in response to an event of the clip applier 10. In one embodiment, the signaling device 54 may emit a sound during normal operation, and then upon the occurrence of the event terminate emitting the sound. Various configurations are possible and all within the scope of the present disclosure.

Referring still to FIG. 6C, the clip applier 10 further has a lockout mechanism 56. The lockout mechanism 56 is a structure to prevent the surgeon from dry firing the open clip applier 10 when the amount of clips stored in the clip applier 10 have been exhausted. The lockout mechanism 56 engages a complementary structure in the trigger handle A to prevent the trigger 18 from further moving and actuating the wishbone link 26 in a manner described in more detail below.

Figure 7:
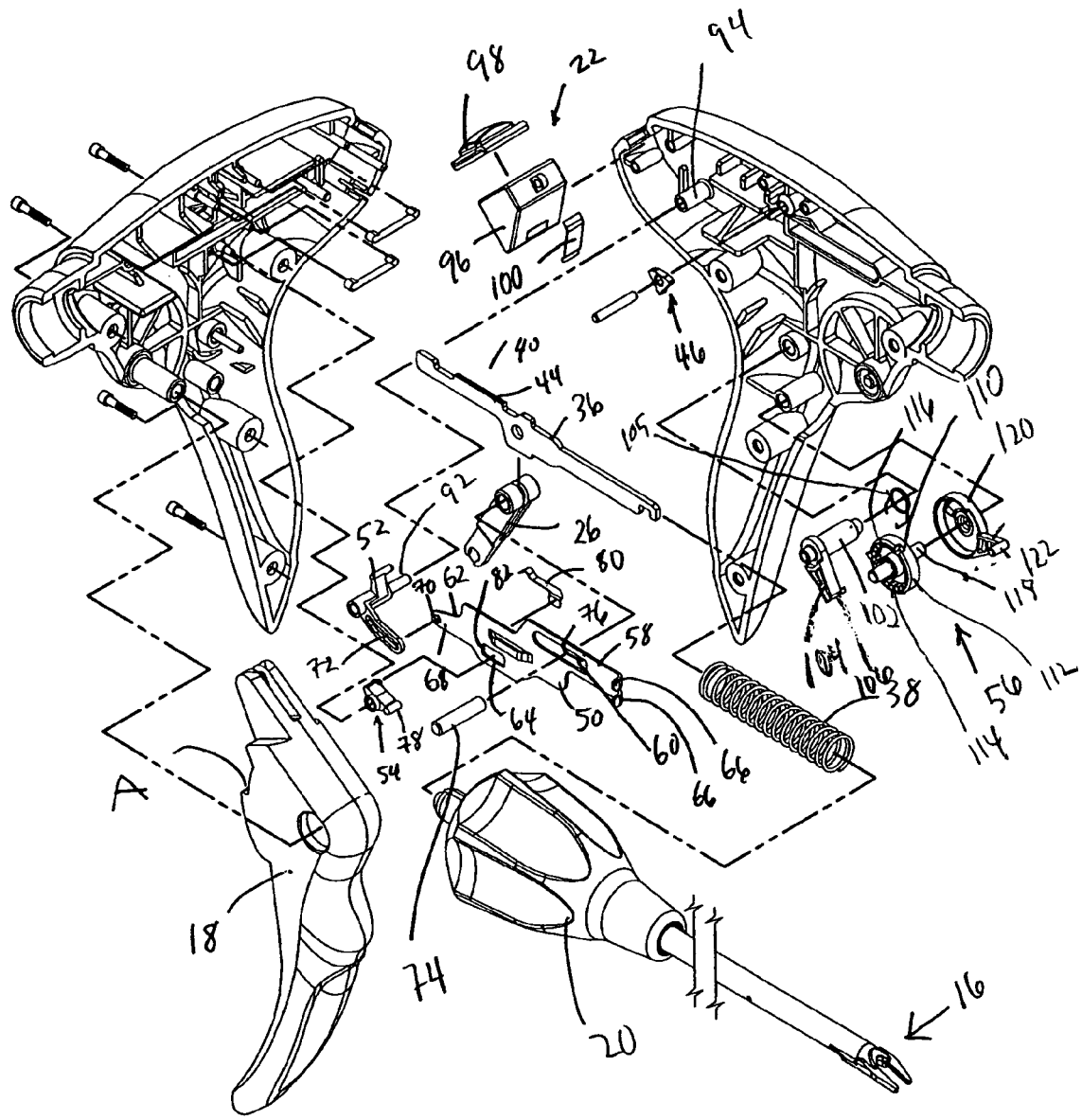
FIG. 7 is a perspective view of the handle housing of the clip applier, with parts separated.

Referring now to FIG. 7, there is shown an exploded view of the handle assembly 12 from an opposite side. The surgical clip applier 10 has the actuator plate 50 that is a substantially "S" shaped member. As best shown in FIGS. 7 and 9A, the actuator plate 50 has a first portion 58 having a first orthogonal shaped window 60 and a second portion 62 with a second orthogonal shaped window 64.

On a first end of the actuator plate 50, the actuator plate 50 has a rounded off or curved portion that forms a pair of tines 66. The opposite second end 68 has a protrusion 70. The protrusion 70 engages a channel 72 on the LCD lever 52. A pin 74 is disposed through the first orthogonal shaped window 60 to connect the actuator plate 50 to the driving member 36 through the wishbone link 26. In this manner, when the trigger 18 moves the driving member 36 distally, the connecting pin 74 upon being moved through the first window 60 will also move the actuator plate 50 distally in a similar fashion once the connecting pin 74 contacts an outer distal edge 76 of the first orthogonal shaped window 60.

Referring again to FIGS. 7, and 9B, the clip applier 10 further has the signaling device 54 with an audible click lever 78. The audible click lever 78 is on an opposite side of the actuator plate 50 and is through the second window 64. The signaling device 54 also has an audible click spring 80. The signaling device 54 also has the audible click lever 78 that will rotate and deflect on a complementary handle surface upon longitudinal distal movement by the actuator plate 50. The actuator plate 50 will move the second window 64 having a lateral side 82 (shown in FIG. 9A) that will cause a post 77 of the audible click lever 78 (FIG. 9B) to deflect and cause the lever 78 to contact a surface rib on the housing. This contact produces an audible alert or an audible signal to the surgeon that the clip applier 10 has fired a surgical clip.

Referring to FIG. 7, the clip applier 10 further has the LCD lever 52 (best shown in FIG. 9C) that is a rotatable member with a first lever portion 84, an aperture 86 and a curved member 88 having the channel 72. The channel 72 communicates with the protrusion 70 on the actuator plate 50 and has a peg 92 that communicates with the first handle housing portion 94 shown in FIG. 7.

Referring to FIG. 7, the LCD 22 has a LCD unit 96 with an LCD lens 98 and a LCD counter contact plate 100 that is connected to the LCD 22. The LCD counter contact plate 100, upon being actuated will toggle the LCD display 22 from a previous parameter to the current parameter, such as in one embodiment, an amount of remaining clips in the clip applier 10.

The clip applier 10 also has the pawl 46 with the pawl spring 48. The pawl 46 has an end that engages with the teeth 44 of the rack 40.

Referring to FIG. 7, the clip applier 10 further has the lockout mechanism 56 having a first rotatable member or shaft 102 with an arm 104 and a pawl 106 connected to the arm 104. The first rotatable member 102 is generally cylindrical shaped and is connected to a complementary surface of the handle through a spring 105. In one embodiment, the first rotatable member 102 is a lock out arm The lockout mechanism 56 further has a second rotatable member 112 offset from the first rotatable member 102. The second rotatable member 112 in one embodiment is a lockout wheel and has a generally circular configuration with an inner circumference 114 of the lockout wheel 112 having a number of teeth 116 spaced therearound. The lockout wheel 112 has a centermost post 118 that is connected through an aperture to a third rotatable member 120 having a first arm 122 connected thereto, and the post 118 is further connected to the handle portion 12. As the trigger 18 is fired, there exists a relative movement between the first rotatable member 102 connected to the handle portion 12 and the third rotatable member 120 connected to the trigger 18. As such, the lockout wheel 112 is intended to rotate a predetermined amount as the centermost post 118 is connected to the handle portion 12. As the lockout wheel 112 rotates, the pawl 106 of the first rotatable member 102 will advance. Each time the trigger 18 is fired to fire a clip; the pawl 106 will traverse one unit of length between the number of teeth 116 and will rest therein due to an advantageous ratcheting arrangement discussed herein. The lockout wheel 112 has an escape notch 110 that is an orthogonally shaped notch 110 on a radial portion thereof. Escape notch 110 permits the pawl 106 of the first rotatable member 102 to traverse from an inner location or the inner circumference 114 of the lockout wheel 112 outward through the escape notch 110 to engage the complementary structure in the trigger shown by reference letter A to prevent the trigger 18 from further moving and actuating the wishbone link 26.

Figure 7G:
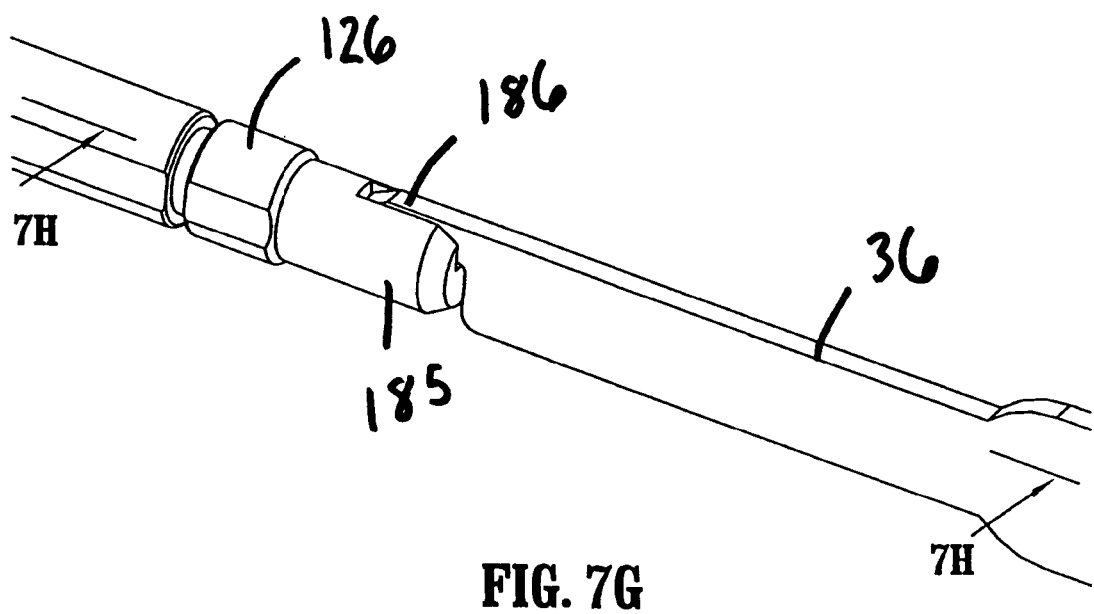
FIG. 7G shows a view of a spindle link connecting to the driver bar.
Figure 7H:
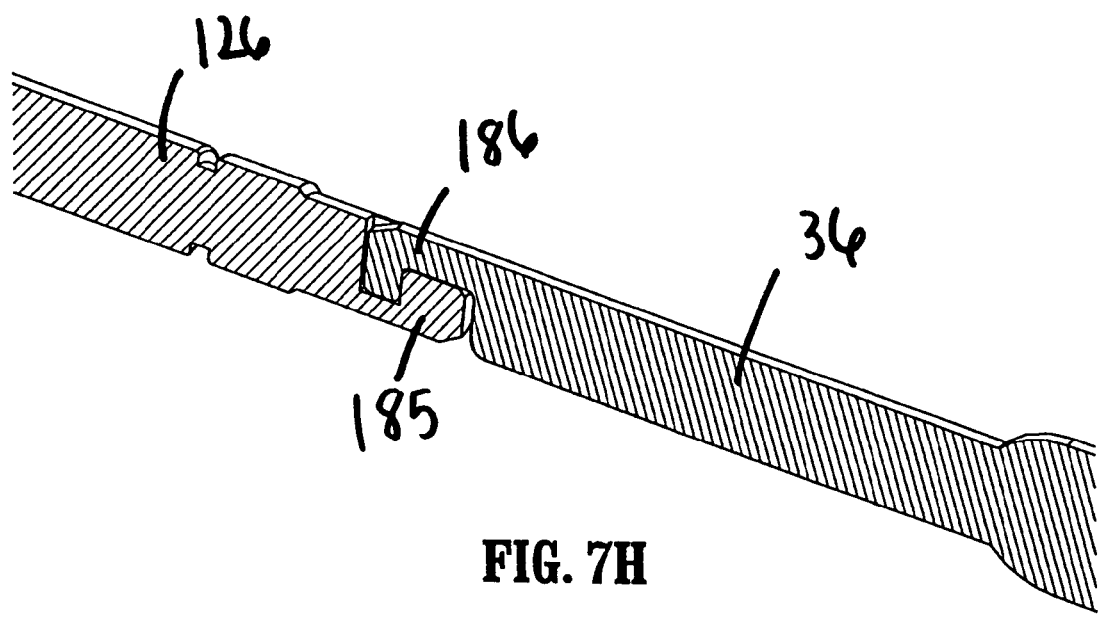
FIG. 7H shows a cross sectional view of the spindle link connecting to the driver bar along line 7H-7H of FIG. 7G.

The clip applier further has the knob 20 having a shaft assembly 124. A spindle link 126 connects to a spindle 128 shown in FIG. 7A. Referring now to FIG. 7G and FIG. 7H, the driver bar 36 connects with the spindle link 126. The spindle link 126 on a proximal side opposite the jaws 16 has spindle link hook 185. The driver bar 36 has an angled hook member 186. The angled hook member 186 is on a distal side 184 of the driver bar 36. Referring now to the cross sectional view along line 7H-7H of FIG. 7G, the angled hook member 186 of the driver bar 36 mates with the spindle link hook 185. As shown, the driving member 36 can thus advance the spindle link 126 in a distal manner. Referring now again to FIG. 7A, an opposite distal end of the spindle link 126 (relative to the spindle link hook 185) is connected with a circular boss connection 188 to the spindle 128. In this manner, the spindle 128 may rotate independently of the spindle link 126 as shown by the reference arrow B.

Figure 5:
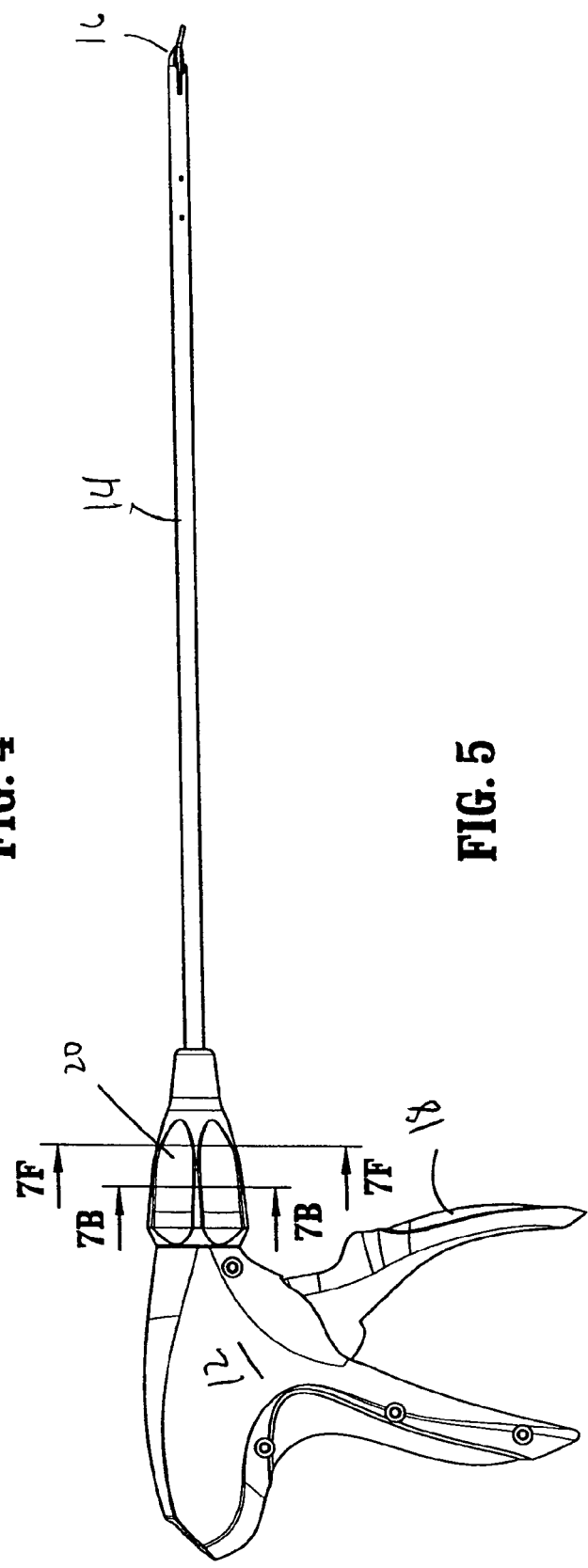
FIG. 5 is a first side view of the surgical clip applier.

Referring now to FIG. 7B, there is shown a cross sectional view of the knob 20 along line 7B-7B of FIG. 5. The knob 20 has a first body half 130 and a second body half 132 connected to one another in an aperture or bore 134 of the knob 20.

Referring now to FIG. 7C, the knob 20 connects with a knob housing 136 having a planar tapered surface 138 that connects with the knob 20. Referring again to FIGS. 7B and 7C, the knob 20 has the bore 134 disposed therethrough. The knob housing 136 further has an outer tubular member 142 with a first slot 144 and a second slot 146 disposed through the tubular member 142 with the outer tubular member 142 having a "C" shaped first aperture 148 and a second "C" aperture 150 on respective opposite laterals sides thereof.

Notably, the knob housing 136 is very advantageous as the knob housing 136 has an elongated cylindrical geometry that is suitable to allow a surgeon to rotate the tubular member 14 simply with one hand by using an index finger to contact a lateral side of the knob 20 and rotate the knob 20 either in a clockwise or a counter clockwise manner. This obviates any two handed operation to rotate the tubular member 14 that is disfavored by some surgeons and provides for a more ergonomic operation or rotation of the tubular member 14.

Referring now to FIG. 7C, the knob 20 on an inner surface of the bore 134 has a first arm 152 and a second arm 154 that extend opposite an outer surface into the bore 134 for respectively mating with the first "C" shaped aperture 148 and the second "C" shaped aperture 150 of the knob housing 136.

Referring again to FIGS. 7B and 7E, the outer tube 14 further has a bushing 156 with a first aperture 158' and a second aperture 160' with a first pin 162 extending through the first aperture 158' and a second pin 164 extending through the second aperture 160'. Referring now to FIG. 7E, the bushing 156 further has a tab 166 that extends from a radial position of the bushing 156. The tab 166 engages with a notch in the knob housing 136. The bushing 156 also has a second tab 166'. The second tab 166' also engages a notch 168 in the tubular member 14 shown in FIG. 7D for rotation thereof. In order to actuate the various components, the spindle 128 is mounted for longitudinal movement through the tubular member 14.

Referring now to FIG. 8, there is shown a perspective view of the pawl 46 previously described. The pawl 46 is a triangular shaped member with an aperture 169 disposed therethrough. The pawl 46 also has a number of angled surfaces 170, 172, 174 on a top side 176 and a tooth engaging structure 178 on an opposite bottom side 180 for engaging with the teeth 44 on the rack 40 as shown in the driving member 36 of FIG. 6D. As shown, the driving member 36 has an aperture 182 for mating with the wishbone link 26 of FIG. 9D and has a first side 181 and an opposite second side 184 with an angled hook member 186 for advancement of the spindle 128 in a distal manner.

Referring now to FIG. 9D, the wishbone link 26 is connected to the driving member 36 through the first longitudinal shaped window 60 of FIG. 9A on the actuator plate 50 by means of the pin 74. The actuator plate 50 with the protrusion 70 connects with the channel 72 in the LCD lever 52 of FIG. 9C and the actuator plate 50 is further connected to the signaling device 54 shown in FIG. 9B. The signaling device 54 has an aperture 188 for mating with the handle housing. The audible click lever 78 has a bulbous end 190 with a resilient surface 191 such that upon rotation of the click lever 78 the bulbous end 191 can sharply contact another handle surface or rib in order to an acoustic wave to emanate from the handle assembly 12 to signal that the surgical clip has fired. The signaling device 54 further has the post 77 is connected through the second window 64 of FIG. 9A and that rotates the lever 54 when the actuator plate 50 moves distally.

Figure 10:
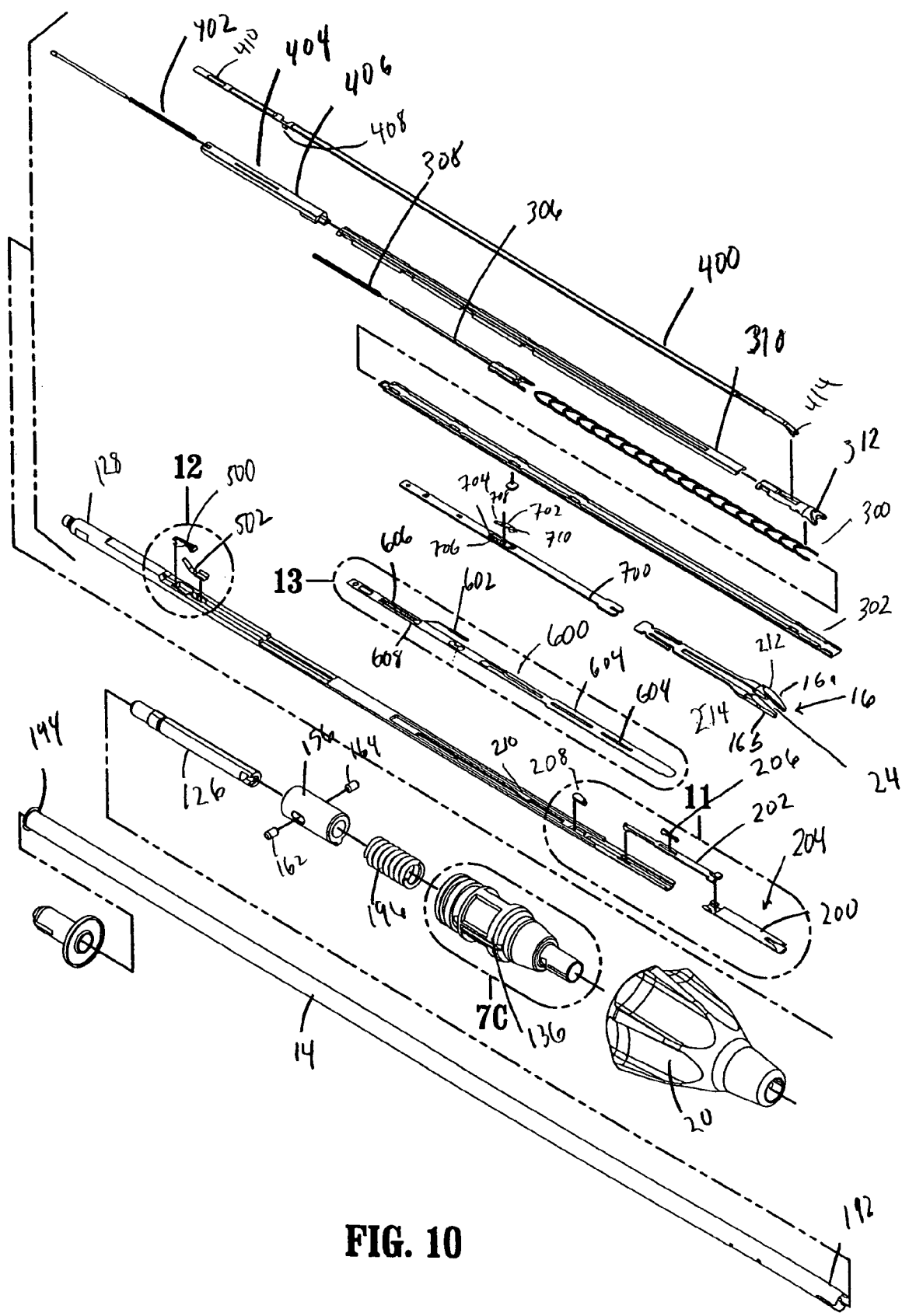
FIG. 10 is a perspective view, with parts separated, of the surgical clip applier.

Referring now to FIG. 10 there is shown an exploded view of the various components of the endoscopic portion 16 of the open clip applier 10. The clip applier 10 has the outer tubular member 14. The outer tubular member 14 is generally a cylindrical member having a first end 192 and a second end 194. The first end 192 is connected through the bore to the spindle link 126. As mentioned, the spindle link 126 is connected to the spindle 128. The outer tube 14 is disposed around the spindle 128. The clip applier 10 has pins 162, 164. The pins 162 and 164 extend through the lateral sides of the bushing 156. The pins 162 and 164 are biased inward relative to the bushing 156 and contact the outer tubular member 14. The clip applier 10 further has a spring 196 to prevent the bushing 156 from advancing. The spring 196 is disposed in the knob housing 136 that connected to the knob 20.

The clip applier 10 further has the interlocking spindle link 126 that is disposed through the bore of the elongated tubular member 14. The present clip applier has a number of different assemblies in order to perform a number of different clip applier functions. The clip applier 10 has a spindle mechanism 128 in order to traverse through the tubular member 14 to actuate a driving mechanism to close the jaws 16 and form a fully formed clip. The clip applier 10 also has a mechanism for a wedging function that is provided to maintain the jaws 16 in a spaced apart condition for loading the jaws 16 that retracts once the jaws 16 are loaded. The clip applier 10 also has a feeder function that feeds clips to the jaws 16. The clip applier also has a clip storage function and a clip follower function that biases the stored clips for subsequent loading thereof.

In order to actuate the various components there is provided an actuation mechanism or the spindle 128 shown above the knob 20 in FIG. 10. The spindle 128 is mounted for longitudinal distal and proximal movement through the elongated tubular member 14. The spindle 128 has, on a distal end 204, a camming mechanism with a driver bar 200 and a slider joint 202 that extends from a distal end 204 of the spindle 128 to selectively engage the camming surfaces and to close the jaws 16 around the surgical clip.

The spindle 128 further has a latch member 206 on the slider joint 202 and a cam link 208 on the spindle 128. The latch member 206 cams in a direction toward the spindle 128. The latch member 20 cams into a corresponding slot of the spindle 128. The latch member 206 permits the driver bar 200 to move distally. The latch member 206 also prevents the driver bar 200 from actuating the jaws 16 when spindle 128 moves distally to reduce a predetermined dwell distance between the spindle 128 and the driver bar 200. The spindle 128 also has a camming feature 210 or bulging edge to move another structure in a perpendicular manner relatively to a longitudinal axis of the spindle 128 during a distal advancement.

The clip applier 10 retains one or a number of surgical clips 300 for application to the desired tissue. The clip applier 10 has an elongated clip channel member 302 for retaining a number of surgical clips 300 shown in an aligned manner above the clip channel member 302. The elongated clip channel member 302 does not move longitudinally relative to the elongated tubular member 14. The clip applier 10 has a follower 306 connected to a follower spring 308. The follower spring 308 urges clips distally in the clip channel member 302. The clip applier 10 also has a channel cover 310 that overlies the clip channel member 302 to retain and guide the follower 306 and the follower spring 308 and the clips 300 distally in the clip channel member 302. The clip applier 10 also has a nose 312 to direct the clips 300 traversing through the clip channel member 302 into the channel 24 between the jaws 16.

The clip applier 10 also has a feed bar 400 for feeding clips 300 into the channel 24 between the jaws 16. The feed bar 400 also provides for a relative movement. Referring now to a distal portion of clip channel member 302, there is shown the feed bar 400. The feed bar 400 at this distal location advances the clips 300 into the channel 24 and between the jaws 16. Referring now to a proximal location opposite the jaws 16, the feed bar 400 has a pusher spring 402 (FIG. 10). The pusher spring 402 biases the feed bar 400 in a longitudinal distal direction. The pusher spring 402 is disposed in a complementary location under a notch 404 in a trip block 406. On a distal side of the trip block 406, the trip block 406 is adjacent to the clip channel cover member 304. The feed bar 400 is shown above the trip block 406. The feed bar 400 has a hook 408. The hook 408 engages in the notch 404 of the trip block 406. The clip applier 10 further has a guide pin 401. The guide pin 401 is disposed through the pusher spring 402 and necessary to align the pusher spring 402. The hook 408 engages with the guide pin 401 and the pusher spring 402 under the trip block 406. In this manner, the hook 408 is disposed through the notch 404 to engage the guide pin 401. The pusher spring 402 and guide pin 401 biases the feed bar 400 and permits the feed bar 400 to advance distally. Moreover, the guide pin 401 being disposed through the pusher spring 402 allows for a self contained assembly. In order for spindle 128 to advance the pusher 400, the spindle 128 has a trip lever 500 and a biasing spring 502. The trip lever 500 is engaged with the feed bar 400 to advance the surgical clips 300 distally into the clip channel 24 between the jaws 16.

The clip applier 100 also has a wedge plate 600 with a wedge plate spring 602. The wedge plate 600 is a flat bar shaped member having a number of orthogonally shaped windows 604 disposed therethrough. The wedge plate spring 602 surrounds a tongue 606 in the wedge plate 600 that is in a latch aperture 608. The wedge plate spring 602 permits the wedge plate 600 to be retracted from a distal location to a proximal location after being advanced distally to separate the jaws 16 for clip loading. The wedge plate 600 also has a "C" shaped window 610 that is between the windows 604 and the tongue 606.

The clip applier 10 also has a filler component 700. The filler component 700 has a rotatable member 702 and a spring bar member 704. The spring bar member 704 is in an aperture 706 disposed in the filler component 700. The rotatable member 702 is capable of a certain particular range of motion and has a first proximal end 708 and a second opposite distal end 710 that is opposite the first end 708. The range of motion of the rotatable member 702 may be any relatively slight or any relatively large range of rotation or movement. The present clip applier 10 is not limited in any manner to any specific degree of rotation or any specific manner of movement such as circular, elliptical or even any geometric rotational pattern, origin, axis, coordinates or movement. Moreover, the member 702 may alternatively simply move in any planar or in another irregular manner known in the art. Various configurations are possible and within the scope of the present disclosure.

The clip applier 10 further has the jaws 16. The jaws 16 are made of a first jaw member 16a and a second jaw member 16b. Between the first jaw member 16a and the second jaw member 16b is the clip channel 24. As is understood, the jaw members 16a and 16b can move inwardly to close and compress to form a fully formed clip in the channel 24. The jaws 16 also have a first raised camming surface 212 and a second raised camming surface 214 on an outer surface thereof. The first raised camming surface 212 and the second raised camming surface 214 permit another driving camming surface selectively engagement therewith for closing and compressing the jaws 16.

Referring now to FIG. 10A, there is shown a view of the feed bar 400. The feed bar 400 is a longitudinal member having the rectangular shaped window 410 for engagement with the trip lever 500. The feed bar 400 also has the hook 408 disposed on a bottom side 412 of the feed bar. The feed bar 400 further has a pusher 414 on a distal end for engaging and manipulating the surgical clips 300 in the clip carrying channel 302.

As shown in FIG. 10B, the feed bar 400 cooperates with the follower 306 that slides in the clip carrying channel 302 for pushing and urging the clips 300 distally in the clip carrying channel 302. As shown in FIGS. 10C and 10D, there is shown the trip block 406 both in a first position and in an opposite second position.

As discussed above, the trip block 406 has the notch 404 therein and also has an angled surface forming a first and second toothed member 420. Each of the first and the second toothed members 420 is for engagement with the corresponding surface of the trip lever 500 that will be discussed herein. The notch 404 of the trip block 406 in FIGS. 10C and 10D is for receipt of the hook 408 of the feed bar 400 shown in FIG. 10A. In order to disengage the trip lever 500 from the window 410 of the feed bar shown in FIG. 10A, the trip block 406 of FIG. 10C and 10D has the first and second toothed member 420 that engage the trip lever 500 shown in FIG. 10. First and second toothed member 420 disengages the trip lever 500 from the window 410 of FIG. 10A.

Referring now to FIGS. 10E through 10F, there is shown a spindle 128. Referring to FIG. 10 F, the spindle 128 has a first orthogonal cavity 222 and a second orthogonal shaped cavity 224 for receiving the trip lever 500, and for receiving the trip lever biasing spring 502. The first orthogonal cavity 222 has a pivoting boss 226 (FIG. 10F) to allow the trip lever 500 to pivot from a first position to a second rotatable position. The trip lever biasing spring 502 rests in the second cavity 224. The spring 502 shown in FIG. 10 rests therein without any boss or member to connect the biasing spring 502 for ease of manufacture. Referring now to an opposite location of the spindle 128 shown in FIG. 10G, the spindle 128 further has a groove 209 with the camming feature 210 and another cavity 228 to allow the cam link 208 to rest therein and be urged distally. The spindle 128 advances distally to engage the drive components of the clip applier 10 as discussed in further detail below.

Referring to FIG. 12, the trip lever biasing spring 502 has a first and second bowed ends 504, 506 that interlock with the second cavity 224 of the spindle 128 as indicated by a dotted line. The trip lever biasing spring 502 further has a second member 508. The second member 508 biases outward opposite a normal surface of the spindle 128. The second member 508 contacts the trip lever 500. The trip lever 500 has a C shaped end 510 that engages for rotational movement with the pivoting boss 226 of the spindle 128 and another end 512 that extends above the trip lever biasing spring 502. In order to disengage the trip lever 500 with the feed bar 400, the trip block 406 has an angled surface or toothed surfaces 420 that can selectively engage the trip lever 500 and disengage the trip lever 500 from the window 410 of the feed bar 400 as discussed previously.

Referring now to FIG. 11, the spindle 128 has the cam link 208 that is engageable with the wedge plate 600. The cam link 208 has a cam link boss 230 extending therefrom. The cam link 208 is urged distally by the spindle 128 during the stroke.

The slider joint 202 is connected at a proximal end 248 to the spindle 128 at a channel 250. On an opposite side, the slider joint 202 has a "T" shaped end 252. T shaped end 252 is connected to the driver bar 200. The slider joint 202 has a latch member 206 that is a linkage that is disposed to move through an aperture 254 in the slider joint 202 to link with another member and prevent the slider joint 202 from advancing the driver bar 200, and thus preventing camming surfaces 256 of the driver bar 200 from compressing the jaws 16 during the initial stroke of feeding a clip 300 into the jaws 16.

Referring to FIGS. 13 to 13A, the wedge plate 600 is shown. The wedge plate 600 has the wedge plate spring 602. The wedge plate spring 602 provides for a biasing apparatus of the wedge plate 600. The wedge plate 600 is biased by the wedge plate spring 602. The spring 602 surrounds the tongue 606 as indicated by the dotted line. The wedge plate 600 also has a "C" shaped aperture or window 610 therethrough.

The "C" shaped aperture or window 610 selectively engages the rotatable member 702 of the filler component 700. The wedge plate 600 also has a cam slot or groove 612 having a cam surface 614. The cam slot or groove 612 has a predetermined shape that control a motion of the wedge plate 600. The cam slot or groove 612 cooperates with the cam link 208 in the spindle 128 to move the wedge plate 600 distally and to separate the jaws 16 slightly for loading. The cam surface 614 also cooperates with the cam link 208 to move the wedge plate 600 proximally within the tubular member 14 so the jaws 16 may compress the clip 300 in the channel 24 once loaded.

The wedge plate 600 has a rounded distal end 616 for separating the jaws 16 for loading. The wedge plate 600 also has a proximal window 622 to limit retraction of the wedge plate 600.

Referring to FIGS. 14 and 14A, there is shown the filler component 700 in a first position and in a second opposite position shown in FIG. 15. The filler component 700 has a C shaped end 712 and a rotatable member 702 having an aperture 714 that is connected by a pin 716 in a centermost portion of the filler component 700. The rotatable member 702 connects with a corresponding structure in the wedge plate 600 to control a motion of the wedge plate 600. On an opposite side of the filler component 700 is an aperture 718. The rotatable member 702 has a first end 708 and an opposite second end 710. The first end 708 is biased by contact with the spring bar member 704 that allows biasing action between the spring bar member 704 and the rotatable member 702.

The filler component 700 also has (shown in FIG. 15) a filler component cam slot 720. The filler component cam slot 720 is configured to receive the boss 230 of the cam link 208. The filler component 700 also has a stop 722 to limit a proximal retraction of the wedge plate 600 and also has a member 724. The member 724 engages the wedge plate tongue 606 and the spring 602.

Referring now to FIGS. 16 through 17, there is shown spindle 128 and the related drive components. The bushing 156 has the spring 196 being connected thereto as shown in FIG. 17 to allow an over stroke condition of the jaws 16. Spring 196 prevents excessive force from being applied to the jaws 16.

Referring now to FIGS. 18 through 20, there is shown the spindle 128. The feed bar 400 extends in a downward manner (FIG. 19) so the pusher 414 extends into the clip carrying channel 302 to engage a clip 300. The pusher 414 advances each of the clips 300 in the clip channel member 302 into the channel 24 between the jaws 16. Referring to the distal region of the clip applier 10 shown in FIG. 19, the clip applier 10 has a "C" shaped member 416 that is around the nose 312 that acts as a tissue stop disposed therearound. As discussed above, the nose 312 assists with a single clip being introduced in the channel 24. The clip applier 10 also has a number of T shaped tabs 418. The tabs 418 are in order to hold the clip carrying channel 302, the channel cover 310 and the nose 312 together as an integral unit.

Referring to an opposite proximal side relative to the jaws 16 shown in FIG. 20, the spindle 128 has the trip lever 500. The trip lever 500 extends through window 410 of the feed bar 400 as shown to advance the feed bar 400 distally (through the tubular member 14) and to move the pusher 414 distally to introduce the clips 300 into the channel 24 between the jaws 16.

FIGS. 21 through 24 shows a number of clips 300 in a clip carrying channel 302. The clip carrying channel 302 has a number of fingers 420 curved therearound (FIG. 23) in order to support and retain the clips 300 in the clip carrying channel 302. Referring to FIG. 24, there is shown a partially assembled perspective view of the follower 306. The follower 306 is disposed in the clip carrying channel 302 with the follower spring 308 biasing and advancing the follower 306 in a distal direction. The follower spring 308 imparts a force on the clips 300 in the clip channel 302. As shown in FIG. 21, the clip applier 10 has a number of "T" shaped tabs 418 on the clip channel 302 in order to maintain the assembly together.

Referring now to FIG. 25, the clip applier 10 has the trip lever 500 on the spindle 128. The trip lever 500 is a T shaped member that is biased to deflect opposite the spindle top side, and biased by a trip lever spring 502 as previously discussed. Referring now to FIGS. 26 and 27, the driver bar 200 is disposed to rest on the wedge plate 600 or jaws 16 in the assembled position and will traverse distally over the first and second raised camming surfaces 212 and 214 to close the jaws 16 and compress the clip 300 in the channel 24.

Referring now to FIGS. 28 through 30, the relative assembled portions of the trip block 406, the wedge plate 600, and the filler component 700 will now be described. There is shown the wedge plate 600 disposed on the spindle 128.

Referring to FIGS. 29 and 30, the clip applier 10 has a stop member 618 to limit movement of the filler component 700. The filler component 700 is disposed beneath the wedge plate 600 in this view. The wedge plate 600 has the "C" shaped window 610 with the rotatable member 702 disposed through the "C" shaped window 610. The wedge plate 600 also has the cam slot 612 having the cam surface 614. The cam link 208 is disposed on a top of the wedge plate 600 in this view. The cam link 208 has the cam link boss 230 that interfaces with the cam slot 612 of the wedge plate 600.

Referring to FIG. 29, the wedge plate 600 has the wedge plate spring 602 around tongue 606 and the member 724 of the filler component 700 around the tongue 606. In this manner, when the tongue 606 moves distally relative to the filler component 700 the wedge plate 600 is biased to return proximally. The filler component 700 also has the stop 722 in the proximal window 622 of the wedge plate 600 to further limit distal movement of the wedge plate 600 relative to the filler component 700.

Additionally, the cam link 208 is also configured to be driven distally in the cam slot 612. Additionally, the cam link 208 is also configured to be ride in the filler component cam slot 720 shown beneath the wedge plate 600 in this view.

As the cam link 208 is driven distally from the advancing of the spindle 128, the cam link boss 230 engages the cam surface 614 of the wedge plate 600 to drive the wedge plate 600 distally. The wedge plate 600 will advance distally until it reaches a demarcation line 624 shown in FIG. 30. At the demarcation line 624, the cam link boss 231 will engage a disengaging cam surface 726 of the filler component 700 shown in FIG. 30.

The disengaging cam surface 726 is a feature in the filler component cam slot 720. Notably, the disengaging cam surface 726 will cam the cam link boss 231 out of engagement with cam surface 614 of cam slot 612. At this demarcation point 624, the wedge plate 600 no longer moves distally.

Referring now to FIGS. 31 through 34, the various assembled portions of the wedge plate 600, the filler component 700, and the driver bar 200 will be discussed. The wedge plate 600 lies over the filler component 700 which is positioned on the spindle 128. The jaws 16 have a pair of flexible legs 17a, 17b. The legs 17a, 17b are fixed to a base member 17c. The jaws 16 are located at a distal end relative to the flexible legs 17a, 17b. A pair of locking arms 19a, 19b extends from the base 17c and terminates in a pair of tabs 21a, 21b. Tabs 21a, 21b engage a pair of holes (not shown) in the elongated outer tube 14 in order to secure the jaws 16 to the elongated tube 14.

The filler component 700 is disposed immediately proximal relative to the jaws 16 and does not move relative to the elongated outer tube 14. Referring now to FIGS. 31 through 33, there is shown a view of the wedge component 600 disposed over the driver bar 200 and resting on the spindle 128. The wedge plate 600 is under the filler component 700 in FIG. 31. The wedge plate 600 being best shown with the jaws removed in FIG. 33. The jaws 16 are configured to receive the rounded distal end 616 of the wedge plate 600. The rounded distal end 616 initially separates the jaws 16. The rounded distal end 616 maintains the jaws 16 in a separate and aligned configuration during insertion of the clip 300 in the channel 24 of the jaws 16.

The wedge plate 600 has the rounded distal end 616 that maintains the jaws 16 separated and notably prevents any flexing or torque of the jaws 16. Each of the jaws 16 has a cam feature 23a, 23b to guide the rounded distal end 616 of the wedge plate 600 between the jaws 16 as shown in FIG. 32 in an easy and repeatable manner. Cam feature 23a, 23b are on an inner surface of the jaws 16 as shown and is between the first raised camming surface 212 and the second raised camming surface 214.

Referring to FIG. 34, there is shown a view of the spindle 128 having the slider joint 202 and the driver bar 200 having the wedge plate 600 removed for illustration purposes. The distal end of the driver bar 200 has the driver camming surface 256. The driver camming surface 256 cooperates and moves over the first and the second raised camming surfaces 212, 214 of the jaws 16 (FIG. 32) in response to the distal movement of the driver bar 200 relative to the jaws 16.

Referring to a proximal end of the driver bar 200, the driver bar 200 is connected to the slider joint 202. The slider joint 202 has a number of latch retractors 158, 160 as shown in FIG. 34. Latch retractors 158, 160 extend perpendicular therefrom and are configured to extend through the windows 604, 604 in the wedge plate 600 shown in FIG. 33. These latch retractors 158, 160 limit a retraction and distal movement of the slider joint 202 relative to the jaws 16 as shown in FIG. 33. In one embodiment of the present clip applier 10, latch retractor 158 retracts while latch retractor 160 limits movement. Alternatively, latch retractor 160 may retract while the latch retractor 158 limits movement. In another embodiment, each latch retractor 158 and 160 can switch between functions of limiting movement and retracting. In still another embodiment, more than two latch retractors 158, 160 may be provided. Various configurations are possible and within the scope of the present disclosure.

Figure 35:
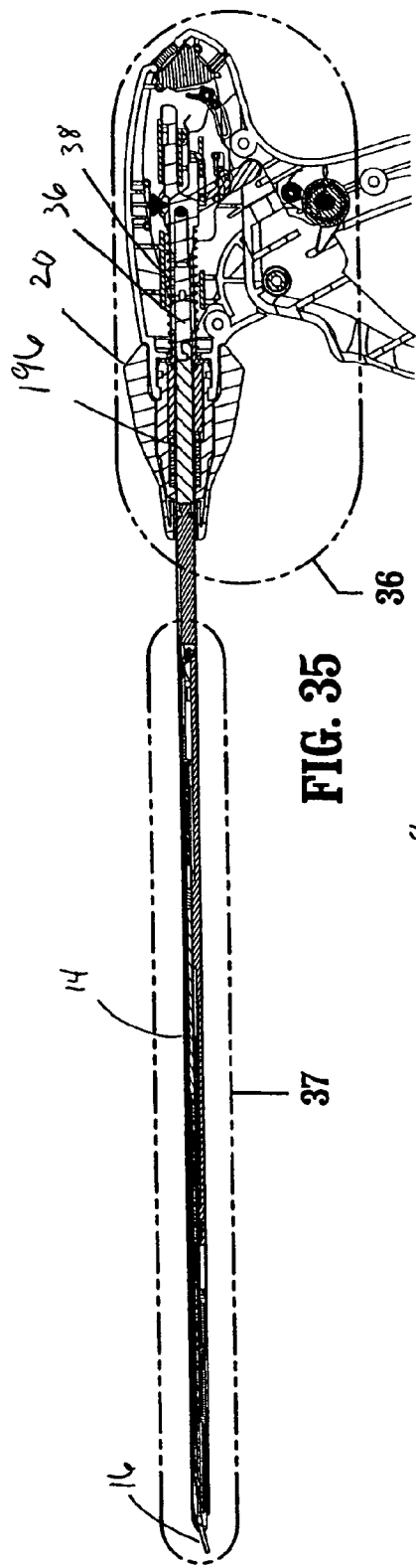
FIG. 35 is a side view, partially shown in section, of the surgical clip applier in a pre-fired condition.
Figure 36:
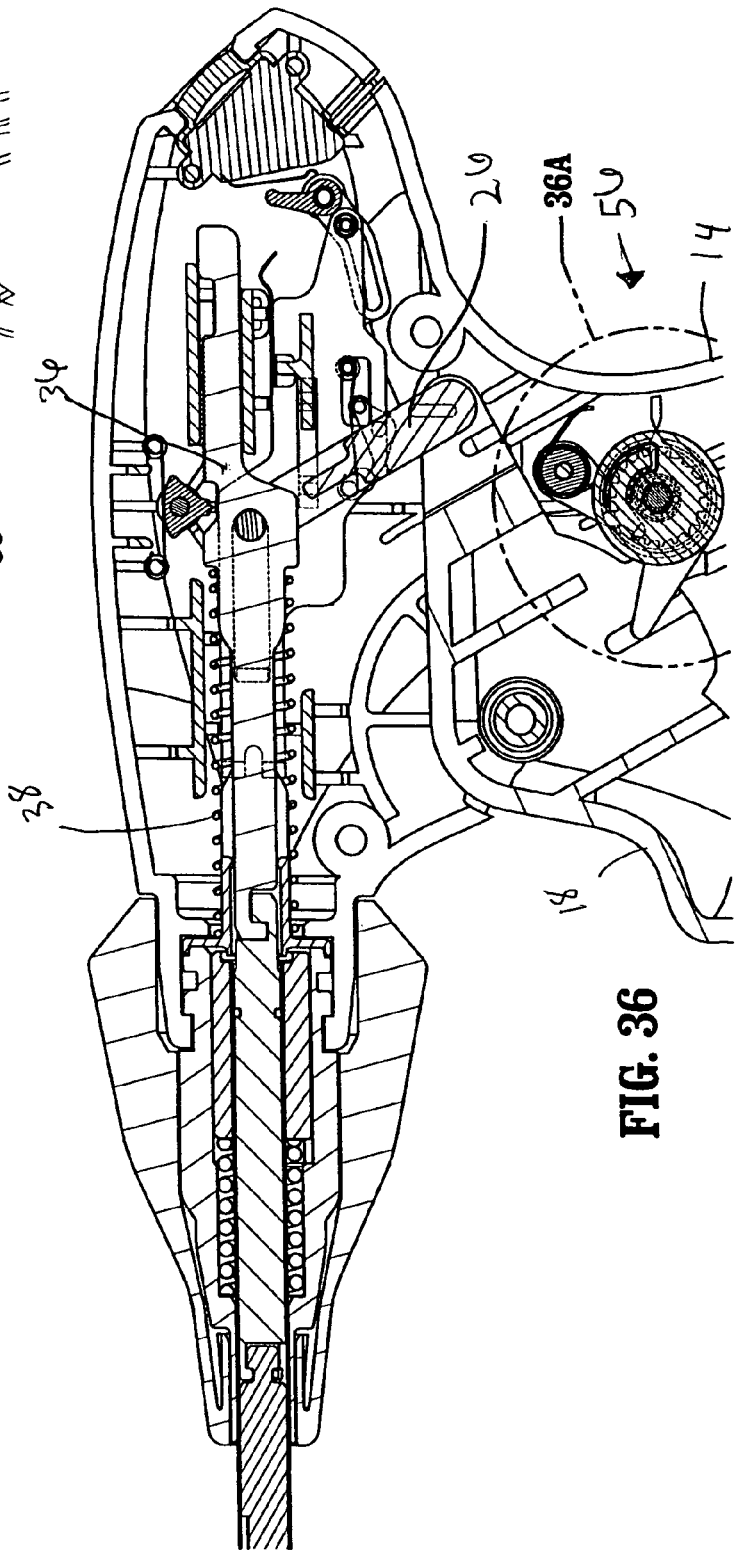
FIG. 36 is in enlarged area of detail of FIG. 35.

The operation of the surgical clip applier 10 to crimp a clip 300 around a target tissue, such as a vessel, will now be described. Referring now to FIG. 35 and FIG. 36, the trigger 18 is shown in an uncompressed state with the driving member 36 in an original position, and biased by the spring 38.

Figure 36A:
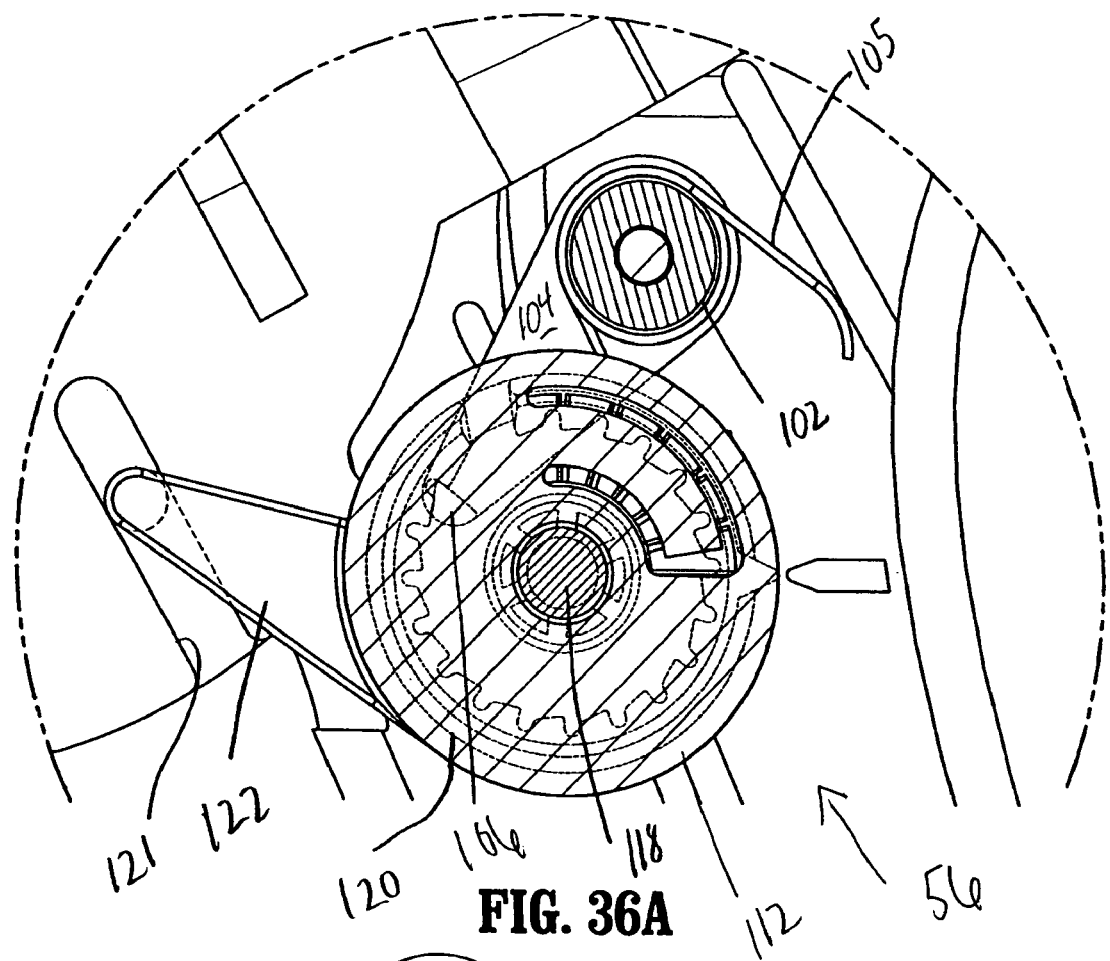
FIG. 36A is a first lateral side view of a lockout mechanism.

Referring to FIG. 36A, there is shown the lockout mechanism 56 of the surgical clip applier 10 with the lockout mechanism 56 in an original initial position. As shown in FIG. 36A, the arm 122 of the third rotatable member 120 has a portion that rests in a channel 121 of the handle assembly 12 as shown in FIG. 36A. The third rotatable member 120 mates with the lockout wheel 112 via post 118. In one embodiment, the third rotatable member 120 is an indexer wheel.

Figure 36B:
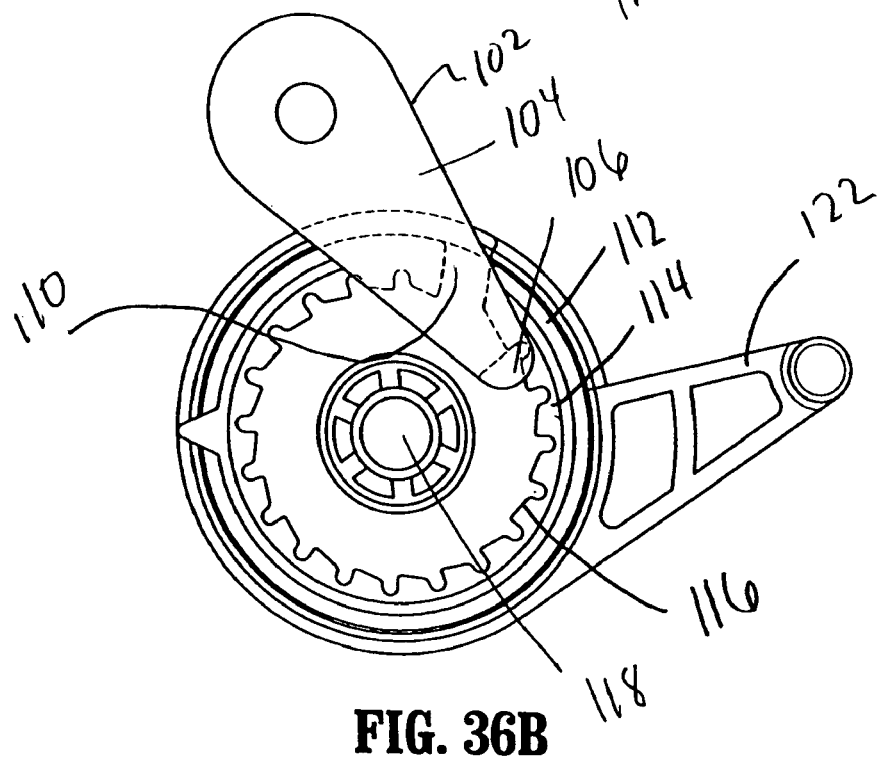
FIG. 36B is a second opposite lateral side view of FIG. 36A showing the lockout mechanism.

Referring to an opposite view shown in FIG. 36B, the inner circumference 114 of the lockout wheel 112 has a number of teeth 116 and the escape notch 110. The escape notch 110 is disposed at a position around the inner circumference 114. The first rotatable member 102 having the arm 104 and the pawl 106 is offset from the lockout wheel 112 and is disposed so that the pawl 106 selectively engages with the teeth 116 as the clip applier 10 is fired.

Figure 36C:
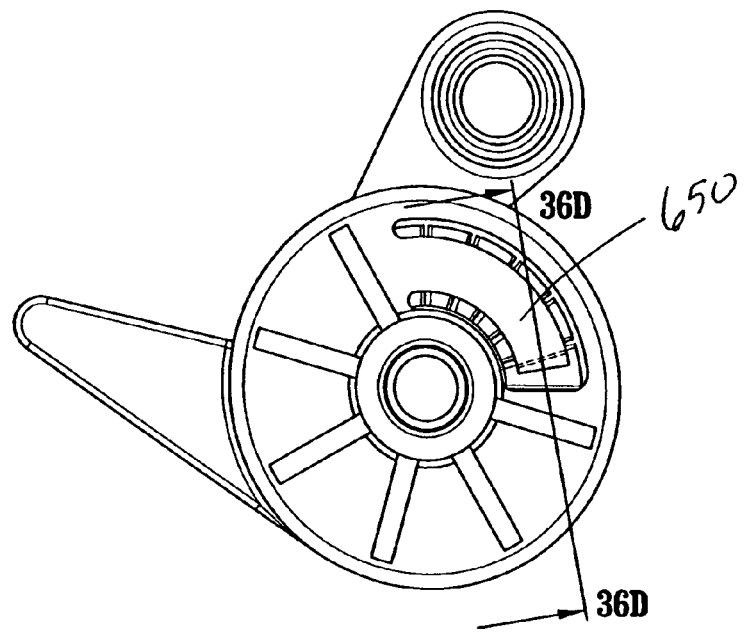
FIG. 36C is another first lateral side view of FIG. 36A showing the lockout mechanism having a ratchet arm.
Figure 36E:
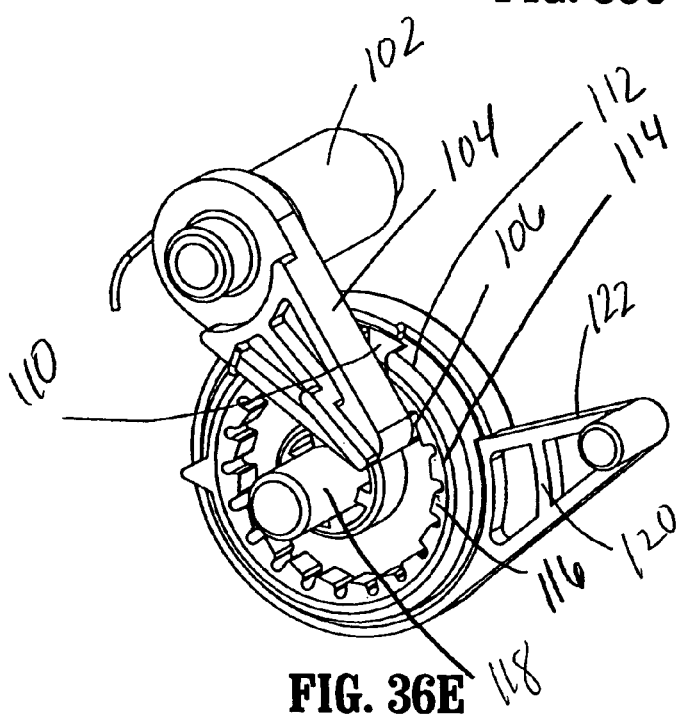
FIG. 36E is a perspective view showing a first rotatable member, a second rotatable member and a third rotatable member of the lockout mechanism.
Figure 36D:
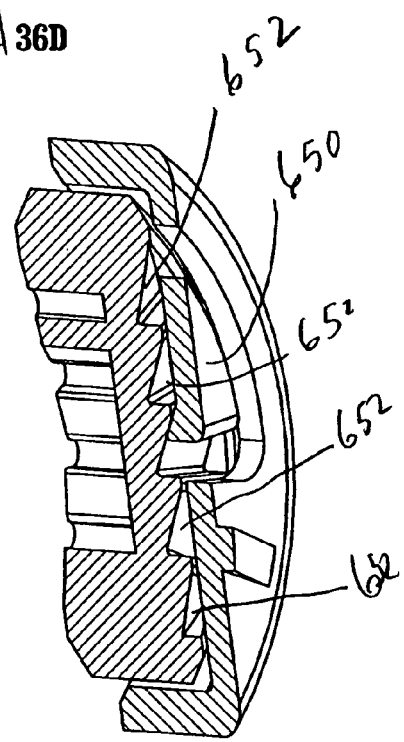
FIG. 36D is a cross sectional view of the lockout mechanism along line 36D-36D of FIG. 36C.
Figure 36F:
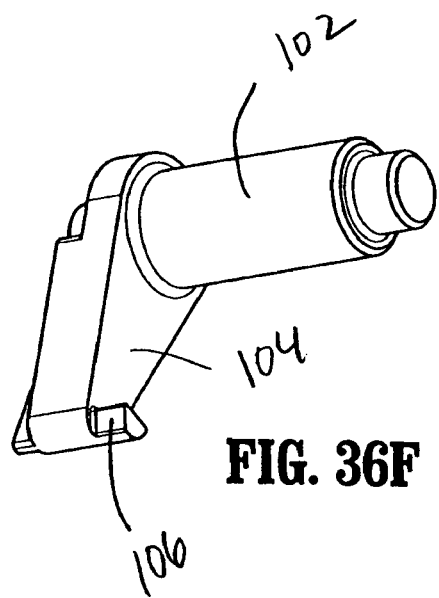
FIG. 36F is a perspective view of a first rotatable member of the lockout mechanism.
Figure 36G:
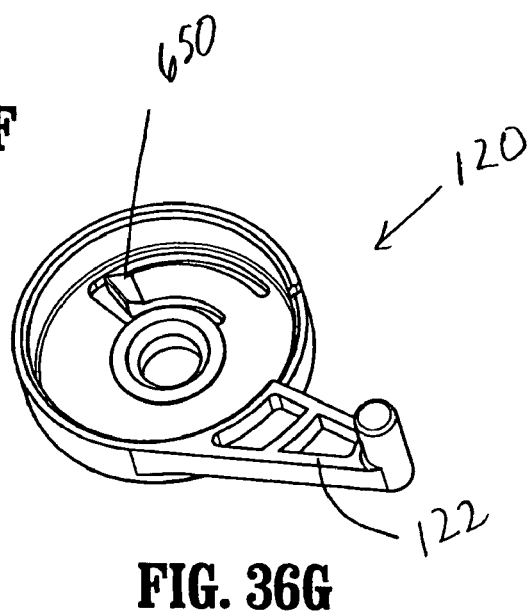
FIG. 36G is a perspective view of a third rotatable member of the lockout mechanism.
Figure 36H:
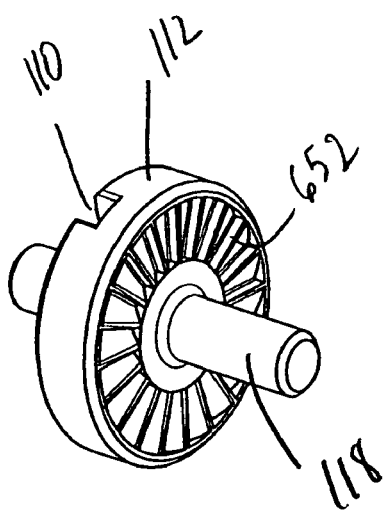
FIG. 36H is a perspective view of the second rotatable member of the lockout mechanism having a notch.
Figure 36I:
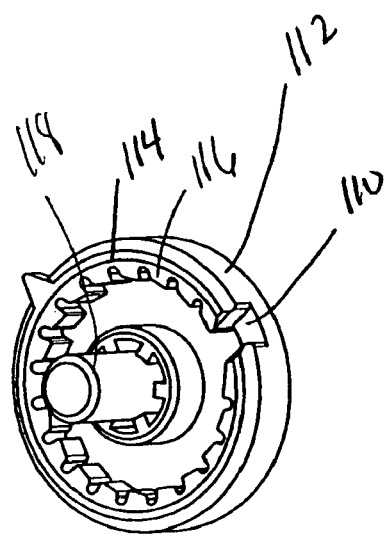
FIG. 36I is a perspective view of the second rotatable member of the lockout mechanism being opposite the view of FIG. 36H showing a number of teeth.

After the trigger 18 is fired the first rotatable member 102 will be radially advanced so that pawl 106 is urged to engage another tooth of the teeth 116. Referring to FIGS. 36C through 36E, the lockout wheel 112 has a predetermined number of teeth 116 complementary to the number of clips in the clip carrying channel 302 such that when the last clip is fired, the pawl 106 will be aligned with the escape notch 110 allowing the pawl 106 to enter escape notch 110 and be freed from the lockout wheel 112. Referring now to FIGS. 36c and 36d, and FIGS. 36F through 36I, the lockout mechanism 56 also has a ratcheting arrangement with a ratchet arm 650 and a number of ratchet teeth 652. The ratchet arm 650 of the third rotatable member 120 is designed to engage with ratchet teeth 652 and rotate the lockout wheel 112 clockwise in response to actuation of the trigger 18. Upon release of the trigger 18, the ratchet arm 650 thereafter is rotated in an opposite radial direction to move over each of the ratchet teeth so as to allow the ratchet arm 650 to move counterclockwise to reset to the original position after each clip 300 is fired while not disturbing the radial advancement of the pawl 106.

As best shown in FIGS. 37 through 42, and with reference to FIG. 38, in an unfired state the trip lever 500 is carried by the spindle 128. The trip lever 500 is biased by the trip lever spring 502. The trip lever 500 also is in contact with the proximal window 410 in the feed bar 400. The trip block 406 is in a distal position relative to the trip lever 500.

Figure 39:
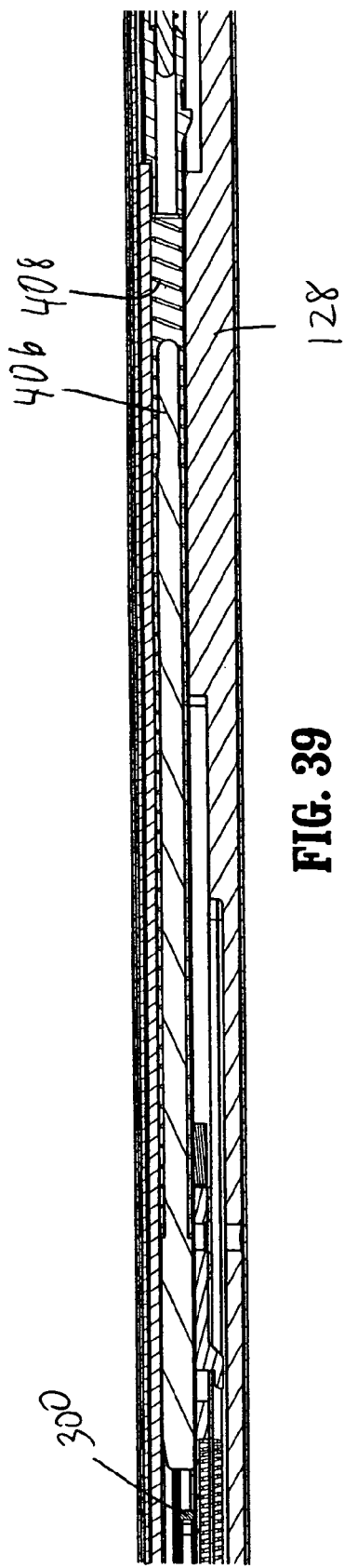
FIG. 39 is an enlarged area of detail of FIG. 37 showing the follower.

Referring now to FIG. 39, there is shown the follower 306 biased by the follower spring 408 in order for the clips 300 to be biased in the distal direction.

Figure 40:
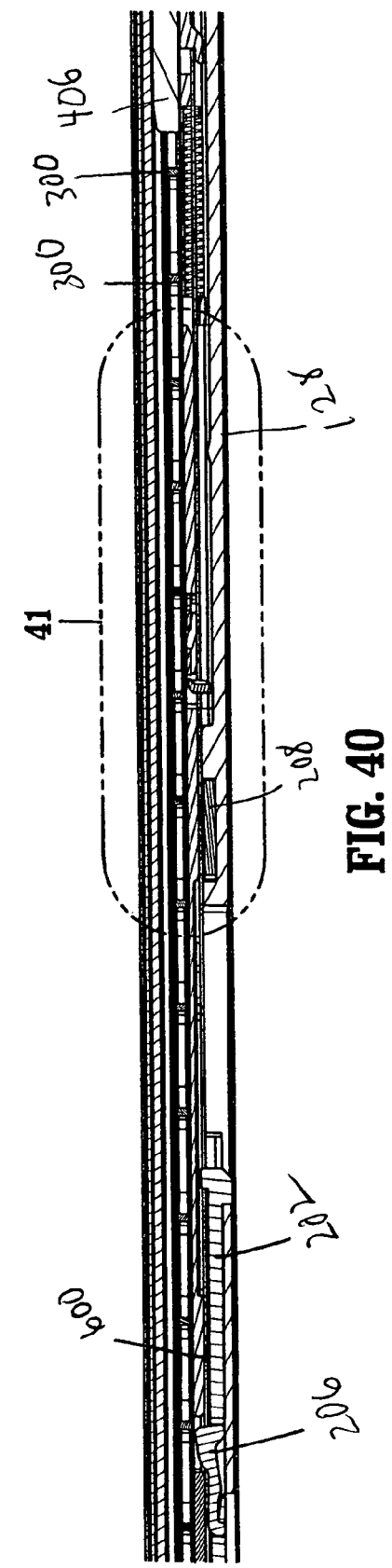
FIG. 40 is a side view, shown in section, of the distal end of the surgical clip applier of FIG. 37 having a cam link.

Referring now to FIG. 40, there is shown another cross sectional view of the spindle 128 having the cam link 208 and the wedge plate 600 resting on the spindle 128. The slider joint 202 is disposed under the wedge plate 600 with the latch member 206 disposed in the slider joint 202. The spindle 128 drives the cam link 208 distally an initial distance such that the cam link boss 230 on the cam link 208 engages the cam slot 612 in the wedge plate 600.

Referring to FIGS. 41 and 41A, there is shown another cross sectional view of the outer tube 14 having the filler component 700. The wedge plate 600 is disposed under the filler component 700 with the rotatable member 702 extending therebetween.

The wedge plate 700 has the spring bar member 704 that is disposed in the aperture 706. The spring bar member 704 biases the rotatable member 702 and can deflect at its free end. The rotatable member 702 is disposed distal relative to the camming feature 210 of the spindle 128 that is beneath the filler component 700 shown in dotted lines. Once driven distally, the spindle 128 will advance. The spindle 128 will advance the camming feature 210. The camming feature 210 will be driven distally and will deflect the rotatable member 702 in a clockwise manner.

Referring to FIG. 41B, there is shown a cross sectional view of the spindle 128 showing the various components therein along line 41B-41B of FIG. 41. The clip 300 rests in the clip channel 302 and has the feed bar 400 on a top side thereof. The wedge plate 600 is disposed underneath the filler component 700 as shown and above the spindle 128. The clip channel cover 310 is disposed above the clip channel 302.

The pusher 414 advances each of the clips 300 into the clip channel 24 as shown in FIG. 42A. Spindle 128 shown in an unfired state in FIG. 42. The spindle 128 is disposed to connect to the slider joint 202. When the clip applier 10 is being fired, the spindle 128 moves distally. At a predetermined distance, latch member 206 is mechanically forced to cam down and engages channel 250 of the spindle 128 (which is best shown in FIG. 11) in the direction of reference arrow L shown in FIG. 73. This allows the slider joint 202 to move with the driver bar 200 (when driven) distally. The driver bar 200 thus can engage the relevant surfaces to close the jaws 16 around the clip 300 disposed in the channel 24 between the jaws 16.

Referring now to FIG. 43, there is shown a perspective view of the wedge plate 600 and the jaws 16 in an original proximal most position. The wedge plate 600 has the wedge plate spring 602 in the window 604 around the tongue 606. The wedge plate 600 further has a "C" shaped window 610 to engage the rotatable member 702. The cam link 208 is in a proximal-most position relative to the cam slot 612.

Referring to FIGS. 44 through 46, the wedge plate 600 also has the rounded distal end 616 engageable with the cam features 23a, and 23b to separate the first jaw 16a and the second jaw 16b slightly as shown later for loading.

Referring to FIG. 47, the cam link 208 is initially disposed in the cam slot 612 in the initial proximal position with the filler component 700 disposed below the cam link 208 in this view. Referring to the "C" shaped window 610 as shown on the proximal portion of the wedge plate 600, the rotatable member 702 has the second end 710 extending through the "C" shaped window 610. The first end 708 of the rotatable member 702 contacts the spring bar member 704 on the filler component 700 that is beneath the wedge plate 600.

Referring to FIG. 48, to initiate actuation of the clip applier 10, the trigger 18 is moved through an initial swing as shown by arrow C such that the wishbone link 26 drives the driving member as shown by arrow D. Referring to FIG. 49, the rack 40 on the driving member 36 begins to slide under the pawl 46 as shown by reference arrow E and the pawl 46 rotates to deflect pawl return spring 48 by reference arrow F.

Referring now to FIG. 49A, the signaling device 54 is shown. The signaling device 54 also has an internal rib 2 that is integral with the handle assembly 12. The click lever 78 contacts the click lever spring 80 and upon being recoiled from the spring 80, the click lever 78 will have the bulbous portion 190 of the click lever 78 contact the internal rib 2.

Upon contacting the internal rib 2, the bulbous portion 190 and the internal rib 2 will resonate thereby providing the surgeon with the audible indication of clip firing. Contemporaneously, as the driving member 36 and the rack 40 advance distally the pawl 46 rotates as shown in FIG. 50. If the trigger 18 were released at this point, the rack 40 would restrain the pawl 46 against any proximal motion and thus prevent release of the trigger and any partial or inadvertent partial actuation of the trigger 18.

Also, as shown in FIG. 50A, the lockout wheel 112 of the lockout device 56 also rotates and has the pawl 106 contacting the teeth 116 on the inner circumference 114 of the lockout wheel 112. As shown, the pawl 106 will advance from a first tooth space 3 to a next tooth space 5 once clip 300 is fired. If another clip 300 is fired, the pawl 106 will rotate from space 5 to space 7 and continue to advance in a counterclockwise manner until the pawl 106 reaches the escape notch 110 once the last clip 300 has been fired. The surgical clip applier 10 is loaded with a number of clips 300 that always exceeds a number of teeth of the lockout wheel 112 to ensure that the surgical clip applier 10 will never dry fire or in other words cannot fire without a clip 300.

Figure 51:
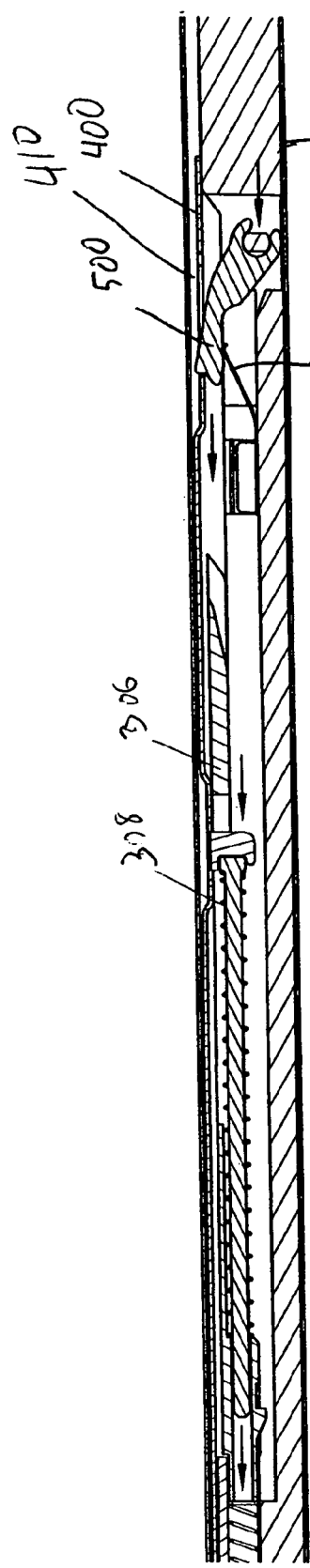
FIG. 51 is a side view, shown in section, of the feed bar and trip lever.
Figure 52:
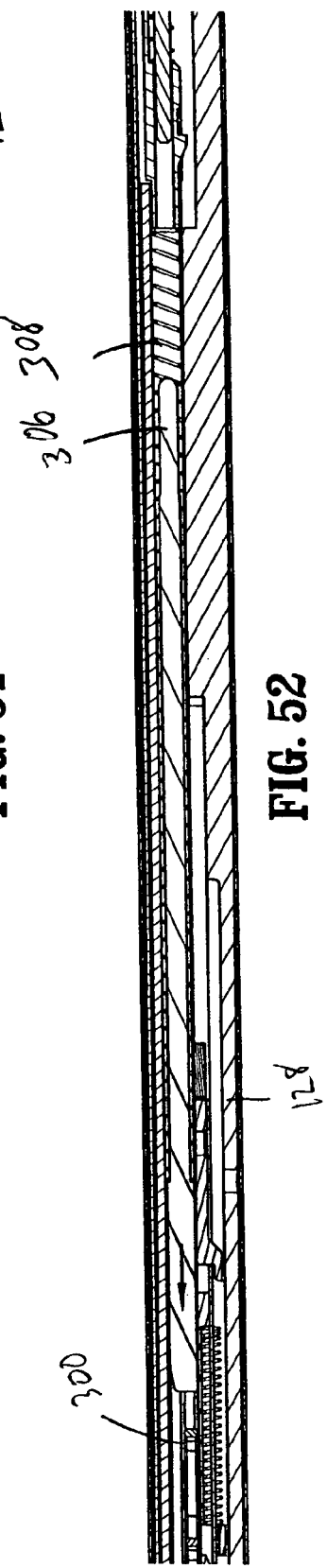
FIG. 52 is a side view, shown in section, of the follower.

Referring to FIG. 51, during the initial stroke, the spindle 128 moves a predetermined distance. As the spindle 128 moves a predetermined distance distally, the trip lever 500 that this biased by the trip lever spring 502 moves distally and the feed bar 400 is driven distally by the trip lever 500 engaging the feed bar window 410. Referring now to FIG. 52, as a distal most clip 300 is moved into the channel 24 of the jaws 16 by pusher 414, the follower 306 then moves in a distal direction and is urged forward by the follower spring 308. The follower 306 moves each of the clips 300 in a distal manner to be loaded individually into the channel 24 of jaws 16.

Figure 53:
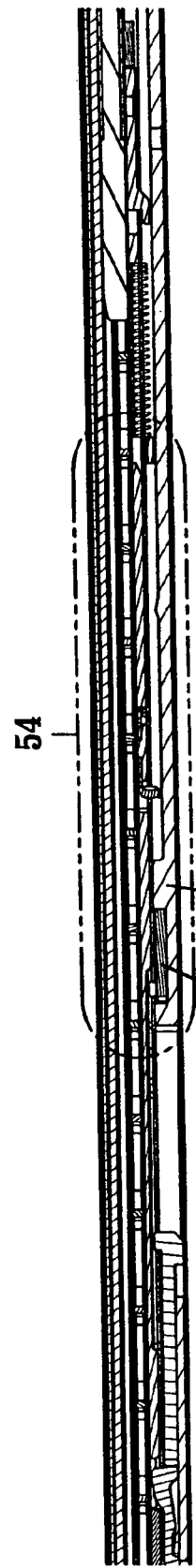
FIG. 53 is a side view, shown in section, of the endoscopic portion of the surgical clip applier with the spindle and the cam link.

Referring now to FIGS. 53 through 55, there is shown a cross sectional view of the various components of the clip applier 10 during the initial stroke with the filler component 700, wedge plate 600, and the cam link 208. As the spindle 128 moves distally, the boss 230 on the cam link 208 contacts the cam surface 614 on the cam slot 612 of the wedge plate 600 as shown in FIG. 55. The cam link 208 moves distally with the spindle 128 and the cam surface 614 is also urged distally relative to the filler component 700.

Referring now to FIG. 56, the pusher 414 urges and advances an individual clip 300 into the channel 24 of the jaws 16 while at an opposite end, the spindle 128 has a suitable geometry such that the spindle 128 has not contacted the driver bar 200 in order to actuate and close the jaws 16.

Referring to FIG. 57, as the cam link 208 is advanced distally, the cam link 208 engages the cam surface 614 of the cam slot 612 to move the wedge plate 600 distally relative to the filler component 700. Contemporaneously, the "C" shaped window 610 also advances distally, and a lateral surface 625 contacts the second end 710 of the rotatable member 702. The lateral surface 625 of the wedge plate urges the rotatable member 702 to rotate counterclockwise as shown. The first end 708 of the rotatable member 702 upon rotation contacts the spring bar member 704 on the filler component 700 and causes the spring bar member 704 of the filler component 700 to deflect.

Referring to FIG. 58, the feed bar 400 continues to urge the pusher 414 with the sloping surface to contact a single clip 300. The pusher 414 continues to introduce the clip 300 into the clip channel 24. At the same time, the wedge plate 600 continues to advance and be driven distally by the cam link 208 urging the cam surface 614 of the cam slot 612 as shown by the reference arrow.

FIG. 59 shows that the spring bar member 704 after being deflected by the rotatable member 702 recoils in a direction of reference arrow G. The recoil moves the rotatable member 702 clockwise so the second end 710 contacts a lateral side 626 of the "C" shaped window 610 as shown by reference arrow H. The rotatable member 702 thus conveniently holds the wedge plate 600 in a most distal position and completely controls a position of the wedge plate 600 for loading.

The cam link 208 at this most distal position of FIG. 59 contacts the camming feature or the disengaging cam surface 726 of the filler component cam slot 720 on the filler component 700. The cam link 208 is now cammed out of engagement with the cam surface 614 and the wedge plate 600 is at its most distal position, and the cam link 208 no longer drives the wedge plate 600 distally.

Referring to FIGS. 60 and 61, the rounded distal end 616 of the wedge plate 600 is now moved in between the camming surface 23a, 23b of the first and the second jaw components 16a, 16b as shown. The rounded distal edge 616 of the wedge plate 600 thus moves the first and second jaw components 16a, 16b opposite from one another as shown for gently increasing a size of the channel 24. This additionally restrains each of the jaw members 16a, 16b from flexing with regard to one another preventing any torque on the clip 300 as it is being inserted between the jaws 16 as shown by the reference arrows.

As best show in FIG. 62, the cam link 208 continued to advance distally in the cam slot 612 while the wedge plate 600 is held by the rotatable member 702 at the second end 710. Rotatable member 702 is held by the spring bar member 704 at the second end 710 between the spring bar member 704 and a lateral wall of the aperture 706 of the filler component 700. Referring to FIG. 63, the spindle 128 continues to move distally through the stroke, and the trip lever 500 is urged distally with the spindle 128.

At the proximal end of the feed bar 400, the camming surface of the feed bar 400 and the trip lever 500 are cammed out of engagement relative to one another. The trip lever 500 is cammed out of engagement relative to the window 410 of the feed bar 400 by the toothed member 420 of the trip block 406. This allows the feed bar 400 to return to a proximal initial position due to the biasing of the feed bar 400. Thus, the loading of the clip 300 into the channel 24 is complete and the feed bar 400 is retracted back to an initial position by spring tension.

Referring to FIG. 64, the distal portion of the feed bar 400 is shown completing the loading of the clip 300, and thereafter retracts to an initial proximal location of the clip applier 10.

As best shown in FIGS. 65 and 65A, there is shown a bottom view of the wedge plate 600 (FIG. 65), and a top view the filler component 700 (FIG. 65A), and the spindle 128 shown in dotted lines. The spindle 128 has the camming feature 210 or edge that contacts the second end 710 of the rotatable member 702 as the spindle 128 advances distally. As shown from the opposite view, the camming feature 210 is advanced distally and deflects the rotatable member 702 in a counterclockwise manner. The rotation causes the first end 708 of the rotatable member 702 to likewise deflect the spring bar member 704 of the filler component 700. Notably, the rotatable member 702 is no longer holding the wedge plate 600 and the wedge plate 600 is permitted to retract by spring torsion.

Figure 66:
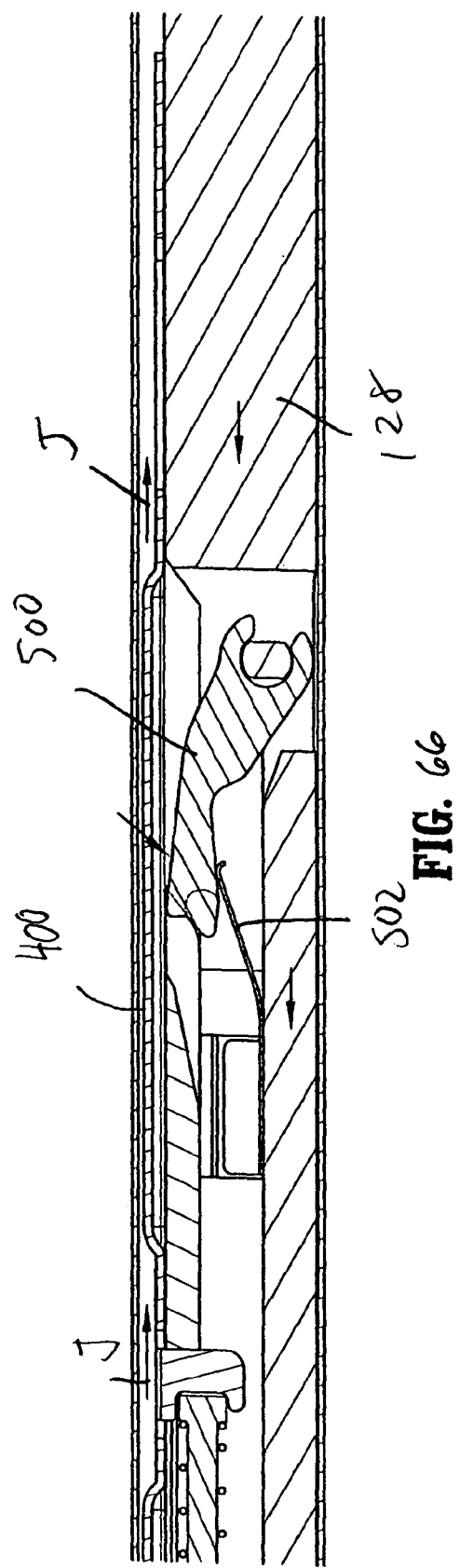
FIG. 66 is a side view, shown in section, illustrating the trip lever being cammed out of engagement with the feed bar.

Referring now to FIG. 66, as being moved distally by the spindle 128, the trip lever 500 is cammed out of engagement with the feed bar window 410. This permits the feed bar 400 to retract in a proximal direction as shown by arrow J. The spindle 128 continues to advance distally during the stroke.

Figure 67:
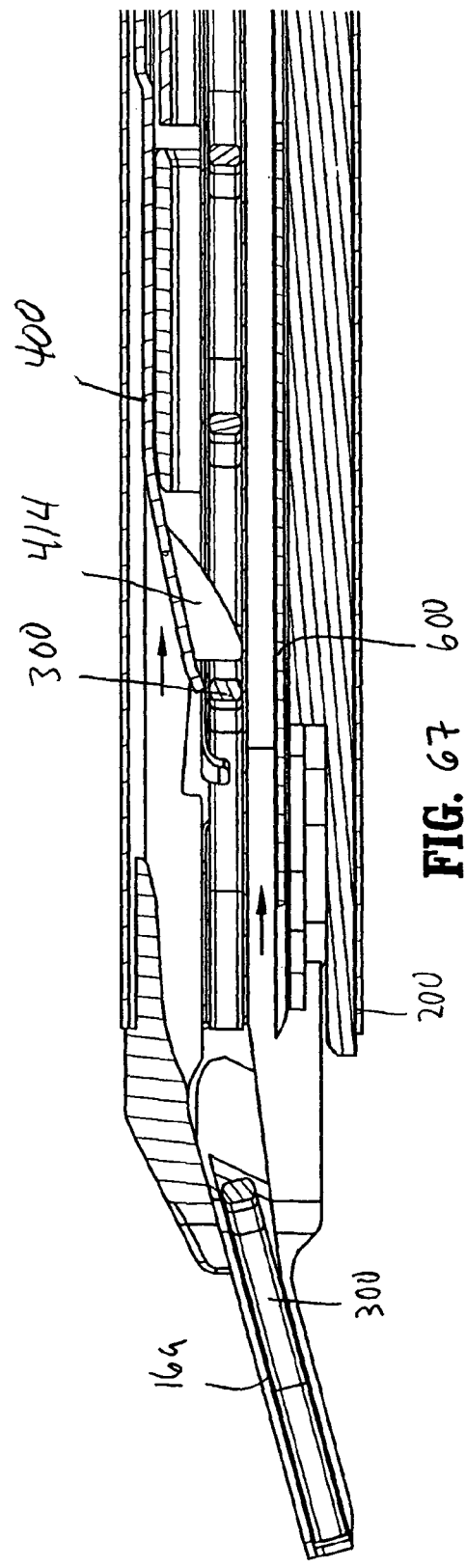
FIG. 67 is a side view, shown in section, illustrating the retraction of the wedge plate and feed bar.

Referring to FIG. 67, there is shown the clip 300 inserted into the channel 24 between the jaws 16. As best shown in FIG. 67, the feed bar 400 now retracts after reaching a most distal position to the next clip 300 and the loading is completed. The trip lever 500 is cammed out of engagement with the feed bar 400 and this allows the pusher 414 to retract proximally. As shown in FIG. 67, the feed bar 400 retracts so the nose of the pusher 414 aligns to an initial position for loading the next clip 300 of the number of clips into the channel 24.

Referring now to FIG. 67A, there is shown a cross sectional view of the handle assembly 12. The trigger 18 is being fired by the surgeon and typically is grasped and pulled in a direction of reference arrow A. The trigger 18 moves the wishbone link 26 that advances to the end of the longitudinal window 60 of the actuator plate 50. The actuator plate 50 driven distally moves the protrusion 70 link to the LCD lever 52 that contacts a suitable LCD contact 100 on the LCD unit 96 to change the display on the LCD display 98 and/or change the displayed parameter. The wishbone link 26 also drives the driver member 36 distally to advance the spindle 128.

The signaling device 54 is also driven by the actuator plate 50 and has the click lever 78 commencing to rotate to contact the rib 2 of the handle assembly 12.

Figure 68:
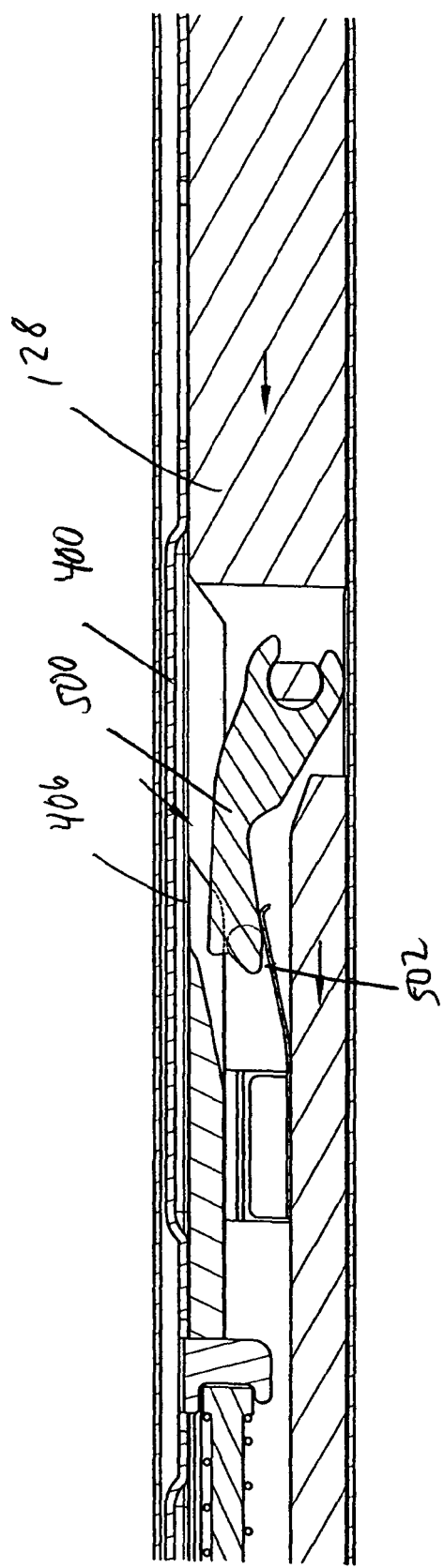
FIG. 68 is a side view, shown in section, illustrating further advancement of the spindle.

Referring now to FIG. 68, as the stroke progresses, the spindle 128 and the trip lever 500 continue to move distally, and the trip lever 500 is completely cammed down to be underneath the trip block 406 so the feed bar 400 is disengaged from the trip lever 500 and the feed bar can retract proximally behind the nest most distal clip in the clip channel 302.

Figure 69:
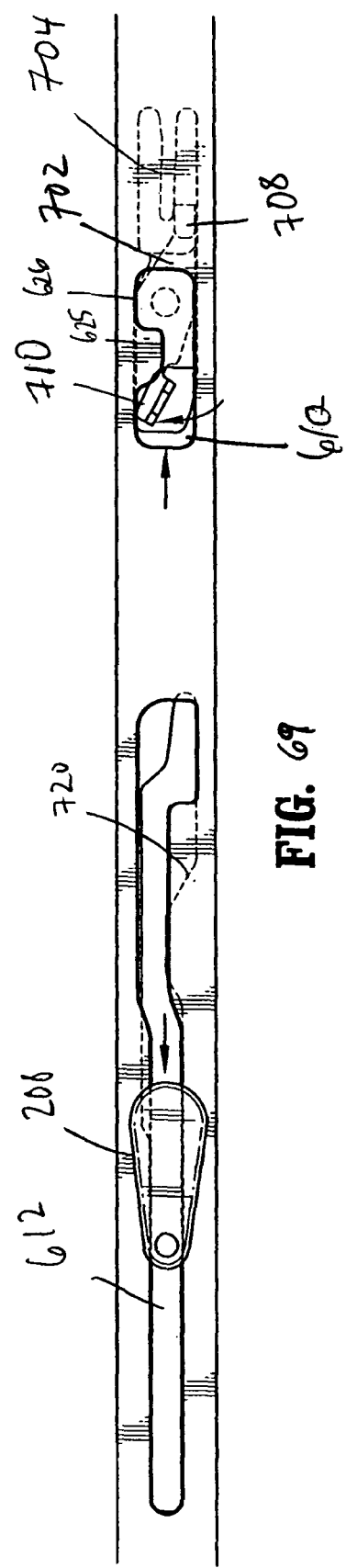
FIG. 69 is a side view, shown in section, illustrating the retraction of the wedge plate and further advancement of the spindle.

Referring to FIG. 69, there is shown a top view of the wedge plate 600. As discussed previously, the spindle 128 continues to moves the cam link 208 distally through the cam slot 612. Referring to the "C" shaped window 610 of the wedge plate 600 and the filler component 700 shown above the wedge plate 600, there is shown the rotatable member 702. The rotatable member 702 has a first proximal end 708 and an opposite second distal end 710. The second distal end 710 of the rotatable member 702 snaps back into the more distal region of the "C" shaped window 610. The spring bar member 704 deflects and returns to an original position.

Referring to FIG. 70, the rounded distal end 616 of the wedge plate 600 is retracted from the jaws 16 after loading and moves in a proximal position. As shown in FIG. 70, the clip 300 rests in the channel 24 of the jaws for application of a compressive force by the jaws.

Referring to FIG. 71A, the actuator plate 50 in the handle portion 12 continues to move distally urging audible click lever 78 to rotate counterclockwise. The audible click lever 78 is then deflected by the click spring 80. Referring to FIG. 71, the latch member 206 is cammed in a direction toward the spindle 128 so the driver bar 200 can now be engaged and move distally to apply the required compressive force. The driver bar 200 is engaged by the spindle 128. The driver bar 200 is driven distally to force jaw legs 16a and 16b toward one another so as to compress clip 300 on a vessel.

Figure 72:
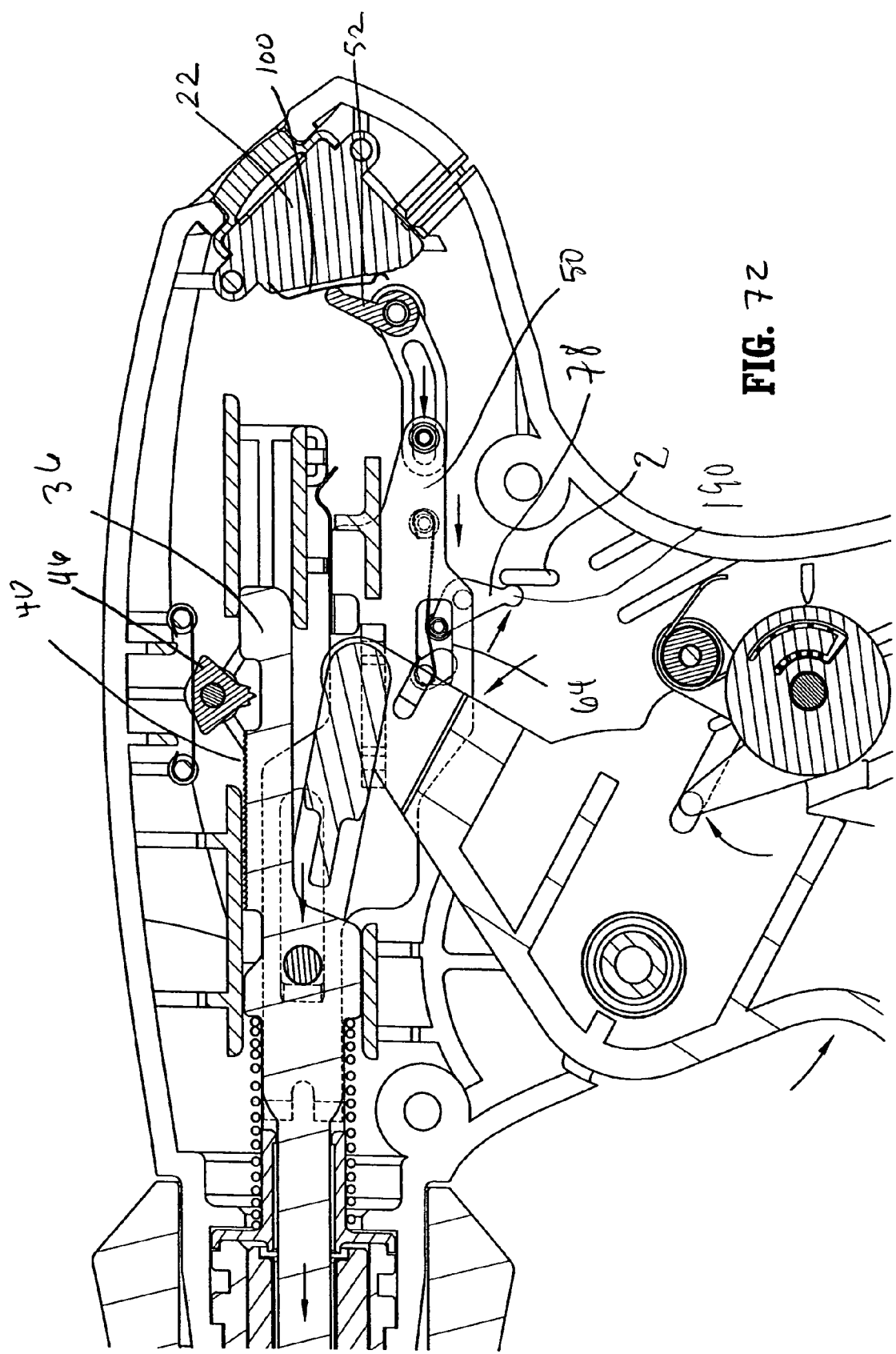
FIG. 72 is a side view of the handle housing with the trigger at full stroke.

Referring to FIG. 72, there is shown a cross sectional view of the handle assembly 12 during a full stroke. The pawl 46 resets itself so that the instrument can retract and reset when the trigger 18 is released. The rack 40 on the driving member 36 is cleared from the pawl in the full stroke position.

Notably, the audible click lever 78 contacts the rib 2 of the housing of the handle 12 by having the bulbous portion 190 sharply contacting the rib 2 making a loud and audible clicking sound. The audible click lever 78 is rotated by the actuator plate 50 that is moved distally by the driving member 36.

Referring to FIG. 73, there is shown the cross sectional view of the endoscopic portion at the full stroke. A full stroke of the spindle 128 is required to take a clip 300 from an initial position to a fully inserted position in the jaws 16. The spindle 128 driven to a distal most position moves the driver bar 200 to crimp the clip.

FIGS. 74 through 76 show the driver bar 200 having the camming surfaces 256 that engage other the first and the second raised camming surfaces 214, 216 being on each of the jaws 16a, 16b. The driver bar 200 rides the raised surfaces to close the jaws 16 with the clip 300 in the channel 24. As shown in cross section along line 76-76 of FIG. 75, FIG. 76 shows the driver bar 200 with a "T" shaped channel that closes over the camming raised surfaces 212, 214 of the jaws 16 to apply a compression on the clip 300 in the channel 24.

Figure 77:
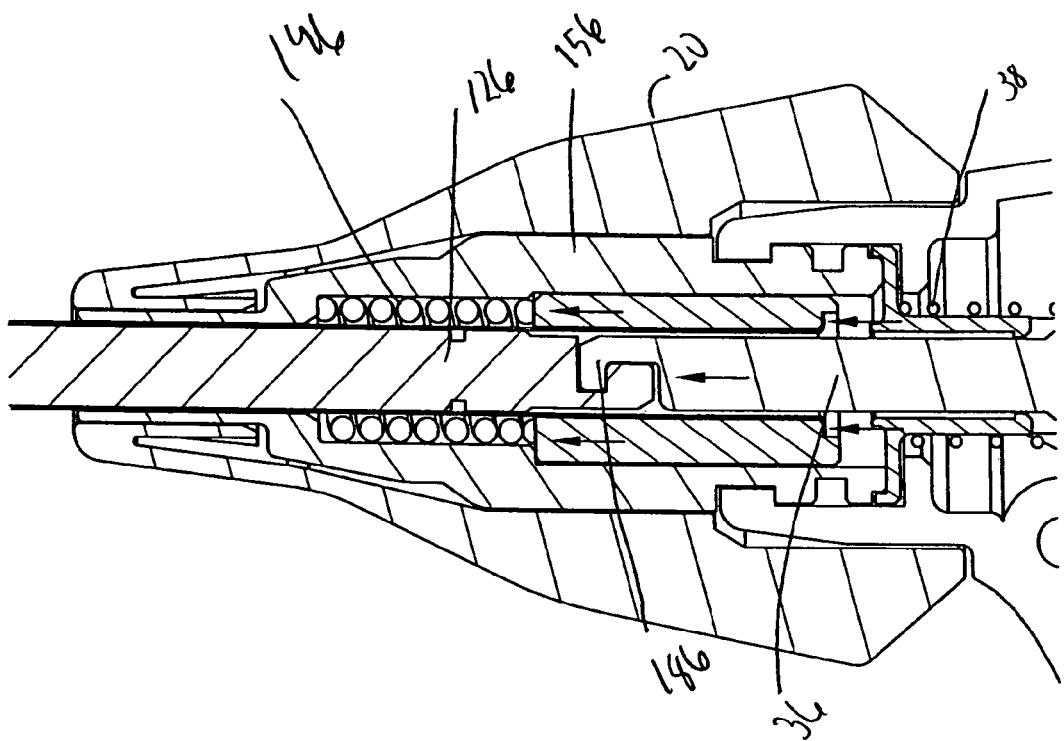
FIG. 77 is a view, shown in section, of the overpressure mechanism including the impact spring.
Figure 78:
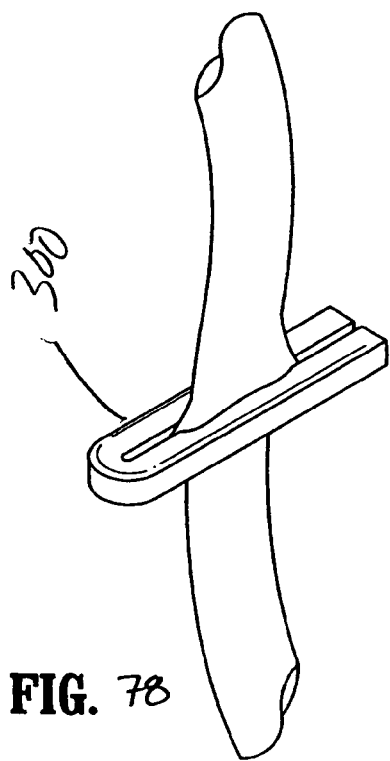
FIG. 78 is a perspective view of a surgical clip formed on a vessel.

Referring to FIG. 77, the clip applier 10 has a security mechanism being provided to prevent an over stroke or excessive compression of the clip 300 in the channel 24 by the jaws 16 by squeezing. Such an excessive compression may cause one or more detriments such as an excessive compression of the clip 30 or damage to the driver bar 200, or the jaws 16. If the trigger 18 is continued to be squeezed past a full stroke required for a full forming of a clip 300 as shown in FIG. 78, the impact spring 196 of FIG. 77 compresses in the spaced defined by the knob 20 and the bushing 156. The impact spring 196 prevents any further distal movement of the spindle 128 by absorbing force beyond what is required to close a clip on a vessel.

Once the trigger 18 is released as shown in FIG. 79, the pawl 46 rotates against the bias of the pawl return spring 48 so the pawl tooth 178 ride along the rack 40 to reset the handle assembly 14 as shown by the reference arrow K. The drive member 36 retracts to reset. The rack 40 on the drive member 36 moves proximally and back under the pawl 46.

Referring to FIG. 80, the spindle 128 retracts to a proximal position and the latch member 206 is driven upwards opposite the spindle 128. Referring to FIGS. 81 through 86, the spindle 128 having the camming feature 210 retracts proximally and contacts the rotatable member 702 that rotates first proximal end 708 of the rotatable member 702 to contact the spring bar member 704 of the filler component 700.

Referring to FIG. 82, as the spindle 128 retracts in a proximal position, the cam link 208 moves again through the cam slot 612 in the wedge plate 600. The spindle 128 continued to retract proximally and the cam link 208 as shown in FIGS. 82 and 83 is drawn proximally and resets and is cammed to an original position.

It should be understood that the wedge plate 600 does not retract as it has fully retracted already, and the proximal movement by the spindle 128 causes the cam link 208 to return to its original position. In this position, the clip applier 10 is again in an initial position to be refired and this to attach to another clip 300 to a vessel.

Figure 84:
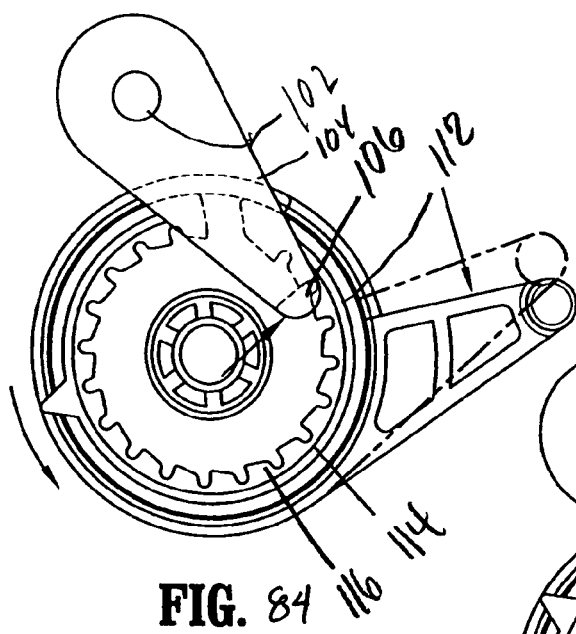
Figure 85:
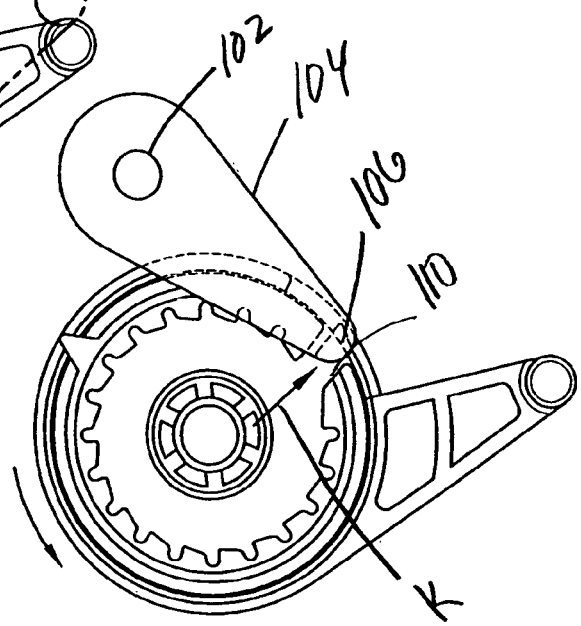
Figure 86:
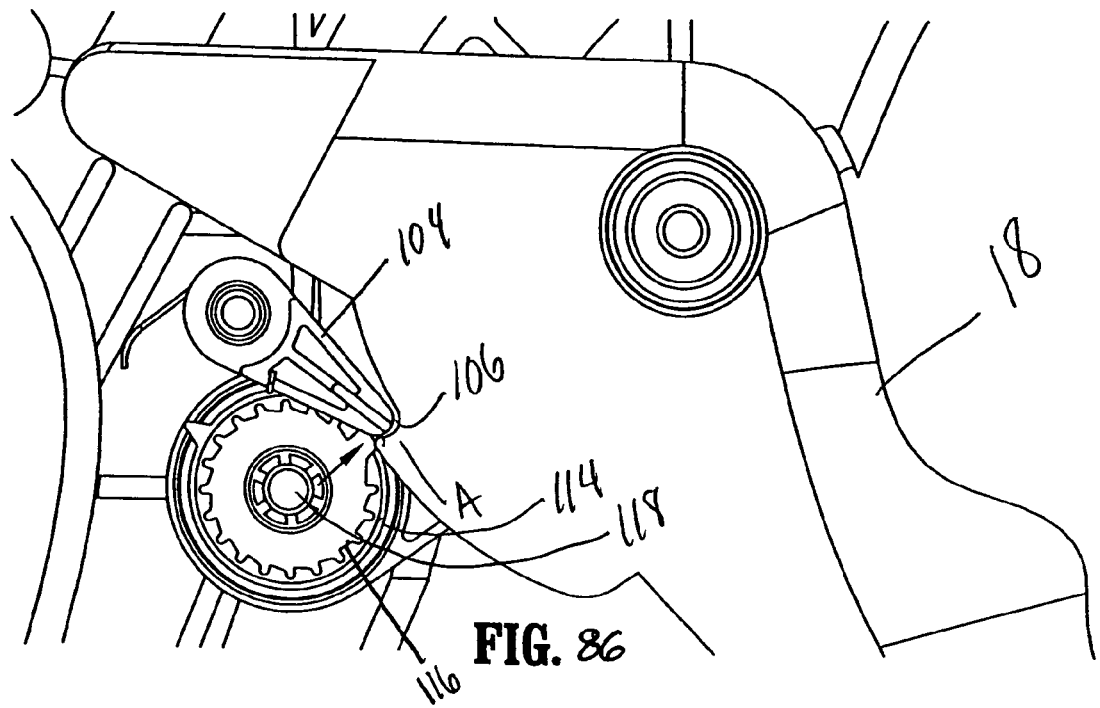

Referring now to FIGS. 84 through 86, the first rotatable member 102 will continue to ratchet through the teeth 116 of the lockout wheel 112. The lockout wheel 112 will progress and radially advance after each of the clips 300 is fired. As shown in FIG. 85, the first rotatable member 102 will rotate until the pawl 106 will reach the escape notch 110 in the lockout wheel 112. The escape notch 110 will then allow the pawl 106 to traverse out from the lockout wheel 112 as shown by arrow K in FIG. 85.

Referring to FIG. 86, the pawl 106 will then mate with a corresponding notch (A) shown in the trigger handle 18. Upon the pawl 106 mating in the notch A, the clip applier 10 will be locked and the pawl 106 will prevent any further firing or driving of the driving member 36 by the trigger 18. Thereafter, the clip applier 10 may be disposed in a suitable receptacle. Most preferably, the clip applier 10 is loaded with a number of clips 300 that exceed the number of teeth in the lockout wheel 112. To this end, the clip applier 10 cannot be dry fired without a clip therein.

Figure 87:
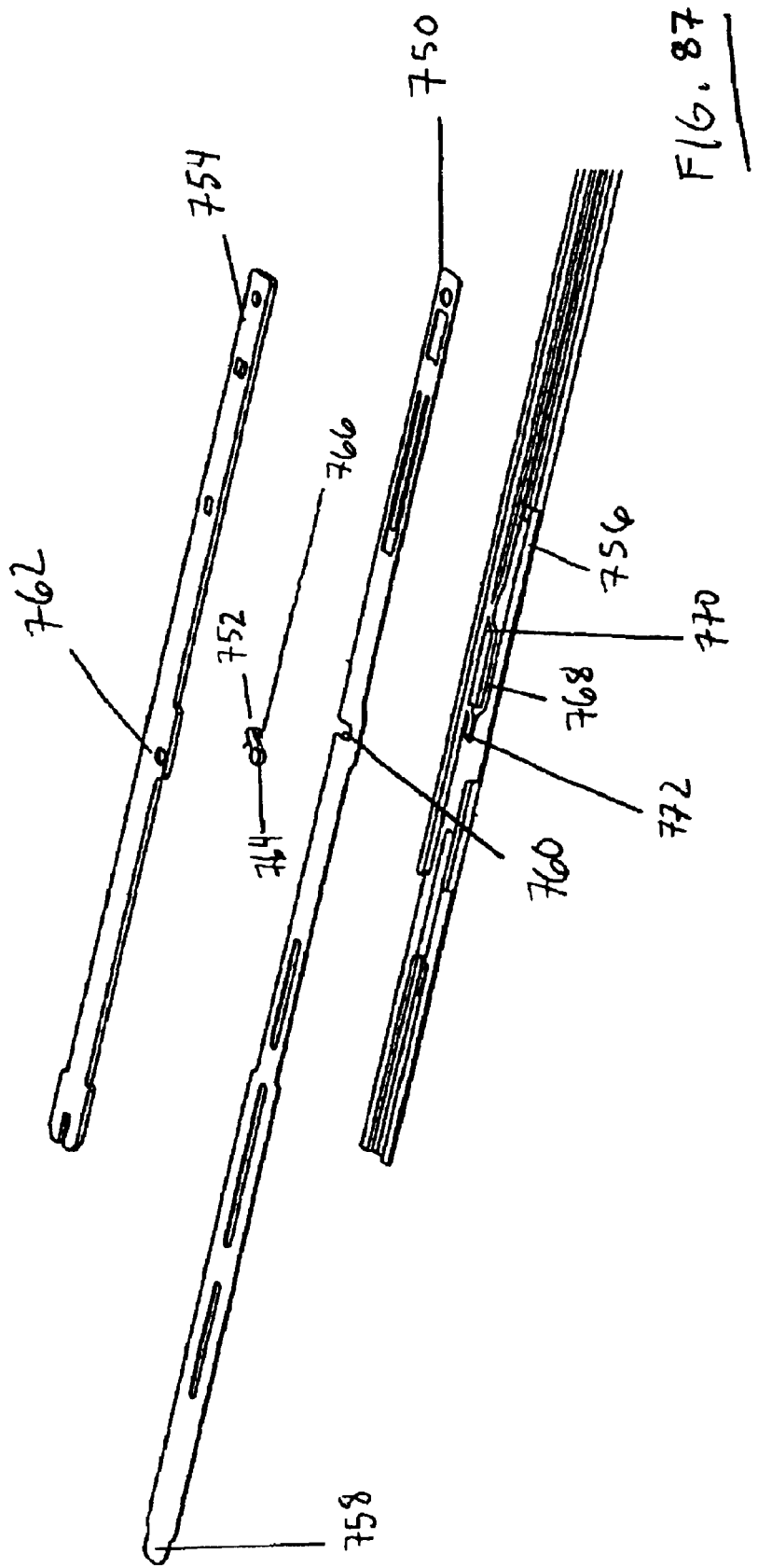
Figure 88:
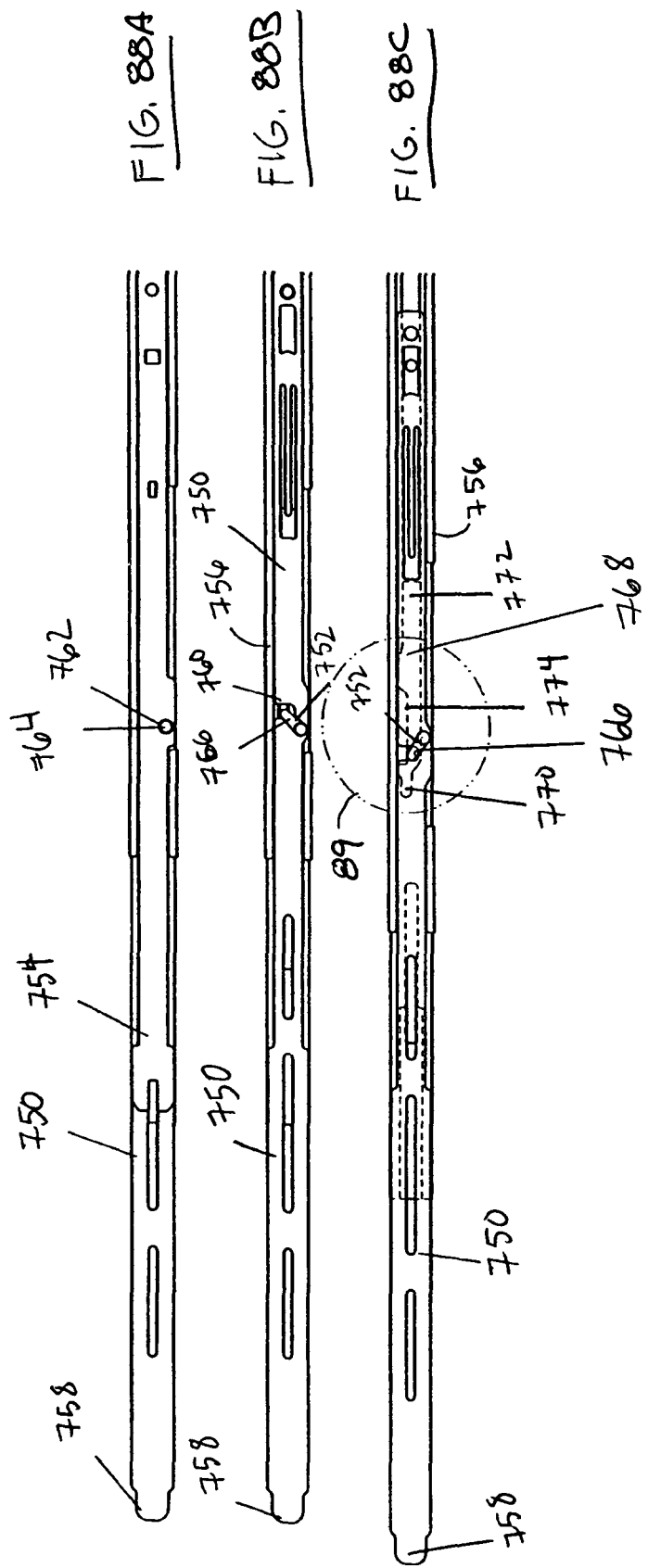
Figure 89:
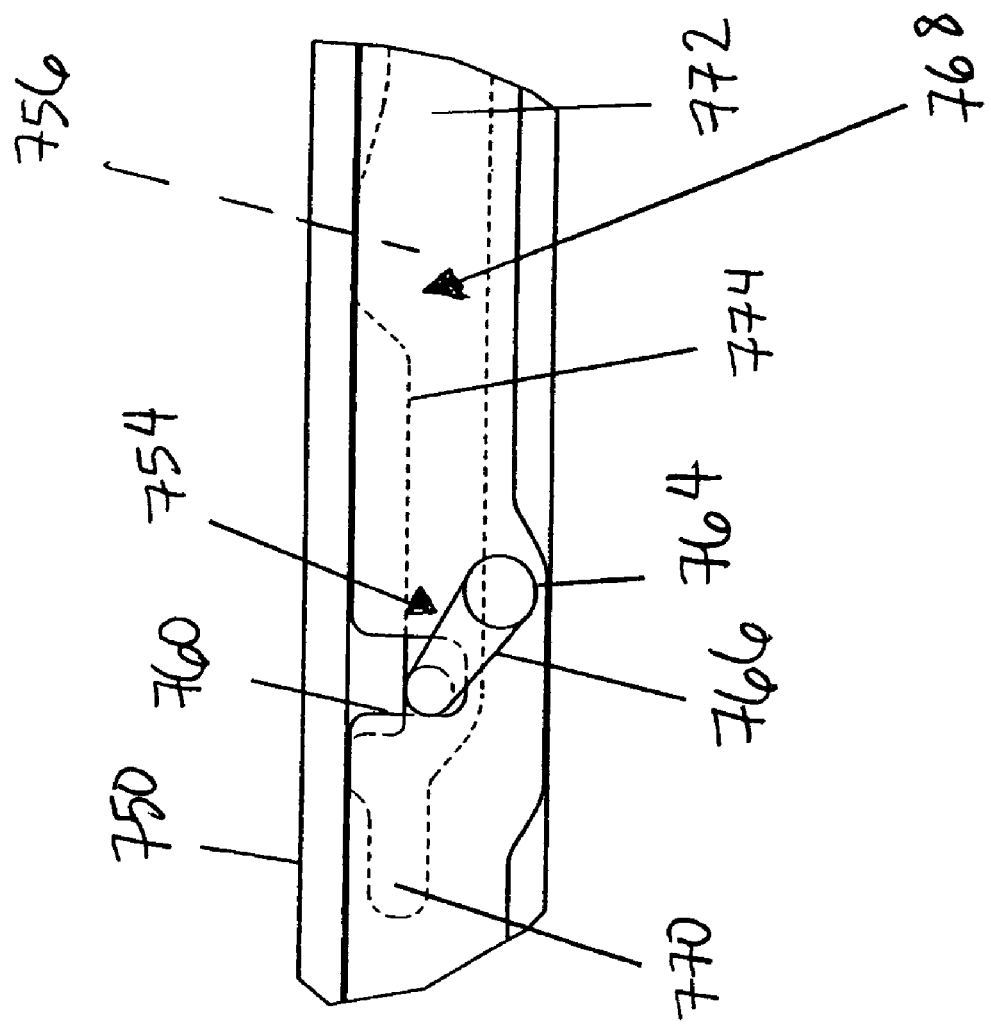

Referring now to FIGS. 87 through 89, there is shown an alternative embodiment of a number of components of the present clip applier 10. Referring to FIG. 87, there is shown an exploded view of a wedge plate 750, a link cam 752, a filler component 754, and a spindle 756.

The wedge plate 750 is similar to the embodiment shown previously and has a rounded distal end 758 and is suitably biased at the proximal end to the filler component 754. The rounded distal end 758 preferably moves in a distal manner as discussed to be disposed between the jaws 16 of the clip applier 10 for clip loading. The wedge plate 750 further has a link cam notch 760. The link cam notch 760 is in a substantially a mid-portion of the wedge plate 750. The link cam notch 760 is generally orthogonal shaped and is shaped into a lateral side of the wedge plate 750. The link cam notch 760 has a depth that is suitable to extend about to a middle of the wedge plate 750. Alternatively, the link cam notch 760 may have another shape or be circular or curved. Various configurations are possible and within the scope of the present disclosure. The link cam notch 760 preferably allows for the link cam 752 to engage and move the wedge plate 750 distally. The distal movement introduces the rounded distal end 758 between the jaws 16. Distal movement of the spindle 756 disengages the wedge plate 750 at a predetermined line of demarcation.

The filler component 754 being shown above the wedge plate 750 in FIG. 87 does not move relative to the other components and is intended to remain stationary. The filler component 754 has a link cam aperture 762. The link cam aperture 762 is a circular shaped feature that is disposed in the filler component 754 to allow the link cam 752 access. The link cam aperture 762 is in a complementary location relative to the link cam notch 760 of the wedge plate 750. The location allows a portion of the link cam 752 to engage the link cam notch 760.

The link cam 752 preferably has two discrete portions. The link cam 752 has a first base 764 and a second arm 766. The first base 764 rests and is rotatably mounted in the link cam aperture 762 of the filler component 754. The second arm 766 is connected to the first base 764. The second arm 766 is engageable with the link cam notch 760 of the wedge plate 750. The second arm 766 also has a post 767 that rides in a cam slot 768 of the spindle 756. The link cam 752 preferably has a portion that rotates to move another member a certain fixed distance, and then at the conclusion of the movement to return the member to its initial position.

Referring now to the spindle 756, the spindle 756 is shown disposed below both the filler component 754 and the wedge plate 750 in FIG. 87 and has a cam slot 768. As can be understood, referring now to the cam slot 768 from a distal starting location 770 along the cam slot 768 to a proximal ending location 772, it is understood that the post 767 of the second arm 766 of the link cam 752 rides in the cam slot 768 and follows the precise path of the cam slot 768 as the spindle 756 advances distally through the stroke. The post 767 drives the wedge plate 750 in the cam slot 768 until a certain line of demarcation is reached, then a spring (not shown) or another biasing device of the link cam 752 retracts the post 767.

Referring now to FIG. 88A, there is shown the filler component 754 resting on the wedge plate 750 in an assembled state. As can be understood from the figures, the link cam aperture 762 is shown with the first base portion 764 being in the link cam aperture 762 of the filler component 754. One skilled in the art should appreciate that the first base portion 764 can freely move or freely rotate in the link cam aperture 762 of the filler component 754. One skilled in the art should further appreciate that the first base portion 764 of the link cam 752 can rotate the second arm portion (not shown) underneath the filler component 754 with any desired degree range of rotation and with accuracy, and the clip applier 10 is not specifically limited to any specific amount of rotation.

Referring now to FIG. 88B, there is shown a view of the wedge plate 750 resting on the spindle 756 with the filler component 754 of FIG. 88A being removed simply for illustration purposes only. As can be now seen with the filler component 754 of FIG. 88A removed, the link cam 752 has the second arm 766 with the post (not shown) engaged to the link cam notch 760 of the wedge plate 750. In this manner, as the second arm 766 of the link cam 752 rotates, the post 767 will urge the wedge plate 750 distally and notably will urge the rounded distal end 758 shown on the distal side between the jaws 16 for loading the clip.

Referring now to FIG. 88C, there is shown the cam slot 768 of the spindle 756 in broken lines being beneath the wedge plate 750. In the distal most starting location 772 of the cam slot 768, the cam slot 768 will not disturb an orientation of the link cam 752. However, as the post 767 of the second arm 766 contacts cam feature 774 of the cam slot 768 shown in broken lines, the second arm 766 will be cammed counterclockwise, and thus drive the wedge plate 750 by engaging and pushing the link cam notch 760 distally. As the spindle 756 is continued to be driven distally through the stroke, the post 767 of the second arm 766 of the link cam 752 will traverse past the cam feature 774. Notably, at this location, the rounded distal end of the wedge plate 758 will be between the jaws 16 for loading.

Referring now to FIG. 89, there is shown a close up view of the link cam 754 along window 92 of FIG. 88C in the cam slot 768 of the spindle 756. As the link cam 754 is driven distally past the camming feature 774 of the spindle 756, the link cam 754 will be driven into the proximal most location 770 of the cam slot 768. This proximal most location 770 of the cam slot 768 will permit retraction of the wedge plate 750 once the jaws 16 have been loaded and as the spindle 756 is continued to advance through the stroke for firing.

Figure 90:
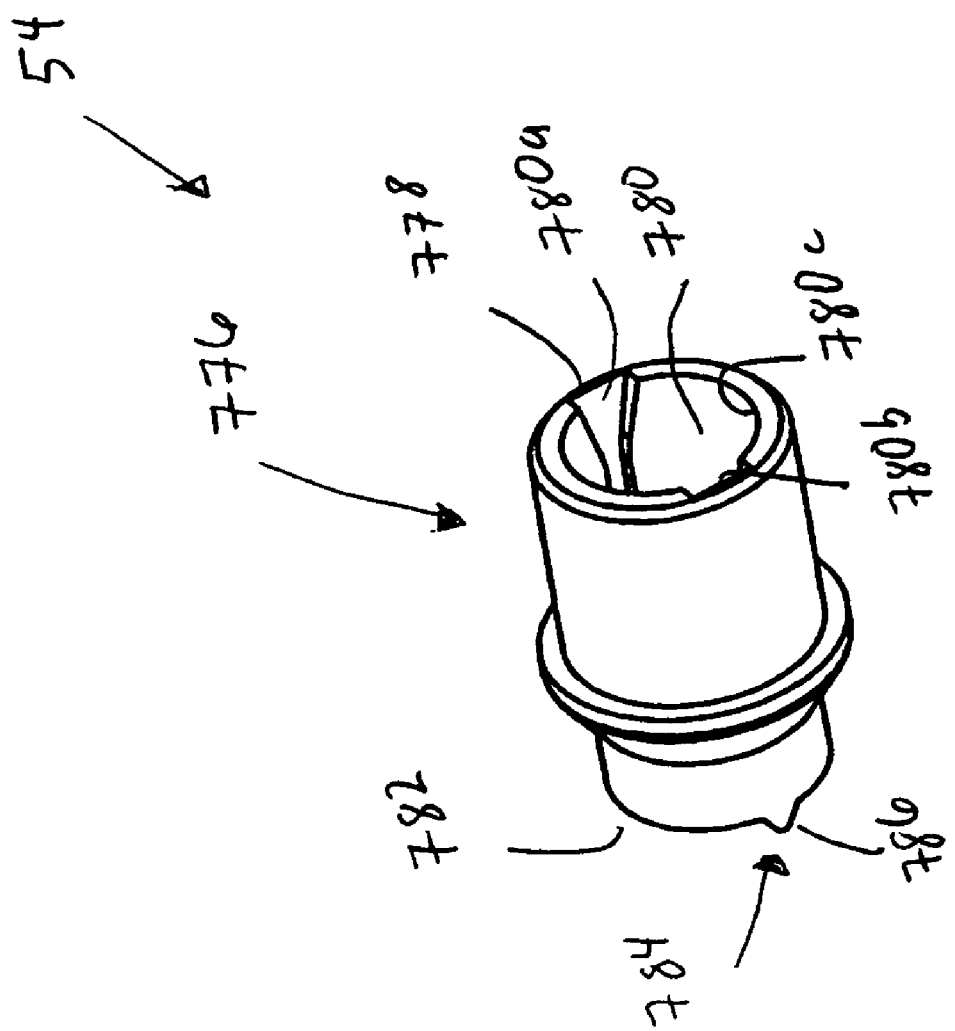

Referring now to FIG. 90, there is shown another alternative embodiment of the present clip applier 10. The clip applier 10 in this embodiment has the signaling device 54. The signaling device 54 as discussed previously provides an indication to the surgeon that a surgical event has occurred, is occurring or will occur in the future.

The surgical event may be any event associated with the clip applier 10, related to the surgical procedure, or both. In one embodiment, the surgical event may be related to the number of available surgical clips remaining in the clip applier 10. In another embodiment, the surgical event may be related to an indication of a time as to when the clip 300 is recommended to be fired. In another embodiment, the surgical event may be related to or preventing any dry firing of the clip applier and the signaling device 54 may alert the surgeon that the number of surgical clips 300 in the clip applier 10 are too low and that a new clip applier 10 or another device should be procured. In another embodiment, the surgical event may be other important or convenient parameters of the surgery such as a total time of surgery. Various configurations are possible and within the scope of the present disclosure, and the signaling device 54 preferably assist the surgeon with feedback of parameters that can not be readily seen, especially in tandem with using other endoscopic instruments.

Referring now to FIG. 90, there is shown a first component 776 of the signaling device 54. The first component 776 is a cylindrical shaped member. The first component 776 preferably has a proximal opening 778. The proximal opening 778 has a channel 780. The channel 780 also has first and second lateral sub channels 780a, and 780b that extend into the lateral sides of the first component 776. The proximal opening 778 also has an interior lateral surface 780c that is disposed to surround an interior of the channel 780.

Figure 91:
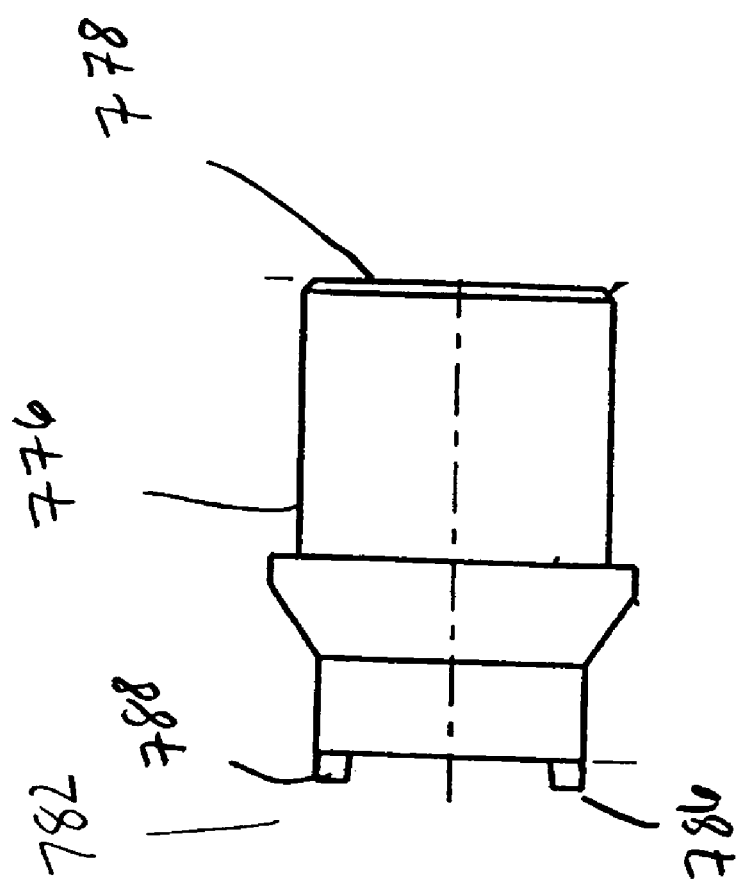
Figure 92:
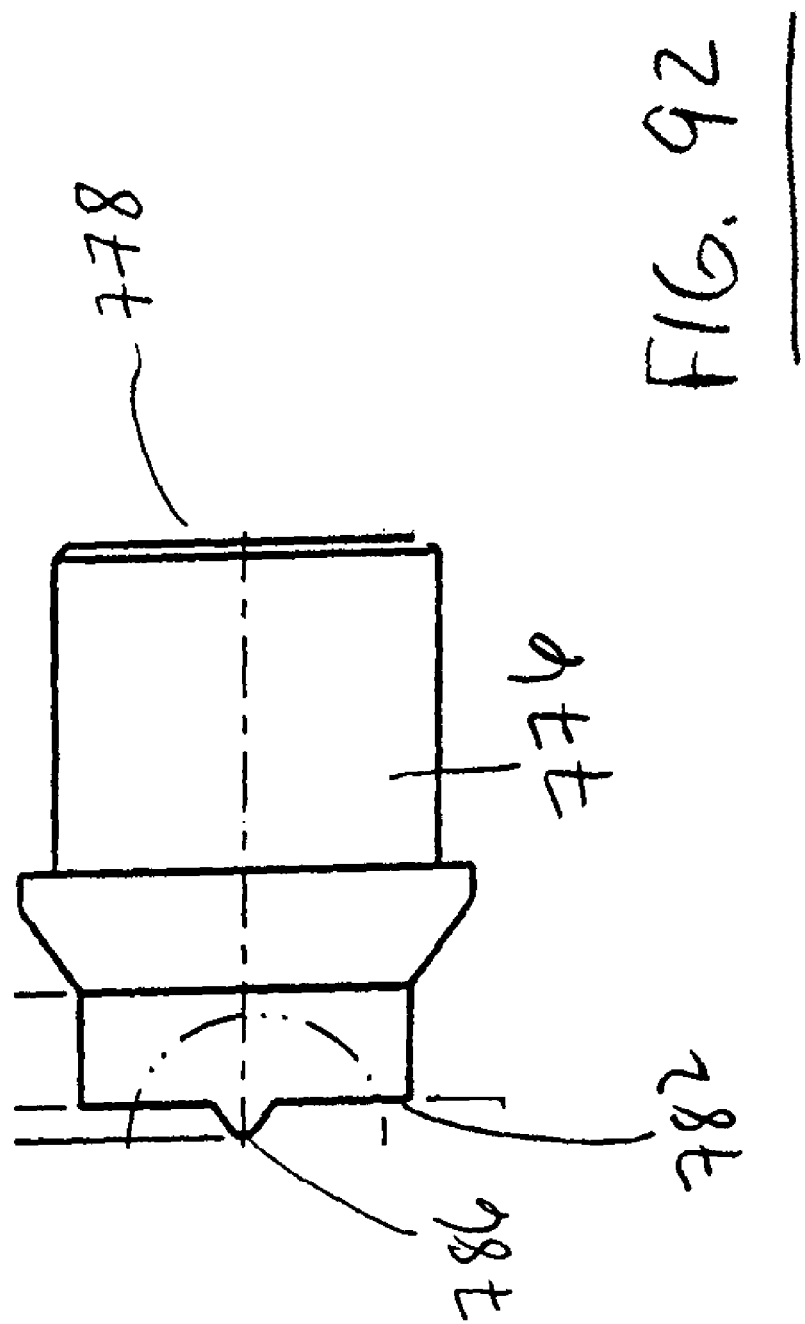

The first component 776 also has a distal side 782 having a camming feature 784. In this embodiment, the distal side 782 has the camming feature 784 being a first and a second pointed ends 786, 788. Referring now to FIG. 91, there is shown a top view of the first component 776. As can be understood from the drawings, the first and the second pointed ends 786 and 788 (the first end being obstructed by the side view of the drawing shown in FIG. 90) protrude outward and away from the first component 776 at the distal side 782. The first component 776 also has a shelf 787. Referring now to FIG. 92, there is shown a top view of the first component 776. The first component 776 (in this view) has the first and the second pointed ends 786, 788 extending outwardly from the distal side 782.

Figure 93:
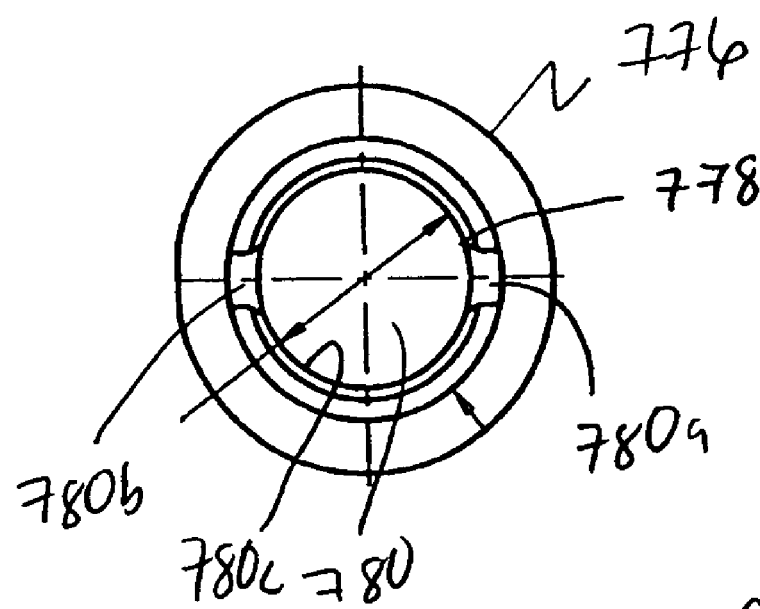

Referring now to FIG. 93, there is shown a view of the proximal opening 778 and channel 780. As can be understood the channel 780 is suitably sized to permit another member access therein. The channel 780 also has the lateral sides with the first lateral sub channel 780a and the second lateral sub channel 780b.

Figure 94:
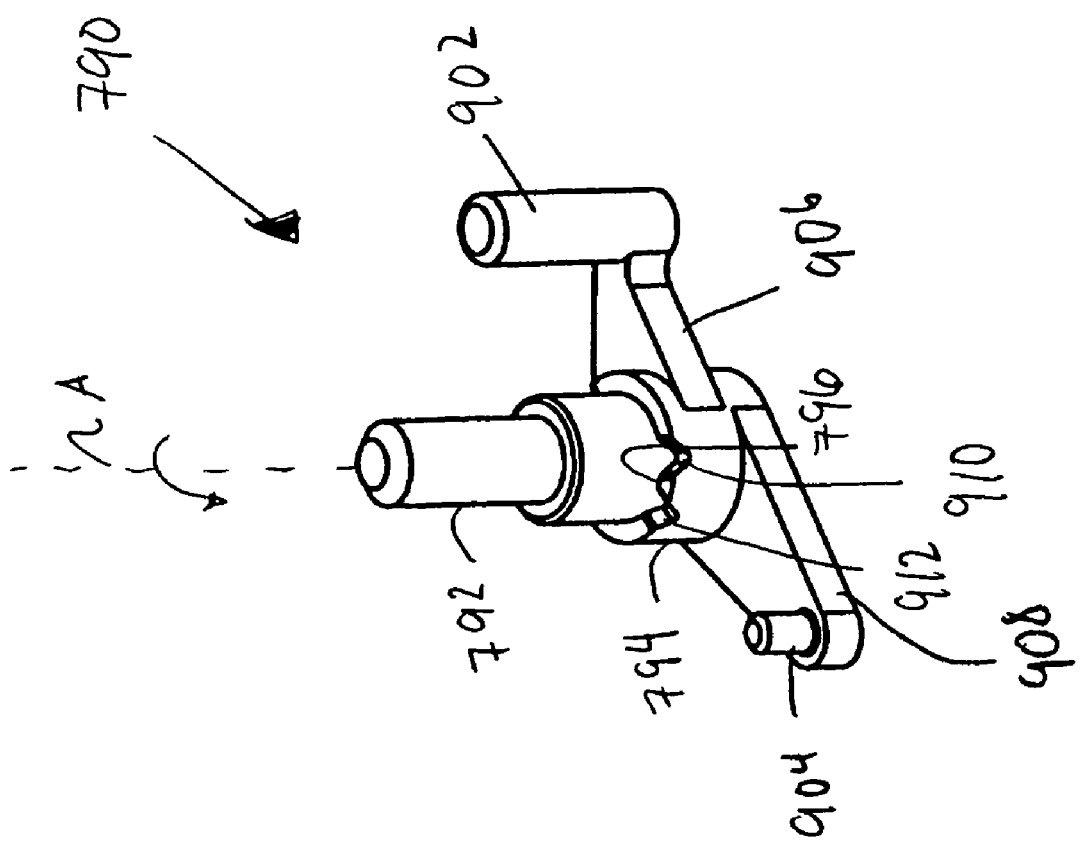

Referring now to FIG. 94, there is shown a second component 790 of the signaling device 54. The second component 790 is a lever type structure and is capable of rotation about one rotational axis shown as reference A for illustration purposes. The second component 790 has a main post 792. The main post 792 sits on a base portion 794 has a camming surface 796, and is for insertion in the first component 776. Preferably, the camming surface 796 has a suitable size to receive one of the first and the second pointed ends 786 and 788. Notably, the second component 790 rotates.

The second component 790 also has another second post 902 and a third post 904. The second post 902 is connected to the main post 792 by a linkage 906 and the third post 904 is connected to the main post 792 by another second linkage 908. Preferably, the main post 792 extends into the channel 780 of the first component 776 and the first pointed end 786 engages with a first sub recess 910 of the camming surface 796. Upon rotation, the first pointed end 786 of the first component 776 will ride in the cam surface 796 causing the first component 776 to move away from the second component 790. The first pointed end 786 will advantageously traverse from the first sub recess 910 to an adjacent second sub recess 912 when the first component 776 is rotated causing the first component 776 to move away from the second component 790 in a direction parallel to the longitudinal axis A.

Figure 95:
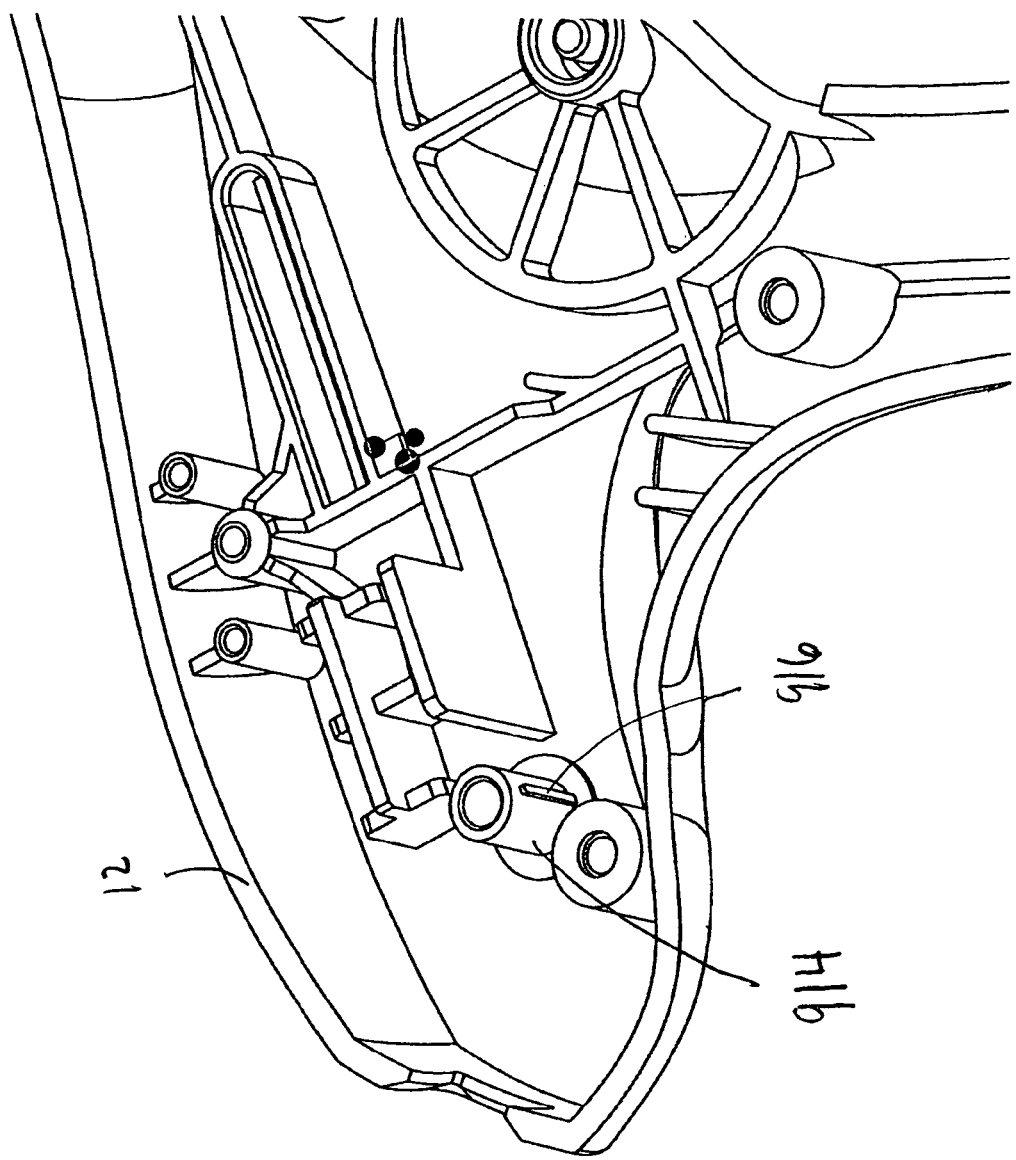

Referring now to an interior view of the handle portion 12 of the clip applier 10 shown as FIG. 95, there is shown a rib portion 914 that extends inwardly and into the handle portion 12. The rib portion 914 is a cylindrical shaped feature. The rib portion 914 is preferably molded into the handle portion 12. The rib portion 914 has a lateral strip 916. The lateral strip 916 is an orthogonal shaped member that is integrally connected with the cylindrical shaped rib portion 914.

FIG. 96 shows an interior view of an opposite lateral side of the handle portion 12 of the clip applier 10 that mates with a portion of the handle portion 12 shown in FIG. 95. FIG. 95 shows a partially assembled view of the signaling device 54 of the clip applier 10 having a spring 901 that rests on the shelf 787 of the first component 776. As can be understood from FIG. 95, the lateral strip 916 of the rib portion 916 (shown in FIG. 95) engages and is disposed through the first cylindrical portion 776. The lateral strip 916 prevents the first component 776 from rotating. As the first component 776 attempts to rotate relative to the fixed lateral strip 916 of the rib portion 914 (shown in FIG. 95), the lateral strip 916 contacts and prevents the first component from moving due to contact with a lateral side of the first lateral sub channel 780a.

Referring still to FIG. 95, the driver bar 918 is connected to actuator plate 920. The actuator plate 920 in this embodiment has a notch 922 on a proximal side thereof. The notch 922 engages the second post 902 of the second component 790. As the driver bar 918 is driven distally, the driver bar 918 will also urge the actuator plate 920 distally in a likewise manner. The actuator plate 920 having the notch 922 will also rotate the second post 902 of the second component 790 (shown in FIG.

94). The second component 790 will likewise rotate in a counter clockwise manner thereby rotating the cam notch 796 (shown in FIG. 94). The cam notch 796 (shown in FIG. 94) will also rotate and attempt to rotate the first pointed end 786 (shown in FIG. 92) of the first component 776. However, the lateral strip 916 (shown in FIG. 95) prevents such rotation. This causes the first component 776 to traverse away from the second component 790 with the spring 901 biasing the first component 776 in a direction inward toward the second component 790. The cam notch 796 will then cause the first component 776 to separate from the second component 790 and ride up the cam notch 796. As the first component 776 traverses in the cam notch 796, the first component 776 will then return and sharply contact the second component 790 due to the biasing of the spring 901. This sharp contact between the first component 776 and the second component 790 causes an audible click of the surgical event such as a clip being fired. This indication provides feedback to the surgeon that the clip has been fired. Various configuration are possible and within the scope of the present disclosure. FIG. 97 illustrates a clip 300 applied to a vessel.

In another embodiment of the present disclosure, the clip applier 1010 includes a lockout device. The lockout device is located in the handle portion 12 of the instrument 1010, and locks operation of one or more subassemblies of the instrument 1010. The lockout device is configured to prevent activation of the instrument irrespective of the force applied to the trigger 14. The lockout device in this embodiment prevents the spindle 128 from moving longitudinally. Thus, the driver bar 200 (or other subcomponents thereof) can not crimp a clip between the jaws 16a, 16b when there are no remaining clips 300 in the clip applier 10.

More particularly, after a predetermined number of clips 300 have been fired from the clip applier 1010, the clip applier 1010 will automatically lock to prevent further deployment of clips. In this manner, the lockout provides a tactile feedback to the surgeon that there are no remaining clips 300 to be applied to tissue since there are no clips 300 remaining in the clip applier 1010. Referring to FIG. 98, a number of components of the lockout device will be shown and described. FIG. 98 illustrates that the clip applier 1010 has a spring 1100 that is disposed in a predetermined location of a clip carrying channel 1102 (FIG. 99). Although shown as being associated with the clip carrying channel 1102, the spring 1100 may be disposed in other areas of the clip applier 1010, such as in a magazine, or with an embodiment where the clip applier 1010 does not include a clip carrying channel 1102, the spring 1100 may be disposed or located in other areas. The spring 1100 has a first cantilevered free end 1108 and an opposite end 1104. End 1104 is adapted to receive a lockout bar 1106 (See FIGS. 101 and 102). The clip carrying channel 1102 is reproduced in FIG. 102 and FIG. 100 in a top view. As can be understood, the distal side 1112 (FIG. 100) of the channel 1102 has the aperture 1110.

Referring to FIGS. 101 and 102, the clip applier 1010 also has a lockout bar 1106. The lockout bar 1106 is reproduced in FIG. 101 in a top view. The lockout bar 1106 includes a first end 1114, and a second opposite hook end 1116. The lockout bar 1106 is sufficiently sized so as to be wedged between a ceiling and a floor of the clip carrying channel 1102. In another embodiment, the bar may be wedged between a ceiling and a floor of a clip magazine. The groove in the second hook end 1116 is adapted to engage a clip follower 1118 (FIG. 112) of the clip applier 1010. However, the lockout bar 1106 may be removably or permanently connected to the clip follower 1118 by other methods such as a snap-fit arrangement, a friction-fit arrangement, a screw-fit arrangement, a pin arrangement, or any other arrangement such that first end 1114 may move. The lockout bar 1106 is retained between the bottom of the channel cover and the floor 1102' of the clip carrying channel 1102. The lockout bar 1106 rests in a distal slot 1117 formed in the clip follower 1118 (as shown in FIG. 112). The slot 1117 is shown as generally orthogonal, but may have any similar or different shape known in the art to permit the components to rest in the clip follower 1118. The lockout bar 1106 does not by itself lockout the clip applier 1010, but instead merely moves upwardly through the clip carrying channel 1102 when there are little or no remaining clips 300 in the clip carrying channel 1102.

FIG. 103 illustrates a partially assembled view of the lockout spring 1100 with the lockout bar 1106. Referring to FIGS. 103 and 106, clip follower 1118 biases a stack of clips 300 in a clip carrying channel 1102 in a distal manner so the clips 300 may be available to be loaded between the jaws 1016a, 1016b in order to be applied to tissue as shown in FIG. 97. The clip follower 1118 has a distal slot 1117 (FIG. 104). The lockout bar 1106 is adapted to be received in the slot 1117 and move distally with the clip follower 1118 each time the clip applier instrument 1010 is fired, and the clip follower 1118 is advanced distally.

FIG. 105 shows that the clip applier 1010 has a feed bar 1120. The feed bar 1120 reciprocates distally, then proximally during each stroke of the firing trigger to load a single clip 300 between the jaws 1016a, 1016b (FIG. 108) of the clip applier 1010. The feed bar 1120 has a distal window 1122. The feed bar 1120 is made from a thin metallic material and is moved distally by a trip lever (not shown) and trip lever spring (not shown) as previously discussed with regard to the embodiment above. The feed bar 1120 is advantageously disposed above the clip follower 1118 (shown in FIG. 107) and the clip carrying channel 1102 (shown in FIG. 109). The proximal end of the feed bar 1120 has a pair of fins 1119 (FIG. 105). The fins 1119 engage a proximal window 1134 of a spindle 1132 of the clip applier 1010 (FIG. 114). In another embodiment, the proximal end of the feed bar 1120 may have a single fin, or a member which engages window 1134 (or a particular) slot of the spindle 1132.

Referring now to FIG. 106, each time a clip 300 is fired from the instrument 1010 the clip follower 1118 will advance distally relative to the clip carrying channel 1102. FIG. 107 shows a side view of the components of the clip applier 10 with the clip follower 1118 in its distal most position, and the cover of the clip applier 1010 removed for illustration purposes. The feed bar 1120 includes a distal nose 1128 which advances the clips between the jaws (not shown). The feed bar 1120 also has a distal window 1122. The clip follower 1118 is positioned beneath the feed bar 1120 and has a slot 1117. The lockout bar 1106 is positioned in the slot 1117 of the clip follower 1118. As shown in FIG. 107, in the distal most position, the lockout bar 1106 will deflect upward and engage window 1122 of the feed bar 1120.

FIG. 108 shows a top perspective view of the components of the clip applier 1010. The clip applier 1010 has a first jaw 1016a, a second jaw 1016b, a stop 1018 connected to a cover 1020, and a feed bar 1120. Feed bar 1120 has the distal window 1122. The lockout bar 1106 extends into the distal window 1122 when the follower 1118 is in its distal most position, i.e., when there are no remaining clips. In another embodiment, the lockout bar 1106 extends into the distal window 1122 when the follower 1118 is in its partially distal most position, i.e., when there are little remaining clips such as one, two, or three remaining clips. Various arrangements and position of the window 1122 are possible and within the scope of the present disclosure, and it should be appreciated that the window 1122 can be placed at varied locations to lockout the clip applier 1010 with any number of remaining clips in the clip applier 1010.

FIG. 109 shows a top perspective view of the components of the clip applier 1010 with the cover 1020 of FIG. 108 removed and showing the nose 1128 of the feed bar 1120. As shown, the clip follower 1118 is in the clip carrying channel 1102 and will advance clips in a distal direction until it reaches its distal most position as shown. As can be seen from FIG. 109, the clip follower 1118 is in the distal most position (as an example for illustration purposes) when there are no remaining clips in the clip carrying channel 1102 or available to be fired by the clip applier 1010. The feed bar 1120 having the distal window 1122 in this distal most position aligns with the lockout bar 1106. The lockout bar 1106 in this distal most position will be deflected upwardly and extend though the distal window 1122.

FIG. 110 shows a top perspective view of the components of the clip applier 1010 with the cover 1020 and the feed bar 1120 both removed for illustration purposes to show the relationship between the lockout bar 1106 and the clip follower 1118. As seen in FIG. 110, the clip carrying channel 1102 has a number of fingers 1103" on the lateral sides of the clip carrying channel 1102 to maintain the clips (not shown) aligned in the clip carrying channel 1102. Clip follower 1118 is positioned in the clip carrying channel 1102. The lockout bar 1106 is shown positioned in the slot 1117. It should be appreciated the lockout bar 1106 and the slot 1117 may have different shapes and geometries, and the present disclosure is not limited to any particular shape or geometry. It should further be appreciated the follower 1118 and the lockout bar 1106 may be formed as an integral member with one another. Various configurations are possible and within the scope of the present disclosure.

Referring to FIG. 111, there is shown a bottom view of the clip follower 1118. In this view, the clip follower 1118 is shown as having the slot 1117 being generally orthogonal shaped and disposed along a longitudinal axis A of the clip follower 1118. As can be seen from FIG. 111, beneath the lockout bar (not shown) is the lockout spring 1100, and the spring 1100 biases the bar 1106. The lockout spring 1100 has a bulbous member 1108' at end 1108. The bulbous member 1108' of spring 1100 is large enough so as to pass over and avoid being caught in the aperture 1110 in the clip carrying channel 1102 (shown in FIG. 100).

Once the member 1108' of spring 1100 reaches a predetermined point on the clip carrying channel floor 1102' or a location where member 1108' is located past aperture 1110 in FIG. 100, the hook portion 1116 of the lockout bar 1106 will fit into and engage aperture 1110.

Referring to FIG. 112, there is shown a cross sectional view of the clip follower 1118 having the lockout bar 1106 positioned in the slot 1117 of the clip follower 1118. The view is taken along section line 16-16 of FIG. 111. Slot 1117 of the clip follower 1118 has a pin 1117a that is disposed in the groove on the hook portion 1116 of the lockout bar 1106. Pin 1117a prevents the lockout bar 1106 from being separated from the clip follower 1118 during distal movement.

Disposed underneath the lockout bar 1106 is the lockout spring 1100 that biases the lockout bar 1106 in a direction opposite the clip carrying channel 1102 as shown in FIG. 111. Prior to the last clip being applied, the lockout bar 1106 is retained between the bottom surface of the channel cover and the floor 1102' of the clip carrying channel 1102.

FIG. 107 illustrates that at the distal most position of the clip follower 1118, the lockout spring 1100 will move and rotate the free end 1114 of the lockout bar 1106 to a position extending above the clip carrying channel 1102. Thus, the free end 1114 of the lockout bar 1106 will rotate upward and escape through the ceiling 1103' of the clip carrying channel 1102 at the distal position of the clip follower 1118 to engage the distal most window 1122 of the feed bar 1120 as shown in FIG. 107. The hook portion 1116 of the lockout bar 1106 will rotate down and engage aperture 1110 in the floor of the clip carrying channel 1102.

The distal window 1122 of the feed bar 1120 is shown above immediately adjacent to the nose 1128 of the feed bar 1120 (FIG. 113). The free end 1114 of the lockout bar 1106 of FIG. 107 will move above and through the clip carrying channel 1102 and will engage the distal window 1122 of the feed bar 1120 as shown in FIG. 107.

A spindle 1132 is shown in FIGS. 114 and 115. On a proximal side, the window 1134 is suitably sized and positioned such that the fins 1119 of the feed bar 1120 (shown in FIG. 105) simply rest in the window 1134 of the spindle 1132 during normal operation of the clip applier 1010 without effecting the distal or proximal movement of the spindle 1132. The window 1134 is shown in an enlarged view in FIG. 116.

As shown in FIG. 116, the window 1134 has a generally orthogonal shape and the outer lateral surface of the window 1134 will not interfere or contact other components during the normal operation of the clip applier 1010. The feed bar 1120 (shown in FIG. 105) is a thin member relative to the spindle 1132 of FIG. 116. In one embodiment, the feed bar 1120 is a thin metallic member. In another, the feed bar 1120 is a thin thermoplastic member. The feed bar 1120 is suitable for reciprocation distally and proximally relative to the spindle 1132. When the fins 1119 hook the distal edge of window 1134 of spindle 1132, the feed bar 1120 prevents retraction but not advancement of the spindle 1132.

However, given that the spindle 1132 cannot retract fully proximally, the pawl 1146 in the handle portion (FIG. 117) cannot return to the home or initial position relative to the rack 1140 in the handle portion 12 of the clip applier 1010. Instead, as shown in FIG. 118, the pawl 1146 will remain in an intermediate position relative to the rack 1140. When the trigger (not shown) is squeezed, pawl 1146 cannot rotate enough to be free of the rack 1140 or move clockwise to reset the pawl 1146 to the home (or at rest position for the next firing of the instrument as shown in FIG. 117). Thus, the pawl 1146 and rack 1136 lockout the trigger 14 from being squeezed and the spindle 1132 cannot move distally to engage the driver bar (FIGS. 26 and 27) and subsequently the clip applier 1010 is unable to close the jaws 1016a, 1016b. The surgeon will feel a strong tactile feedback from the trigger 14 and resistance that the trigger 14 cannot be compressed toward the handle 12 any further, thus signaling that the clip applier 1010 needs to be disposed/replaced with a new instrument.

Turning now to FIG. 119, there is shown a perspective view of a shear pin 1148 for a secondary lockout mechanism 1150. The shear pin 1148 is a generally cylindrical member having a three-part body 1152 defining a first neck portion 1154 and a second neck portion 1156. The first neck portion and the second neck portion 1154, 1156 respectively have a width that is less than a width of the body 1152 and are configured to engage a linkage 1160. More particularly, trigger 1156 is connected to linkage 1160, which, in turn, engages the first and the second neck portions 1154 and 1156 of pin 1148.

Referring now to FIG. 120, there is shown a side cross sectional view of the clip applier 1010 having the rack 1140 and pawl 1146 locking out the spindle 1132 as described above with the secondary lockout mechanism 1150. As shown, the trigger 1156 will be prevented from advancing the spindle 1132 distally since the rack 1140 and the pawl 1146 prevent the spindle 1132 from retracting proximally as discussed above. However, in this embodiment, the instrument 1010 has a secondary lockout 1150 to prevent the surgeon from placing too much force on the trigger 1156 and the handle 1158 which could possibly overcome or dislodge the engagement between the rack 1140 and the pawl 1146, and move the spindle 1132 distally.

Turning now to FIG. 121, if a force F1 is placed on the trigger 1156, the trigger 1156 will move toward the handle 1158 to advance the link 1160. The link 1160 will advance the shear pin 1148 distally to advance the spindle 1132 distally by spindle link 1132a. The engagement between the pawl 1146 and the rack 1140 will prevent the spindle 1132 from moving distally as discussed above. However, now turning to FIG. 122, if a force F2 (that is greater than the force F1) is applied to the trigger 1156 to further compress the trigger 1156 which could potentially dislodge the engagement between the rack 1140 and the pawl 1146, the force F2 will break shear pin 1148. Thus, the connection between the trigger 1156 and the spindle 1132 is broken and the link 1160 cannot advance the spindle link 1132a distally. Thus, a secondary lockout is achieved.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

The invention claimed is:

1. An apparatus for application of surgical clips to body tissue, which comprises:
 a) a handle portion;
 b) a body extending distally from the handle portion and defining a longitudinal axis;
 c) a plurality of surgical clips disposed within the body;
 d) a jaw assembly mounted adjacent a distal end portion of the body, the jaw assembly including first and second jaw portions movable between a spaced-apart and an approximated position;
 e) a feed bar configured to individually distally advance a surgical clip to the jaw assembly while the jaw portions are in the spaced apart position;
 f) a clip pusher disposed proximal to the plurality of clips and configured to bias the plurality of clips in a distal manner;
 g) an actuator at least partially disposed within the body and longitudinally movable in response to actuation of the handle portion;
 h) a jaw closure member positioned adjacent the first and second jaw portions to move the jaw portions to the approximated position;
 i) a rack having a plurality of ratchet teeth being connected to the actuator;
 j) a pawl having at least one tooth configured to engage the ratchet teeth, the pawl being biased in the handle portion, wherein as the actuator is moved longitudinally, the plurality of ratchet teeth are passed over the pawl, the pawl configured to prevent inadvertent return of the actuator before full actuation of the apparatus;
 k) a bar being disposed in proximity to the feed bar, the bar being biased by a spring and lodged between a ceiling and a floor of a clip carrying channel, wherein the clip carrying channel includes a distal window; and
 wherein as the clip pusher moves distally each time a clip is released from the apparatus, the clip pusher moves the bar distally, and wherein when the bar is in substantial alignment with the distal window, the bar deflects through the distal window of the feed bar to a second position, the bar in the second position preventing the actuator from moving proximally thereby manipulating the pawl to be engaged with the ratchet teeth of the rack, the pawl and rack preventing the actuator from longitudinally moving.

2. The apparatus of claim 1, wherein the feed bar has a proximal fin, the fin being configured to prevent the actuator from moving proximally in the second position.

3. The apparatus of claim 1, wherein the feed bar has a pair of proximal fins with at least one being configured to prevent the actuator from moving proximally in the second position.

4. The apparatus of claim 1, wherein the feed bar has a pair of proximal fins with the pair being connected and having a "U" shape with at least one being configured to prevent the actuator from moving proximally in the second position.

5. The apparatus of claim 2, wherein the actuator has a proximal window, wherein the fin engages with the window to prevent the actuator from moving proximally in the second position.

6. The apparatus of claim 1, wherein the spring and the bar are disposed in a channel of the clip pusher with the spring being located under the bar.

7. The apparatus of claim 1, wherein the bar is a resilient member.

8. The apparatus of claim 1, wherein the rack and the pawl are located in the handle.

9. The apparatus of claim 1, wherein the rack having the plurality of ratchet teeth is connected to the handle portion, and wherein the pawl is connected to the actuator.

10. The apparatus of claim 1, wherein the distal window is located at an end of the clip carrying channel.

11. The apparatus of claim 1, wherein the pawl is engaged with the rack, and wherein the pawl and the rack prevent the actuator from longitudinally moving when there are no clips in the clip carrying channel.

12. The apparatus of claim 1, wherein the pawl is engaged with the rack and the pawl and rack prevent the actuator from longitudinally moving when there are two clips of the plurality of clips in the clip carrying channel.

13. The apparatus of claim 1, wherein the feed bar is in the second position, and wherein the feed bar prevents the actuator from moving proximally thereby manipulating the pawl to be engaged with the teeth of the rack in a substantially intermediate position of the rack, the pawl and the rack being engaged, the engagement thereby preventing the actuator from moving longitudinally.

14. The apparatus of claim 1, wherein in the second position the feed bar is not parallel with the longitudinal axis.

15. The apparatus of claim 1, wherein the feed bar moves from an initial position to the second position, the second position being a position that is deflected from the longitudinal axis.

16. An apparatus for application of surgical clips to body tissue, which comprises:
 a) a handle portion;
 b) a body extending distally from the handle portion and defining a longitudinal axis;
 c) a plurality of surgical clips disposed within the body;

d) a jaw assembly mounted adjacent a distal end portion of the body, the jaw assembly including first and second jaw portions movable between a spaced apart and an approximated position;

e) a feed bar configured to individually distally advance a surgical clip to the jaw assembly while the jaw portions are in the spaced apart position, the feed bar having at least one proximal fin;

f) a clip pusher disposed proximal to the plurality of clips and configured to bias the plurality of clips in a distal manner;

g) an actuator at least partially disposed within the body and longitudinally movable in response to actuation of the handle portion, the actuator having a proximal window;

h) a jaw closure member positioned adjacent the first and second jaw portions to move the jaw portions to the approximated position;

i) a rack having a plurality of ratchet teeth being connected to said actuator; and j) a pawl having at least one tooth configured to engage the ratchet teeth, the pawl being biased in the handle portion, wherein as the actuator is moved longitudinally, the plurality of ratchet teeth are passed over the pawl, the pawl configured to prevent inadvertent return of the actuator before full actuation of the apparatus;

k) a bar being disposed in proximity to the feed bar, the bar being biased by a spring and lodged between a ceiling and a floor of a clip carrying channel, wherein the clip carrying channel includes a distal window;

wherein as the clip pusher moves distally each time a clip is released from the apparatus, the clip pusher moves the bar distally, and wherein when the bar is in substantial alignment with the distal window, the bar being biased by the spring deflects through the distal window of the feed bar to a second position, the bar in the second position having the proximal fin in engagement with the proximal window of the actuator, the engagement of the feed bar and the actuator preventing retraction but not advancement of the actuator and thereby manipulating the pawl to be engaged with the rack in a substantially intermediate position; and wherein the pawl and rack prevent the actuator from moving longitudinally to thereby lock the actuator.

17. The apparatus of claim 16, wherein the actuator comprises a spindle.

18. The apparatus of claim 16, wherein the feed bar comprises at least two proximal fins.

19. The apparatus of claim 16, wherein the feed bar comprises at least two proximal fins connected at an end to form a "U" shape.

20. The apparatus of claim 16, wherein the spring is a leaf spring, wherein the leaf spring and the bar are disposed in a channel located distal of the clip pusher, wherein the leaf spring is disposed under the bar and configured to bias the bar upwardly relative to the floor of the clip carrying channel.

21. The apparatus of claim 20, wherein the bar has a hooked proximal end that engages with a portion of the clip pusher in the channel so the bar moves distally with the clip pusher.

22. The apparatus of claim 21, wherein the proximal hooked end engages with an aperture on the floor to manipulate the lockout bar upwardly relative to the floor of the clip carrying channel, and wherein when the bar is in alignment with the distal window of the clip carrying channel, the proximal hooked end engages with an aperture disposed in floor of the clip carrying channel.

23. The apparatus of claim 16, wherein the proximal fin rests in the proximal window and does not interfere with the movement of the actuator when the actuator reciprocates longitudinally during a firing stroke.

24. An apparatus for application of surgical clips to body tissue, which comprises:

a) a handle portion;

b) a body extending distally from the handle portion and defining a longitudinal axis;

c) a plurality of surgical clips disposed within the body;

d) a jaw assembly mounted adjacent a distal end portion of the body, the jaw assembly including first and second jaw portions movable between a spaced-apart and an approximated position;

e) a feed bar configured to individually distally advance a surgical clip to the jaw assembly while the jaw portions are in the spaced apart position, a bar being disposed in proximity to the feed bar, the bar being biased by a spring and lodged between a ceiling and a floor of a clip carrying channel;

f) a clip pusher disposed proximal to the plurality of clips and configured to bias the plurality of clips in a distal manner;

g) an actuator at least partially disposed within the body and longitudinally movable in response to actuation of the handle portion;

h) a jaw closure member positioned adjacent the first and second jaw portions to move the jaw portions to the approximated position;

i) a rack having a plurality of ratchet teeth being connected to said actuator; and j) a pawl having at least one tooth configured to engage said ratchet teeth, the pawl being biased in the handle portion, wherein as the actuator is moved longitudinally, the plurality of ratchet teeth are passed over the pawl, the pawl configured to prevent inadvertent return of the actuator before full actuation of the apparatus; and wherein the clip pusher incrementally moves distally each time a clip is released from the apparatus, and wherein when the clip pusher reaches a predetermined distal point in the clip carrying channel, the bar is deflected to a second position, the bar in the second position having a portion being in engagement with the actuator, the bar in the second deflected position preventing retraction but not advancement of the actuator and thereby manipulating the pawl to be engaged with ratchet teeth of the rack, the pawl and rack preventing the actuator from moving longitudinally to thereby lock the actuator.

25. The apparatus of claim 24, wherein the apparatus is configured for endoscopic surgical applications.

26. The apparatus of claim 25, wherein the apparatus has the body being configured for bariatric surgery.

27. An apparatus for application of surgical clips to body tissue, which comprises:

a) a handle portion;

b) a body extending distally from the handle portion and defining a longitudinal axis;

c) a plurality of surgical clips disposed within the body;

d) a jaw assembly mounted adjacent a distal end portion of the body, the jaw assembly including first and second jaw portions movable between a spaced-apart and an approximated position;

e) a feed bar configured to individually distally advance a surgical clip to the jaw assembly while the jaw portions are in the spaced apart position, a bar being disposed in proximity to the feed bar, the bar being biased by a spring and lodged between a ceiling and a floor of a clip carrying channel;

f) a clip pusher disposed proximal to the plurality of clips and configured to bias the plurality of clips in a distal manner;

g) an actuator at least partially disposed within the body and longitudinally movable in response to actuation of the handle portion;

h) a jaw closure member positioned adjacent the first and second jaw portions to move the jaw portions to the approximated position;

i) a rack having a plurality of ratchet teeth being connected to said actuator; and j) a pawl having at least one tooth configured to engage said ratchet teeth, the pawl being biased in the handle portion, wherein as the actuator is moved longitudinally, the plurality of ratchet teeth are passed over the pawl, the pawl configured to prevent inadvertent return of the actuator before full actuation of the apparatus; and wherein the clip pusher incrementally moves distally each time a clip is released from the apparatus, and wherein when the clip pusher reaches a predetermined distal point in the clip carrying channel, the bar is deflected to a second position, the bar in the second position having a portion being in engagement with the actuator, the bar in the second deflected position preventing retraction but not advancement of the actuator and thereby manipulating the pawl to be engaged with ratchet teeth of the rack, the pawl and rack preventing the actuator from moving longitudinally to thereby lock the actuator; and k) a secondary lockout device configured to break a connection between the handle portion and the actuator and prevent longitudinal movement of the actuator in response to actuation of the handle portion when a predetermined force is applied to the handle portion, the predetermined force being less than the force required to dislodge the ratchet teeth from the pawl.

28. The apparatus of claim 27, wherein the secondary lockout device includes a link connecting the actuator to the handle and a shear pin connecting the link to the actuator.

29. The apparatus of claim 28, wherein the shear pin is generally cylindrical and includes a body having a first diameter and a second section having a second diameter that is less than the first diameter, wherein upon application of the predetermined force the shear pin breaks along the second diameter.

* * * * *